United States Patent
Comer et al.

(10) Patent No.: US 11,325,913 B2
(45) Date of Patent: *May 10, 2022

(54) COMPOUNDS AND METHODS FOR THE TREATMENT OF MALARIA

(71) Applicant: THE BROAD INSTITUTE, INC., Cambridge, MA (US)

(72) Inventors: Eamon Comer, Cambridge, MA (US); Nobutaka Kato, Cambridge, MA (US); Christina Scherer, Cambridge, MA (US); Jessica Bastien, Cambridge, MA (US); Jeremy Duvall, Cambridge, MA (US); Timothy Lewis, Cambridge, MA (US); Morgane Sayes, Cambridge, MA (US); Matthew Leighty, Cambridge, MA (US); Jun Pu, Cambridge, MA (US); Jennifer Beaudoin, Cambridge, MA (US); Bertrand Braibant, Cambridge, MA (US); Benito Munoz, Cambridge, MA (US)

(73) Assignee: THE BROAD INSTITUTE, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/915,660

(22) Filed: Jun. 29, 2020

(65) Prior Publication Data

US 2020/0399276 A1  Dec. 24, 2020

Related U.S. Application Data

(63) Continuation of application No. 16/042,827, filed on Jul. 23, 2018, now Pat. No. 10,738,055, which is a continuation of application No. 15/035,044, filed as application No. PCT/US2014/064962 on Nov. 11, 2014, now Pat. No. 10,059,711.

(60) Provisional application No. 61/902,356, filed on Nov. 11, 2013.

(51) Int. Cl.
*C07D 487/04* (2006.01)
(52) U.S. Cl.
CPC .................. *C07D 487/04* (2013.01)
(58) Field of Classification Search
CPC ................................................. C07D 487/04
See application file for complete search history.

(56) References Cited

U.S. PATENT DOCUMENTS

| 3,176,017 A | 3/1965 | Freed |
| 10,059,711 B2 | 8/2018 | Comer et al. |
| 2019/0055252 A1 | 2/2019 | Comer et al. |

FOREIGN PATENT DOCUMENTS

JP  6591429 B2  10/2019

OTHER PUBLICATIONS

PubChemCID 54668627 (Year: 2011).*
PubChemCID 54666393, Create Date: Dec. 20, 2011.
PubChemCID 54667196, Create Date: Dec. 20, 2011.
PubChemCID 54668159, Create Date: Dec. 20, 2011.
PubChemCID 54669399, Create Date: Dec. 20, 2011.
PubChemCID 54669400, Create Date: Dec. 20, 2011.
PubChemCID 118065266, Create Date Feb. 23, 2016.
Hearing Notice in corresponding Indian Patent Application No. 201617019754, dated May 10, 2021 (2 pages).
Examination Report dated May 14, 2021 in corresponding European Patent Application No. 14861002.5 (8 pages).
Office Action issued in corresponding Japanese Patent Application No. JP 2019-169028, dated Oct. 13, 2020 (2 pages).
English translation of the Office Action issued in corresponding Japanese Patent Application No. JP 2019-169028, dated Oct. 13, 2020 (2 pages).
Lowe et al., "Synthesis and Profiling of a Diverse Collection of Azetidine-Based Scaffolds for the Development of CNS-Focused Lead-like Libraries," The Journal of Organic Chemistry, 2012, vol. 77, pp. 7187-7211.
Nivsarkar et al., "Design, synthesis and biological evaluation of novel bicyclic beta-lactams as potential antimalarials," Bioorganic & Medicinal Chemistry Letters, Mar. 2005, vol. 15, pp. 1371-1373.
PubChemCID 5456548, created Jul. 10, 2005.
PubChemCID 5466548, created Mar. 27, 2005.
PubChemCID 54651996, created Dec. 20, 2011, downloaded Mar. 19, 2015; p. 3, Figure; p. 8, Table, 10 pages.

(Continued)

*Primary Examiner* — Jeffrey S Lundgren
*Assistant Examiner* — Ibrahim D Bori
(74) *Attorney, Agent, or Firm* — Melissa Hunter-Ensor; Scott Goncher; Greenberg Traurig, LLP

(57) ABSTRACT

Provided herein are compounds of the formula (I):

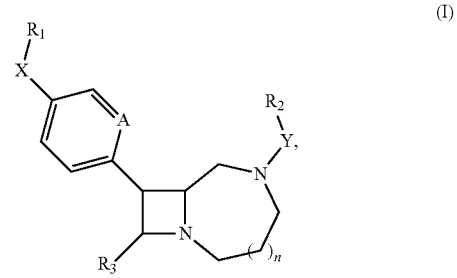

as well as pharmaceutically acceptable salts thereof, wherein the substituents are as those disclosed in the specification. These compounds, and the pharmaceutical compositions containing them, are useful for the treatment of malaria.

20 Claims, 3 Drawing Sheets

(56) References Cited

OTHER PUBLICATIONS

PubChemCID 54666387, created Dec. 20, 2011, 12 pages.
PubChemCID 54666395, created Dec. 20, 2011, 12 pages.
PubChemCID 54666403, created Dec. 20, 2011, 11 pages.
PubChemCID 54666420, created Dec. 20, 2011, 12 pages.
PubChemCID 54666521, created Dec. 20, 2011, modified Jun. 21, 2020, 11 pages.
PubChemCID 54666548, created Dec. 20, 2011, 13 pages.
PubChemCID 54666656, created Dec. 20, 2011, modified Jun. 21, 2020, 10 pages.
PubChemCID 54666732, created Dec. 20, 2011, 11 pages.
PubChemCID 54666782, created Dec. 20, 2011, modified Jun. 21, 2020, 9 pages.
PubChemCID 54666794, created Dec. 20, 2011, modified Jun. 21, 2020, 9 pages.
PubChemCID 54667060, created Dec. 20, 2011, 12 pages.
PubChemCID 54667656, created Dec. 20, 2011, 10 pages.
PubChemCID 54668298, created Dec. 20, 2011, 12 pages.
PubChemCID 54668300, created Dec. 20, 2011, 12 pages.
PubChemCID 54668447, created Dec. 20, 2011, 11 pages.
PubChemCID 54668626, created Dec. 20, 2011.
PubChemCID 54668630, created Dec. 20, 2011.
PubChemCID 54668907, created Dec. 20, 2011, downloaded Jan. 3, 2015; p. 1, Figure; p. 2, Table, 3 p. .
PubChemCID 54668942, created Dec. 20, 2011.
PubChemCID 54669190, created Dec. 20, 2011, modified Jun. 21, 2020, 9 pages.
Office Action issued in corresponding Indian Patent Application No. 201617019754, dated Jun. 24, 2019 (7 pages).
Examination Report issued in corresponding European Patent Application No. 14861002.5, dated Feb. 11, 2019 (8 pages).
Extended European Search Report issued in corresponding European Patent Application No. 14861002.5, dated Mar. 21, 2017 (14 pages).
International Search Report and Written Opinion issued in corresponding International Patent Application No. PCT/US2014/064962, dated Apr. 1, 2015 (11 pages).
Translation of Notice of Reasons for Rejection issued in corresponding Japanese Patent Application No. 2016-553266, dated Oct. 16, 2018 (4 pages).
Translation of Notice of Reasons for Rejection issued in corresponding Japanese Patent Application No. 2016-553266, dated Mar. 25, 2019 (3 pages).
Office Action dated Jun. 29, 2021 in corresponding Japanese Patent Application No. 2019-169028 (2 pages).
English Translation of the Office Action dated Jun. 29, 2021 in corresponding Japanese Patent Application No. 2019-169028 (1 page).

* cited by examiner

COMPOUNDS AND METHODS FOR THE TREATMENT OF MALARIA

CROSS-REFERENCE TO RELATED APPLICATIONS

This application is a continuation of U.S. patent application Ser. No. 16/042,827, filed on Jul. 23, 2018 (now allowed), which is a continuation of U.S. patent application Ser. No. 15/035,044, filed on May 6, 2016, which is the U.S. national phase application, pursuant to 35 U.S.C. § 371, of PCT International Application Ser. No. PCT/US14/64962, filed on Nov. 11, 2014, designating the United States and published in English, which claims priority to and the benefit of U.S. Provisional Application No. 61/902,356, filed Nov. 11, 2013; each of the aforementioned applications are incorporated herein by reference in their entirety.

BACKGROUND OF THE INVENTION

Malaria is a vector-borne infectious disease caused by protozoan parasites and is widespread in tropical and subtropical regions, including parts of the Americas, Asia and Africa. Of the five *Plasmodium* parasite species that can infect humans (*P. falciparum, P. vivax, P. ovale, P. malariae,* and *P. knowlesi*), the most serious forms of the disease are caused by *P. falciparum* and *P. vivax*. Approximately 515 million people are stricken with malaria each year, and between one and three million of these people die from the disease. The current armament of approved anti-malarial drugs, such as chloroquine, atovaquone, pyrimethamine, and sulfadoxine, is limited to only a few targets within the human malaria parasite, and growing widespread resistance to current drugs is prompting the development of new antimalarial agents that have new biological targets.

SUMMARY OF THE INVENTION

The present invention is directed to compounds of formula I:

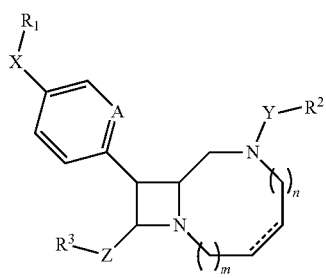

Formula I wherein the dotted line represents an optional double bond;
m is 0 or 1;
n is 0, 1, or 2;
A is CH or N;
X is absent or —C≡C—;
$R^1$ is hydrogen, $C_1$-$C_6$ alkyl, $C_1$-$C_6$ heteroalkyl, $C_6$-$C_{10}$ aryl, $C_3$-$C_{10}$ carbocyclyl, or $C_2$-$C_9$ heteroaryl;
Y is $C_1$-$C_6$ alkylene, —C(O)NR$^4$—; —SO$_2$—, or —C(O)—;
$R^2$ is $C_1$-$C_6$ perfluoroalkyl, $C_6$-$C_{10}$ aryl, $C_6$-$C_{10}$ aryl $C_1$-$C_6$ alkyl, $C_3$-$C_{10}$ carbocyclyl, or $C_2$-$C_9$ heteroaryl;

Z is absent, $C_1$-$C_6$ alkylene, or $C_1$-$C_6$ heteroalkylene;
$R^3$ is hydrogen, hydroxyl, —NR$^5$R$^6$, —C(O)R$^7$, or $C_2$-$C_9$ heterocyclyl;
$R^4$ is hydrogen or $C_1$-$C_6$ alkyl;
$R^5$ and $R^6$ are independently hydrogen, $C_1$-$C_6$ alkyl, or $C_1$-$C_6$ acyl; and
$R^7$ is hydroxyl, $C_1$-$C_6$ heteroalkyl, or $C_2$-$C_9$ heterocyclyl;
wherein said compound does not have the structure of any one of compounds 1 to 30 of Table 1;
or a pharmaceutically acceptable salt thereof.

In some embodiments, the compound has the structure:

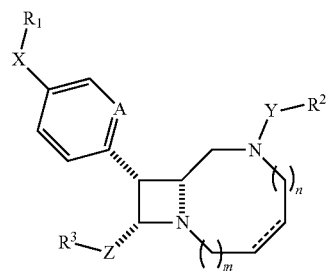

Formula IA

In some embodiments, the compound has the structure:

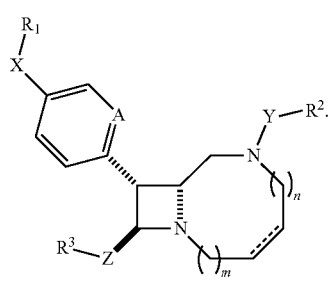

Formula IB

In some embodiments, the compound has the structure:

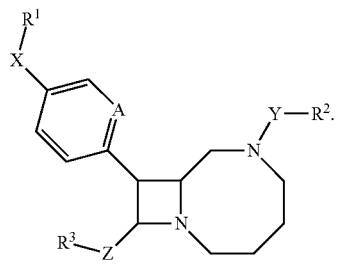

Formula II

In certain embodiments, the compound of Formula II has the stereochemistry of Formula IA or IB.

In other embodiments, the compound has the structure:

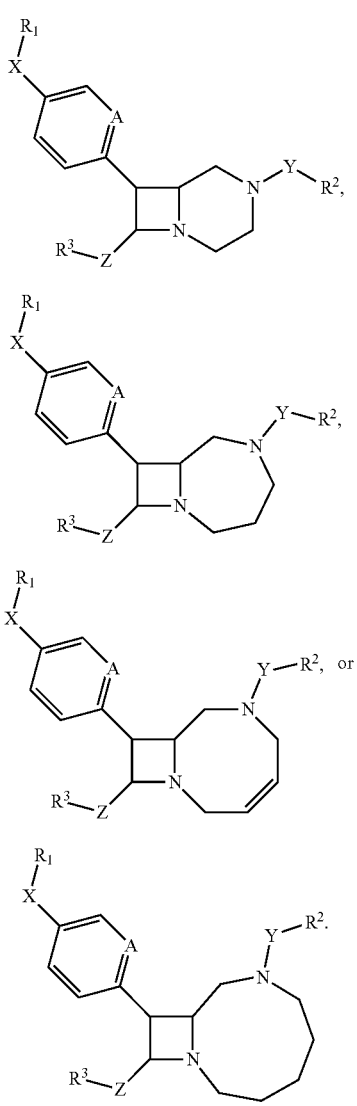

Formula III

Formula IV

Formula V, or

Formula VI

In certain embodiments, the compound of Formula III, IV, V, or VI has the stereochemistry of Formula IA or IB.

In some embodiments, A is CH. In other embodiments, A is N.

In certain embodiments, X is —C≡C—.

In some embodiments, $R^1$ is $C_6$-$C_{10}$ aryl (e.g., phenyl, 2-methoxy-phenyl, 4-methoxy-phenyl, 2-fluoro-phenyl, 3-fluoro-phenyl, 4-fluoro-phenyl, 2,4-difluoro-phenyl, or 3,4-difluorophenyl).

In other embodiments, Y is —C(O)$NR^4$— (e.g., wherein $R^4$ is hydrogen or methyl).

In certain embodiments, $R^2$ is $C_6$-$C_{10}$ aryl (e.g., phenyl, 2-methoxy-phenyl, 3-methoxy-phenyl, 4-methoxy-phenyl, 2-fluoro-phenyl, 3-fluoro-phenyl, or 4-fluoro-phenyl), $C_3$-$C_{10}$ carbocyclyl (e.g., cyclohexyl), or $C_2$-$C_9$ heteroaryl (e.g., pyridyl such as 3-pyridyl or 4-pyridyl). In some embodiments, $R^2$ is 4-substituted phenyl such as 4-methoxy-phenyl.

In other embodiments, the compound has the structure:

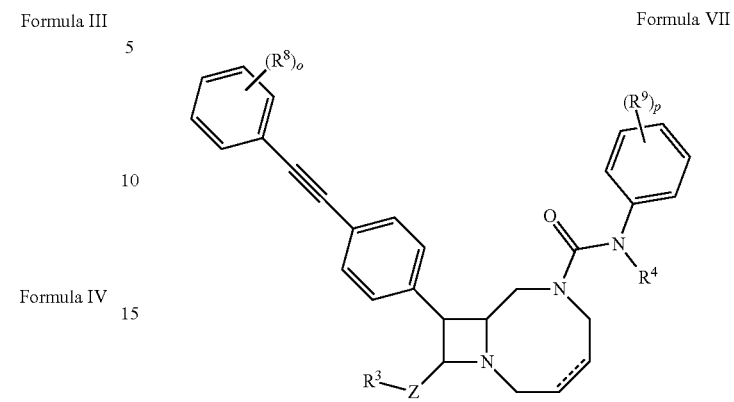

Formula VII wherein o and p are independently 1, 2, 3, 4, or 5; and $R^8$ and $R^9$ are independently hydrogen, halogen, or $C_1$-$C_6$ heteroalkyl.

In certain embodiments, —$ZR^3$ is hydrogen or —$CO_2H$. In some embodiments, Z is methylene. In other embodiments, $R^3$ is hydroxyl, $C_2$-$C_9$ heterocyclyl (e.g., 4-methylpiperazyl, 4-hydroxy-4-methyl-piperidyl, 3-hydroxyl-3-methyl-azetidinyl, or morpholinyl), —$OCH_2C(O)OH$, —$NH_2$, —$NHC(O)CH_3$, —$NHCH_3$, —$N(CH_3)_2$, or —$N(CH_3)C(O)CH_3$. In some embodiments, Z is $C_1$-$C_6$ heteroalkylene (e.g., —$CH_2OCH_2$— or —$CH_2OCH_2CH_2$—). In other embodiments, $R^3$ is —C(O) $R^7$ (e.g., wherein $R^7$ is hydroxyl, $C_1$-$C_6$ heteroalkyl such as methoxy, or $C_2$-$C_9$ heterocyclyl such as morpholino).

In certain embodiments, the compound of Formula VII has the stereochemistry of Formula IA or IB.

In certain embodiments, —$YR^2$ is —$CH_2CH_2CF_3$.

In some embodiments, Y is methylene or —$SO_2$—. In other embodiments, $R^2$ is 4-methoxy-phenyl.

In certain embodiments, $R^1$ is $C_2$-$C_9$ heteroaryl (e.g., 2-pyridyl or 3-pyridyl). In some embodiments, Y is —C(O) NH—. In other embodiments, $R^2$ is $C_6$-$C_{10}$ aryl (e.g., phenyl, 4-methoxy-phenyl, 2-fluoro-phenyl, or 3-fluoro-phenyl). In certain embodiments, —$ZR^3$ is hydrogen, —$CH_2OH$, —$CH_2NH_2$, or —$CH_2NHC(O)CH_3$. In some embodiments, Y is methylene. In other embodiments, $R^2$ is 3-methoxy-phenyl.

In certain embodiments, $R^1$ is iso-butyl, —$CH_2OCH_3$, cyclopropyl, cyclopentyl, or cyclohexyl. In some embodiments, Y is —C(O)NH—. In other embodiments, $R^2$ is 2-methoxy-phenyl or 4-methoxy-phenyl. In certain embodiments, Y is —$SO_2$—. In some embodiments, $R^2$ is 4-methoxy-phenyl or benzyl.

In other embodiments, X is absent.

In certain embodiments, $R^1$ is hydrogen, $C_6$-$C_{10}$ aryl (e.g., phenyl, 2-fluoro-phenyl, 3-fluorophenyl, 4-fluoro-phenyl, 3-methyl-phenyl, 4-methyl-phenyl), $C_3$-$C_{10}$ carbocyclyl (e.g., cyclohexenyl), $C_2$-$C_6$ heteroaryl (e.g., thiazolyl such as 2-phenyl-1,3-thiazol-4-yl, pyrrolyl such as 1-phenyl-pyrrol-3-yl, pyridyl such as 4-pyridyl, or pyrazolyl such as 1-phenyl-1H-pyrazol-3-yl).

In some embodiments, —$ZR^3$ is —$CH_2OH$.

In other embodiments, —$YR^2$ is —$CH_2CH_2CF_3$.

In certain embodiments, Y is —$SO_2$— and R is 3-methylphenyl or 4-fluoro-phenyl.

In some embodiments, Y is —C(O)NH— and $R^2$ is 4-methoxy-phenyl.

In another aspect, the invention features a compound selected from any one of compounds 31 to 95 of Table 1, or a pharmaceutically acceptable salt thereof.

TABLE 1

Selected Compounds of the Invention

| # | Structure | Name | Retention Time | LRMS (Calculated: Found) |
|---|---|---|---|---|
| 1 | 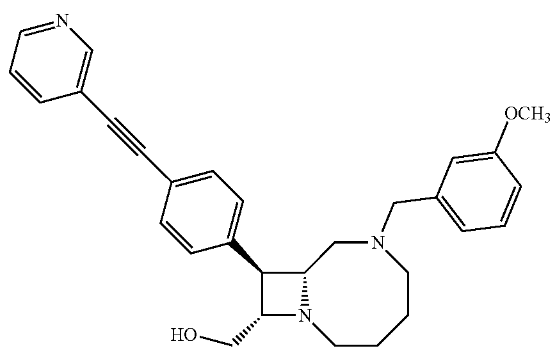 [SMILES: COc1cccc(CN2CCCCN3[C@H](CO)[C@@H](c4ccc(C#Cc5cccnc5)cc4)[C@@H]3C2)c1] | ((8R,9S,10S)-6-(3-methoxybenzyl)-9-(4-(pyridin-3-ylethynyl)phenyl)-1,6-diazabicyclo[6.2.0]decan-10-yl)methanol | Method A 0.85 | $C_{30}H_{34}N_3O_2$ [M + H]+ 468.26: 468.39 |
| 2 | 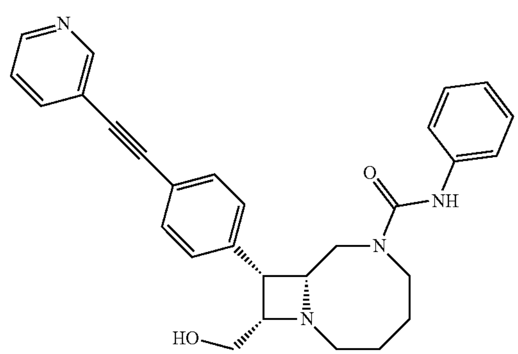 [SMILES: O=C(Nc1ccccc1)N1CCCCN2[C@H](CO)[C@H](c3ccc(C#Cc4cccnc4)cc3)[C@@H]2C1] | (8R,9R,10S)-10-(hydroxymethyl)-N-phenyl-9-(4-(pyridin-3-ylethynyl)phenyl)-1,6-diazabicyclo[6.2.0]decane-6-carboxamide | Method A 0.71 | $C_{29}H_{31}N_4O_2$ [M + H]+ 467.24: 467.57 |
| 3 | 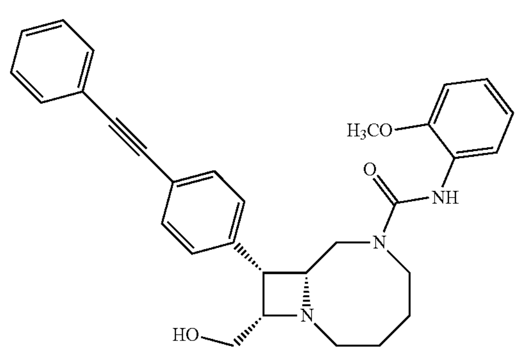 [SMILES: COc1ccccc1NC(=O)N1CCCCN2[C@H](CO)[C@H](c3ccc(C#Cc4ccccc4)cc3)[C@@H]2C1] | (8R,9R,10S)-10-(hydroxymethyl)-N-(2-methoxyphenyl)-9-(4-(phenylethynyl)phenyl)-1,6-diazabicyclo[6.2.0]decane-6-carboxamide | Method A 0.88 | $C_{31}H_{34}N_3O_3$ [M + H]+ 496.25: 496.58 |
| 4 | 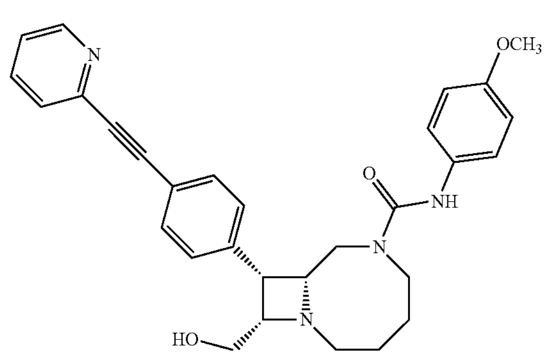 [SMILES: COc1ccc(NC(=O)N2CCCCN3[C@H](CO)[C@H](c4ccc(C#Cc5ccccn5)cc4)[C@@H]3C2)cc1] | (8R,9R,10S)-10-(hydroxymethyl)-N-(4-methoxyphenyl)-9-(4-(pyridin-2-ylethynyl)phenyl)-1,6-diazabicyclo[6.2.0]decane-6-carboxamide | Method A 0.69 | $C_{30}H_{32}N_4O_3$ [M + H]+ 497.25: 497.59 |

TABLE 1-continued

Selected Compounds of the Invention

| # | Structure | Name | Retention Time | LRMS (Calculated: Found) |
|---|---|---|---|---|
| 5 | 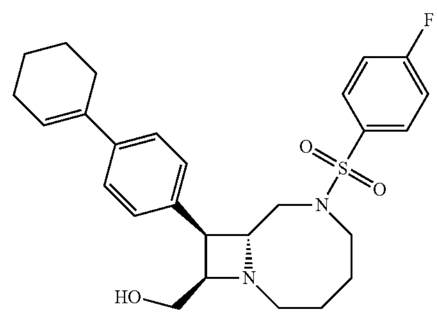 [SMILES: O=S(=O)(c1ccc(F)cc1)N1CCCCN2[C@@H](CO)[C@@H](c3ccc(C4=CCCCC4)cc3)[C@@H]2C1] | ((8R,9S,10R)-6-((4-fluorophenyl)sulfonyl)-9-(2',3',4',5'-tetrahydro-[1,1'-biphenyl]-4-yl)-1,6-diazabicyclo[6.2.0]decan-10-yl)methanol | Method A 0.88 | $C_{27}H_{34}FN_2$ [M + H]+ 485.22: 485.49 |
| 6 | 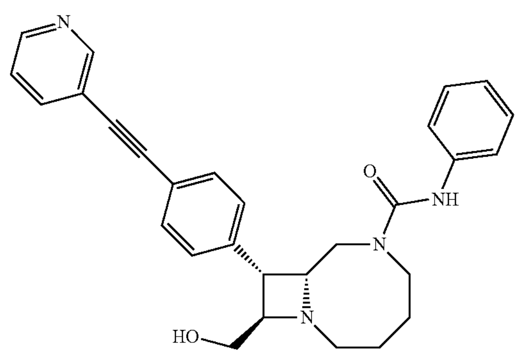 [SMILES: O=C(Nc1ccccc1)N1CCCCN2[C@@H](CO)[C@H](c3ccc(C#Cc4cccnc4)cc3)[C@@H]2C1] | (8R,9R,10R)-10-(hydroxymethyl)-N-phenyl-9-(4-(pyridin-3-ylethynyl)phenyl)-1,6-diazabicyclo[6.2.0]decane-6-carboxamide | Method A 0.70 | $C_{29}H_{31}N_4O_2$ [M − H]− 465.24: 465.27 |
| 7 | 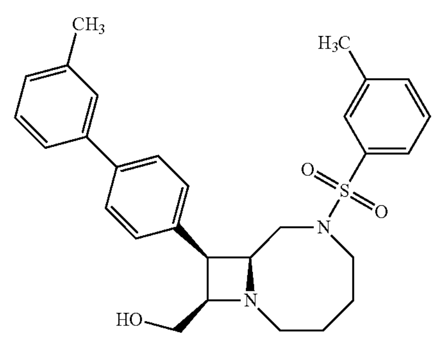 [SMILES: Cc1cccc(-c2ccc([C@H]3[C@H]4CN(S(=O)(=O)c5cccc(C)c5)CCCCN4[C@H]3CO)cc2)c1] | ((8S,9S,10R)-9-(3'-methyl-[1,1'-biphenyl]-4-yl)-6-(m-tolylsulfonyl)-1,6-diazabicyclo[6.2.0]decan-10-yl)methanol | Method A 0.91 | $C_{29}H_{35}N_2O_3S$ [M + H]+ 491.229: 491.50 |
| 8 | 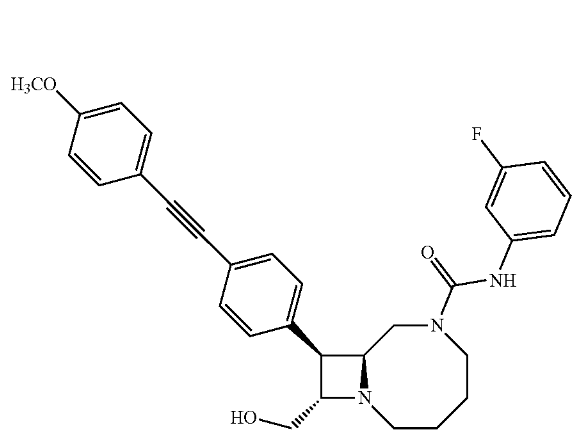 [SMILES: COc1ccc(C#Cc2ccc([C@@H]3[C@@H](CO)N4CCCCN(C(=O)Nc5cccc(F)c5)C[C@H]34)cc2)cc1] | (8S,9S,10S)-N-(3-fluorophenyl)-10-(hydroxymethyl)-9-(4-((4-methoxyphenyl)ethynyl)phenyl)-1,6-diazabicyclo[6.2.0]decane-6-carboxamide | Method A 0.85 | $C_{31}H_{33}FN_3O_3$ [M + H]+ 514.243: 514.44 |

TABLE 1-continued

Selected Compounds of the Invention

| # | Structure | Name | Retention Time | LRMS (Calculated: Found) |
|---|---|---|---|---|
| 9 | 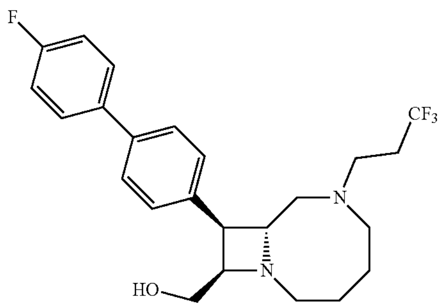 [SMILES: OC[C@H]1[C@@H](c2ccc(-c3ccc(F)cc3)cc2)[C@@H]2CN(CCC(F)(F)F)CCCCN12] | ((8R,9S,10R)-9-(4'-fluoro-[1,1'-biphenyl]-4-yl)-6-(3,3,3-trifluoropropyl)-1,6-diazabicyclo[6.2.0]decan-10-yl)methanol | Method A 0.83 | $C_{24}H_{29}F_4N_2O$ [M + H]+ 437.214: 437.40 |
| 10 | 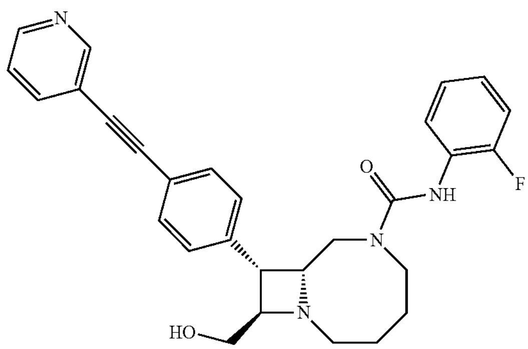 [SMILES: O=C(Nc1ccccc1F)N1CCCCN2[C@@H](CO)[C@H](c3ccc(C#Cc4cccnc4)cc3)[C@@H]2C1] | (8R,9R,10R)-N-(2-fluorophenyl)-10-(hydroxymethyl)-9-(4-(pyridin-3-ylethynyl)phenyl)-1,6-diazabicyclo[6.2.0]decane-6-carboxamide | Method A 0.71 | $C_{29}H_{30}FN_4O_2$ [M + H]+ 485.227: 485.42 |
| 11 | 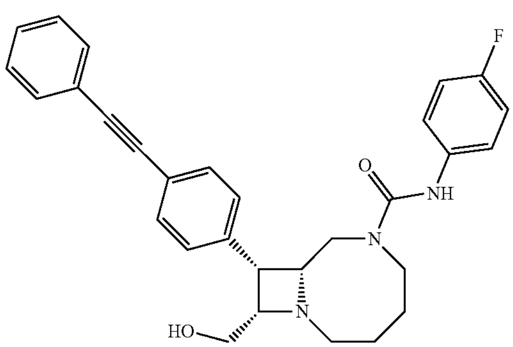 [SMILES: O=C(Nc1ccc(F)cc1)N1CCCCN2[C@H](CO)[C@H](c3ccc(C#Cc4ccccc4)cc3)[C@@H]2C1] | (8R,9R,10S)-N-(4-fluorophenyl)-10-(hydroxymethyl)-9-(4-(phenylethynyl)phenyl)-1,6-diazabicyclo[6.2.0]decane-6-carboxamide | Method A 0.84 | $C_{30}H_{31}FN_3O_2$ [M + H]+ 484.23: 484.42 |
| 12 | 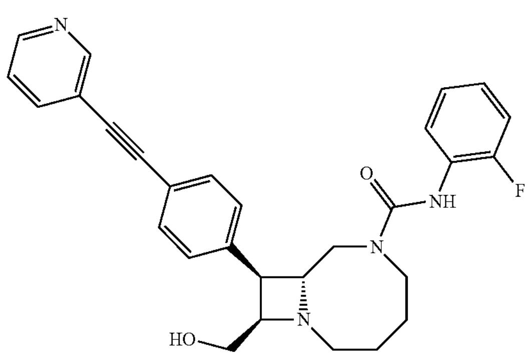 [SMILES: O=C(Nc1ccccc1F)N1CCCCN2[C@@H](CO)[C@@H](c3ccc(C#Cc4cccnc4)cc3)[C@@H]2C1] | (8R,9S,10R)-N-(2-fluorophenyl)-10-hydroxymethyl)-9-(4-(pyridin-3-ylethynyl)phenyl)-1,6-diazabicyclo[6.2.0]decane-6-carboxamide | Method A 0.69 | $C_{29}H_{30}FN_4O_2$ [M + H]+ 485.23: 485.46 |

TABLE 1-continued

Selected Compounds of the Invention

| # | Structure | Name | Retention Time | LRMS (Calculated: Found) |
|---|---|---|---|---|
| 13 | 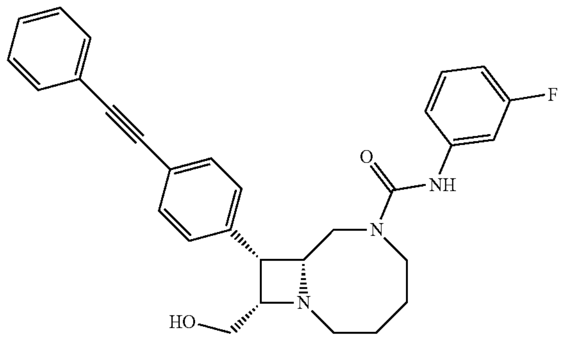 [SMILES: O=C(Nc1cccc(F)c1)N1CCCCN2[C@H](CO)[C@H](c3ccc(C#Cc4ccccc4)cc3)[C@@H]2C1] | (8R,9R,10S)-N-(3-fluorophenyl)-10-(hydroxymethyl)-9-(4-(phenylethynyl)phenyl)-1,6-diazabicyclo[6.2.0]decane-6-carboxamide | Method A 0.85 | $C_{30}H_{31}FN_3O_2$ [M + H]+ 484.23: 484.56 |
| 14 | 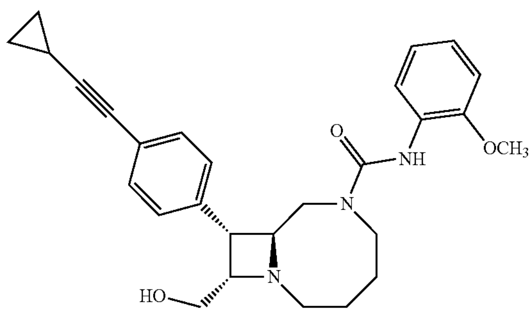 [SMILES: COc1ccccc1NC(=O)N1CCCCN2[C@H](CO)[C@H](c3ccc(C#CC4CC4)cc3)[C@H]2C1] | (8S,9R,10S)-9-(4-(cyclopropylethynyl)phenyl)-10-(hydroxymethyl)-N-(2-methoxyphenyl)-1,6-diazabicyclo[6.2.0]decane-6-carboxamide | Method A 0.78 | $C_{28}H_{34}N_3O_3$ [M + 2H]+ 461.25: 461.62 |
| 15 | 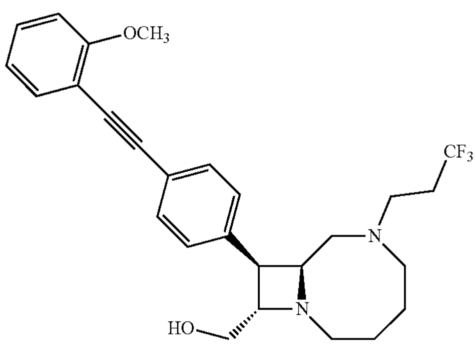 [SMILES: COc1ccccc1C#Cc1ccc([C@@H]2[C@@H](CO)N3CCCCN(CCC(F)(F)F)C[C@H]23)cc1] | ((8S,9S,10S)-9-(4-((2-methoxyphenyl)ethynyl)phenyl)-6-(3,3,3-trifluoropropyl)-1,6-diazabicyclo[6.2.0]decan-10-yl)methanol | Method A 0.84 | $C_{27}H_{32}F_3N_2O_2$ [M + H]+ 473.23: 473.37 |
| 16 | 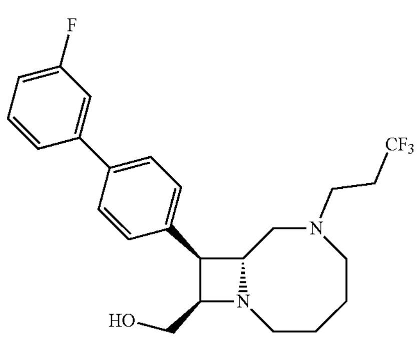 [SMILES: OC[C@H]1[C@@H](c2ccc(-c3cccc(F)c3)cc2)[C@@H]2CN(CCC(F)(F)F)CCCCN12] | ((8R,9S,10R)-9-(3'-fluoro-[1,1'-biphenyl]-4-yl)-6-(3,3,3-trifluoropropyl)-1,6-diazabicyclo[6.2.0]decan-10-yl)methanol | Method A 0.83 | $C_{24}H_{29}F_4N_2O$ [M + H]+ 437.21: 437.32 |

TABLE 1-continued

Selected Compounds of the Invention

| # | Structure | Name | Retention Time | LRMS (Calculated: Found) |
|---|---|---|---|---|
| 17 | 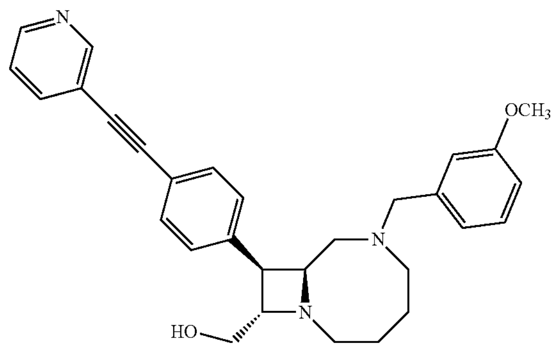 [SMILES: COc1cccc(CN2CCCCN3[C@H](CO)[C@@H](c4ccc(C#Cc5cccnc5)cc4)[C@H]3C2)c1] | ((8S,9S,10S)-6-(3-methoxybenzyl)-9-(4-(pyridin-3-ylethynyl)phenyl)-1,6-diazabicyclo[6.2.0]decan-10-yl)methanol | Method A 0.75 | $C_{30}H_{34}N_3O_2$ [M + H]+ 468.26: 468.41 |
| 18 | 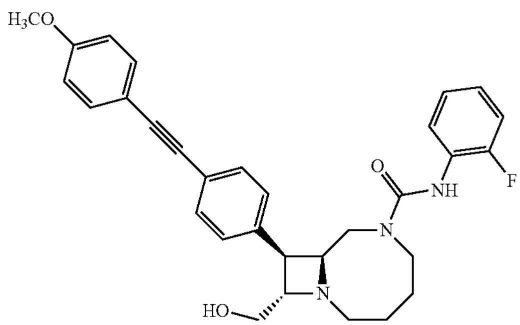 [SMILES: COc1ccc(C#Cc2ccc([C@@H]3[C@@H](CO)N4CCCCN(C(=O)Nc5ccccc5F)C[C@H]34)cc2)cc1] | (8S,9S,10S)-N-(2-fluorophenyl)-10-(hydroxymethyl)-9-(4-((4-methoxyphenyl)ethynyl)phenyl)-1,6-diazabicyclo[6.2.0]decane-6-carboxamide | Method A 0.83 | $C_{31}H_{33}FN_3O_3$ [M + H]+ 514.24: 514.60 |
| 19 | 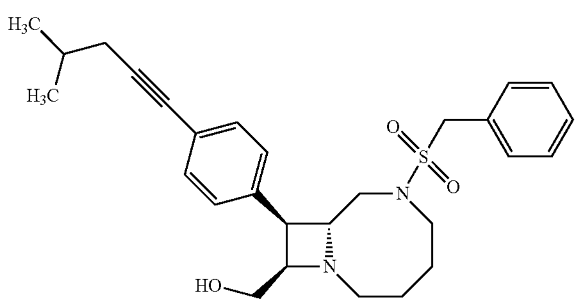 [SMILES: CC(C)CC#Cc1ccc([C@@H]2[C@H](CO)N3CCCCN(S(=O)(=O)Cc4ccccc4)C[C@@H]23)cc1] | ((8R,9S,10R)-6-(benzylsulfonyl)-9-(4-(4-methylpent-1-yn-1-yl)phenyl)-1,6-diazabicyclo[6.2.0]decan-10-yl)methanol | Method A 0.86 | $C_{28}H_{37}N_2O_3S$ [M + H]+ 481.245: 481.46 |
| 20 | 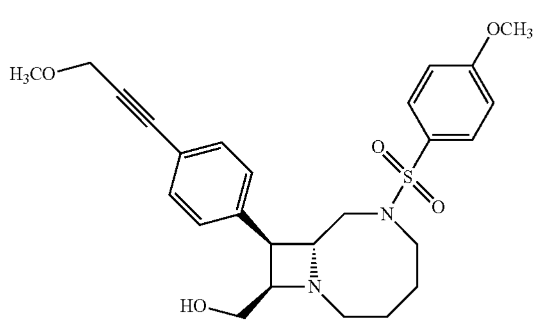 [SMILES: COCC#Cc1ccc([C@@H]2[C@H](CO)N3CCCCN(S(=O)(=O)c4ccc(OC)cc4)C[C@@H]23)cc1] | ((8R,9S,10R)-6-((4-methoxyphenyl)sulfonyl)-9-(4-(3-methoxyprop-1-yn-1-yl)phenyl)-1,6-diazabicyclo[6.2.0]decan-10-yl)methanol | Method A 0.73 | $C_{26}H_{33}N_2O_5S$ [M + H]+ 485.20: 485.38 |

TABLE 1-continued

Selected Compounds of the Invention

| # | Structure | Name | Retention Time | LRMS (Calculated: Found) |
|---|---|---|---|---|
| 21 | 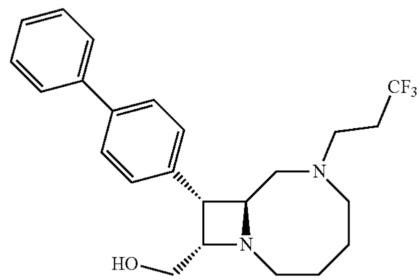 [SMILES: OC[C@@H]1[C@H](c2ccc(-c3ccccc3)cc2)[C@H]2CN(CCC(F)(F)F)CCCCN12] | ((8S,9R,10S)-9-([1,1'-biphenyl]-4-yl)-6-(3,3,3-trifluoropropyl)-1,6-diazabicyclo[6.2.0]decan-10-yl)methanol | Method A 0.8 | C$_{24}$H$_{30}$F$_3$N$_2$O [M + H]+ 419.22: 419.28 |
| 22 | 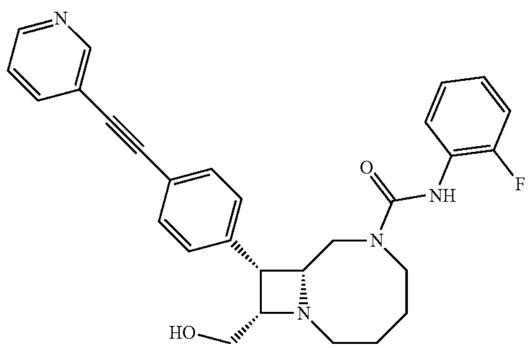 [SMILES: O=C(Nc1ccccc1F)N1CCCCN2[C@H](CO)[C@H](c3ccc(C#Cc4cccnc4)cc3)[C@@H]2C1] | (8R,9R,10S)-N-(2-fluorophenyl)-10-(hydroxymethyl)-9-(4-(pyridin-3-ylethynyl)phenyl)-1,6-diazabicyclo[6.2.0]decane-6-carboxamide | Method A 0.72 | C$_{29}$H$_{30}$FN$_4$O$_2$ [M + H]+ 485.23: 485.47 |
| 23 | 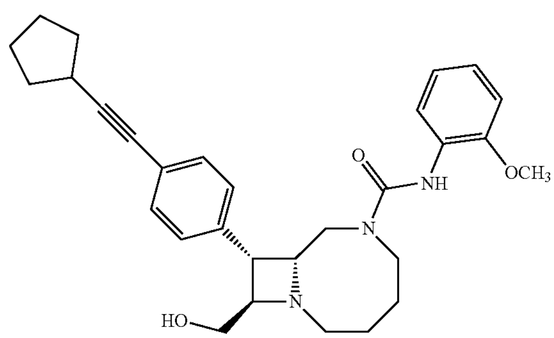 [SMILES: COc1ccccc1NC(=O)N1CCCCN2[C@@H](CO)[C@H](c3ccc(C#CC4CCCC4)cc3)[C@@H]2C1] | (8R,9R,10R)-9-(4-(cyclopentylethynyl)phenyl)-10-(hydroxymethyl)-N-(2-methoxyphenyl)-1,6-diazabicyclo[6.2.0]decane-6-carboxamide | Method A 0.91 | C$_{30}$H$_{38}$N$_3$O$_3$ [M + H]+ 488.28: 488.42 |
| 24 | 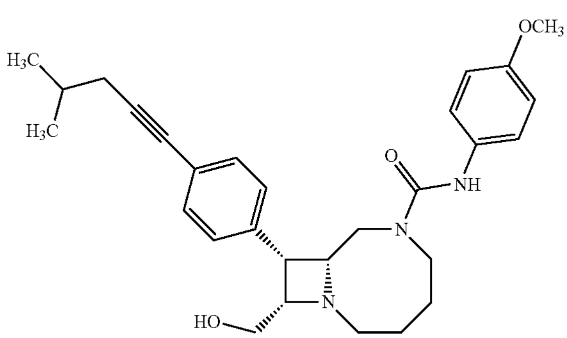 [SMILES: COc1ccc(NC(=O)N2CCCCN3[C@H](CO)[C@H](c4ccc(C#CCC(C)C)cc4)[C@@H]3C2)cc1] | (8R,9R,10S)-10-(hydroxymethyl)-N-(4-methoxyphenyl)-9-(4-(4-methylpent-1-yn-1-yl)phenyl)-1,6-diazabicyclo[6.2.0]decane-6-carboxamide | Method A 0.84 | C$_{29}$H$_{38}$N$_3$O$_3$ [M + H]+ 476.28: 476.48 |

TABLE 1-continued

Selected Compounds of the Invention

| # | Structure | Name | Retention Time | LRMS (Calculated: Found) |
|---|---|---|---|---|
| 25 | 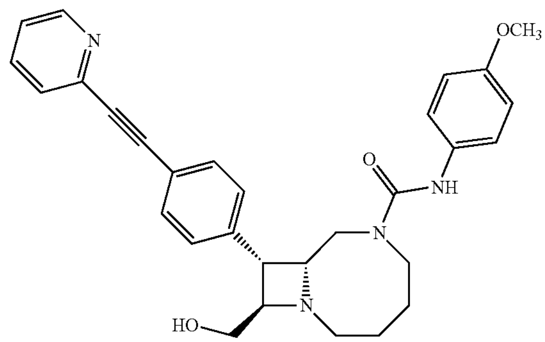 [SMILES: COc1ccc(NC(=O)N2CCCCN3[C@@H](CO)[C@H](c4ccc(C#Cc5ccccn5)cc4)[C@@H]3C2)cc1] | (8R,9R,10R)-10-(hydroxymethyl)-N-(4-methoxyphenyl)-9-(4-(pyridin-2-ylethynyl)phenyl)-1,6-diazabicyclo[6.2.0]decane-6-carboxamide | Method A 0.68 | $C_{30}H_{33}N_4O_3$ [M + H]+ 497.25: 497.55 |
| 26 | 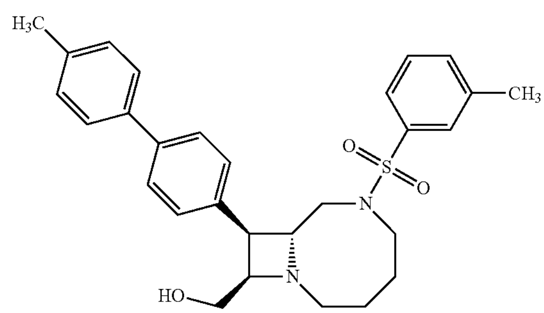 | ((8R,9S,10R)-9-(4'-methyl-[1,1'-biphenyl]-4-yl)-6-(m-tolylsulfonyl)-1,6-diazabicyclo[6.2.0]decan-10-yl)methanol | Method A 0.87 | $C_{29}H_{35}N_2O_3S$ [M + H]+ 491.23: 491.44 |
| 27 | 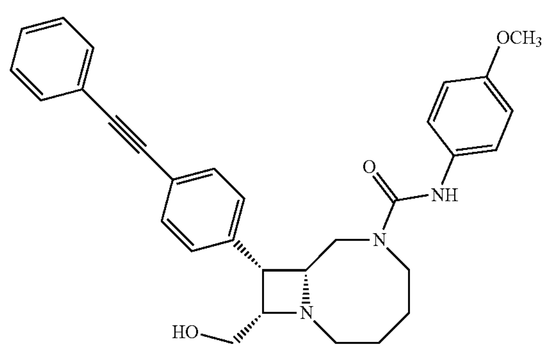 [SMILES: COc1ccc(NC(=O)N2CCCCN3[C@H](CO)[C@H](c4ccc(C#Cc5ccccc5)cc4)[C@@H]3C2)cc1] | (8R,9R,10S)-10-(hydroxymethyl)-N-(4-methoxyphenyl)-9-(4-(phenylethynyl)phenyl)-1,6-diazabicyclo[6.2.0]decane-6-carboxamide | Method A 0.83 | $C_{31}H_{34}N_3O_3$ [M + H]+ 496.25: 496.48 |
| 28 | 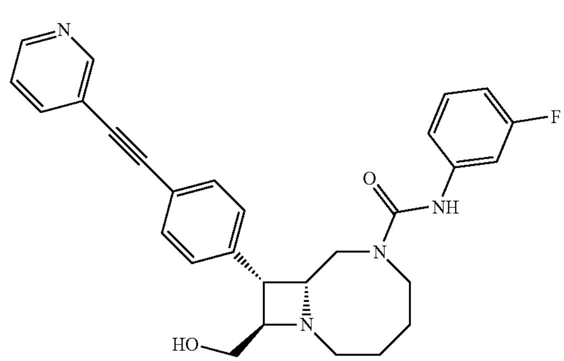 [SMILES: O=C(Nc1cccc(F)c1)N1CCCCN2[C@@H](CO)[C@H](c3ccc(C#Cc4cccnc4)cc3)[C@@H]2C1] | (8R,9R,10R)-N-(3-fluorophenyl)-10-(hydroxymethyl)-9-(4-(pyridin-3-ylethynyl)phenyl)-1,6-diazabicyclo[6.2.0]decane-6-carboxamide | Method A 0.72 | $C_{29}H_{30}FN_4O_2$ [M + H]+ 485.23: 485.50 |

TABLE 1-continued

Selected Compounds of the Invention

| # | Structure | Name | Retention Time | LRMS (Calculated: Found) |
|---|---|---|---|---|
| 29 | 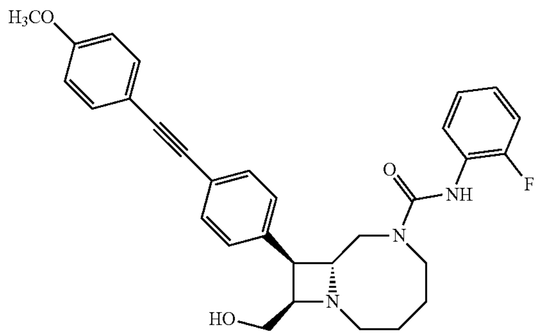 [SMILES: COc1ccc(C#Cc2ccc([C@@H]3[C@H](CO)N4CCCCN(C(=O)Nc5ccccc5F)C[C@@H]34)cc2)cc1] | (8R,9S,10R)-N-(2-fluorophenyl)-10-(hydroxymethyl)-9-(4-((4-methoxyphenyl)ethynyl)phenyl)-1,6-diazabicyclo[6.2.0]decane-6-carboxamide | Method A 0.80 | $C_{31}H_{33}FN_3O_3$ [M + H]+ 514.24: 514.35 |
| 30 | 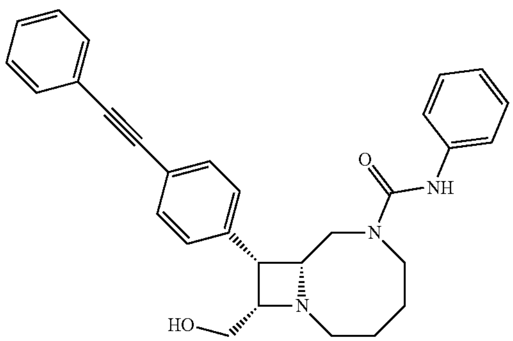 [SMILES: O=C(Nc1ccccc1)N1CCCCN2[C@H](CO)[C@H](c3ccc(C#Cc4ccccc4)cc3)[C@@H]2C1] | (8R,9R,10S)-10-(hydroxymethyl)-N-phenyl-9-(4-(phenylethynyl)phenyl)-1,6-diazabicyclo[6.2.0]decane-6-carboxamide | Method A 0.83 | $C_{30}H_{32}N_3O_2$ [M + H]+ 466.24: 466.5 |
| 31 | 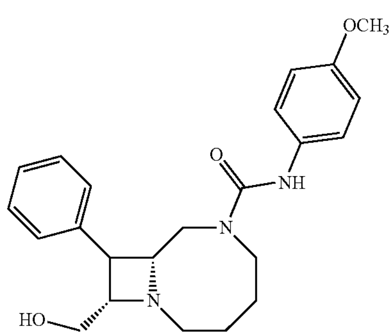 | (8R,10S)-10-(hydroxymethyl)-N-(4-methoxyphenyl)-9-phenyl-1,6-diazabicyclo[6.2.0]decane-6-carboxamide | Method A 0.67 | $C_{23}H_{30}N_3O_3$ [M + H]+ 396.22: 396.43 |
| 32 | 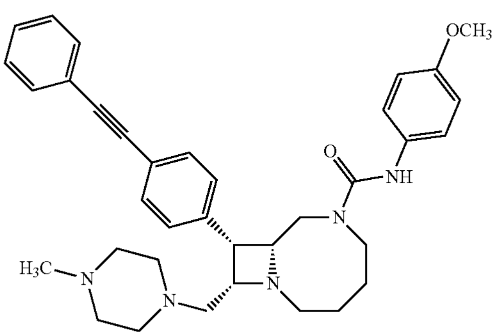 [SMILES: COc1ccc(NC(=O)N2CCCCN3[C@H](CN4CCN(C)CC4)[C@H](c4ccc(C#Cc5ccccc5)cc4)[C@@H]3C2)cc1] | (8R,9S,10S)-N-(4-methoxyphenyl)-10-[(4-methylpiperazin-1-yl)methyl]-9-[4-(2-phenylethynyl)phenyl]-1,6-diazabicyclo[6.2.0]decane-6-carboxamide | Method A 0.59 | $C_{36}H_{44}N_5O_2$ [M + H]+ 578.34: 578.55 |

TABLE 1-continued

Selected Compounds of the Invention

| # | Structure | Name | Retention Time | LRMS (Calculated: Found) |
|---|---|---|---|---|
| 33 | 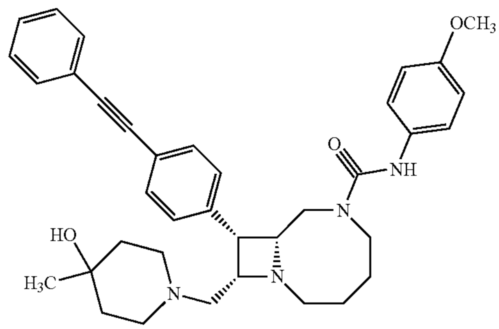 | (8R,9S,10S)-10-[(4-hydroxy-4-methylpiperidin-1-yl)methyl]-N-(4-methoxyphenyl)-9-[4-(2-phenylethynyl)phenyl]-1,6-diazabicyclo[6.2.0]decane-6-carboxamide | Method A 0.89 | $C_{37}H_{45}N_4O_3$ [M + H]+ 593.34: 593.57 |
| 34 | 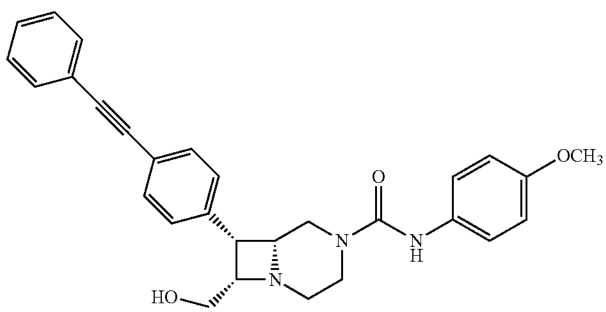 [SMILES: COc1ccc(NC(=O)N2CCN3[C@H](CO)[C@H](c4ccc(C#Cc5ccccc5)cc4)[C@@H]3C2)cc1] | (6R,7R,8S)-8-(hydroxymethyl)-N-(4-methoxyphenyl)-7-[4-(2-phenylethynyl)phenyl]-1,4-diazabicyclo[4.2.0]octane-4-carboxamide | Method A 0.79 | $C_{29}H_{30}N_3O_3$ [M + H]+ 468.22: 468.46 |
| 35 | 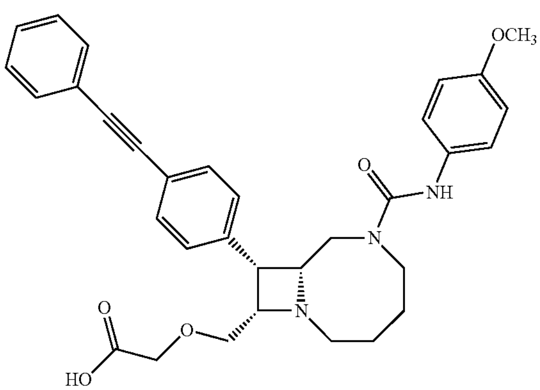 [SMILES: COc1ccc(NC(=O)N2CCCCN3[C@H](COCC(=O)O)[C@H](c4ccc(C#Cc5ccccc5)cc4)[C@@H]3C2)cc1] | 2-{[(8R,9R,10S)-6-[(4-methoxyphenyl)carbamoyl]-9-[4-(2-phenylethynyl)phenyl]-1,6-diazabicyclo[6.2.0]decan-10-yl]methoxy}acetic acid | Method A 0.48 | $C_{33}H_{36}N_3O_5$ [M + H]+ 554.26: 554.14 |
| 36 | 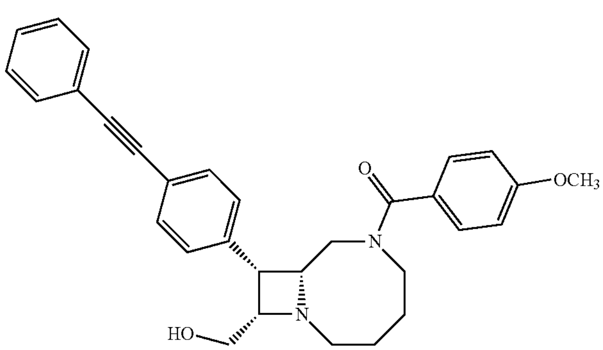 [SMILES: COc1ccc(C(=O)N2CCCCN3[C@H](CO)[C@H](c4ccc(C#Cc5ccccc5)cc4)[C@@H]3C2)cc1] | [(8R,9R,10S)-6-(4-methoxybenzoyl)-9-[4-(2-phenylethynyl)phenyl]-1,6-diazabicyclo[6.2.0]decan-10-yl]methanol | Method A 0.84 | $C_{31}H_{33}N_2O_3$ [M + H]+ 481.24: 481.45 |

TABLE 1-continued

Selected Compounds of the Invention

| # | Structure | Name | Retention Time | LRMS (Calculated: Found) |
|---|---|---|---|---|
| 37 | 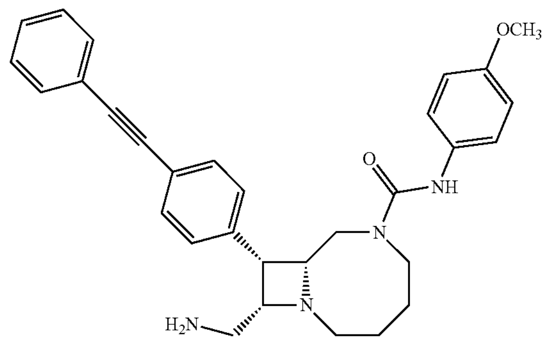 [SMILES: COc1ccc(NC(=O)N2CCCCN3[C@H](CN)[C@H](c4ccc(C#Cc5ccccc5)cc4)[C@@H]3C2)cc1] | (8R,9S,10S)-10-(aminomethyl)-N-(4-methoxyphenyl)-9-[4-(2-phenylethynyl)phenyl]-1,6-diazabicyclo[6.2.0]decane-6-carboxamide | Method A 0.84 | $C_{31}H_{35}N_4O_2$ [M + H]+ 495.27: 495.49 |
| 38 | 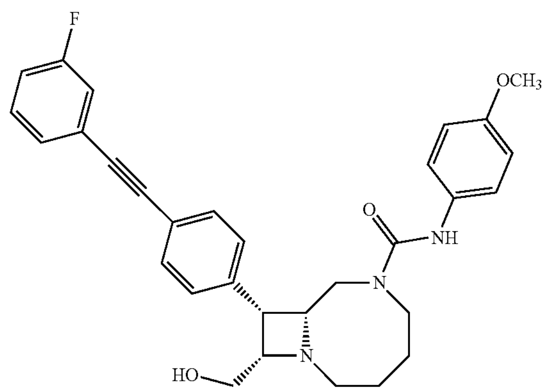 [SMILES: COc1ccc(NC(=O)N2CCCCN3[C@H](CO)[C@H](c4ccc(C#Cc5cccc(F)c5)cc4)[C@@H]3C2)cc1] | (8R,9R,10S)-9-{4-[2-(3-fluorophenyl)ethynyl]phenyl}-10-(hydroxymethyl)-N-(4-methoxyphenyl)-1,6-diazabicyclo[6.2.0]decane-6-carboxamide | Method A 0.83 | $C_{31}H_{33}FN_3O_3$ [M + H]+ 514.24: 514.49 |
| 39 | 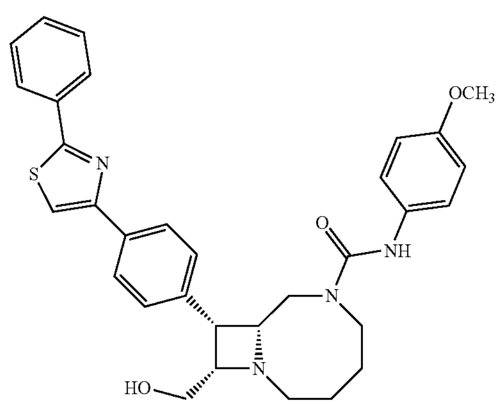 [SMILES: COc1ccc(NC(=O)N2CCCCN3[C@H](CO)[C@H](c4ccc(-c5csc(-c6ccccc6)n5)cc4)[C@@H]3C2)cc1] | (8R,9R,10S)-10-(hydroxymethyl)-N-(4-methoxyphenyl)-9-[4-(2-phenyl-1,3-thiazol-4-yl)phenyl]-1,6-diazabicyclo[6.2.0]decane-6-carboxamide | Method A 0.84 | $C_{32}H_{35}N_4O_3S$ 554.235: 553.47 |
| 40 | 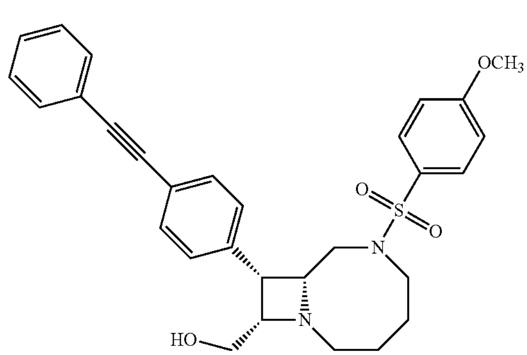 [SMILES: COc1ccc(S(=O)(=O)N2CCCCN3[C@H](CO)[C@H](c4ccc(C#Cc5ccccc5)cc4)[C@@H]3C2)cc1] | [(8R,9R,10S)-6-(4-methoxybenzene-sulfonyl)-9-[4-(2-phenylethynyl)phenyl]-1,6-diazabicyclo[6.2.0]decan-10-yl]methanol | Method A 0.88 | $C_{30}H_{33}N_2O_4S$ [M + H]+ 517.21: 517.46 |

TABLE 1-continued

Selected Compounds of the Invention

| # | Structure | Name | Retention Time | LRMS (Calculated: Found) |
|---|---|---|---|---|
| 41 | 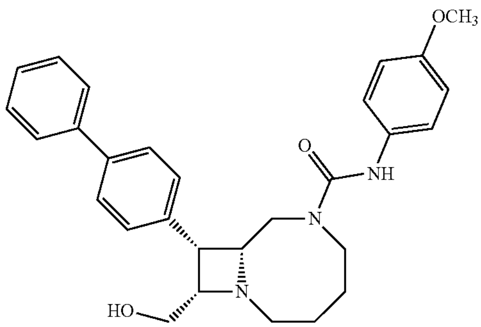 [SMILES: COc1ccc(NC(=O)N2CCCCN3[C@H](CO)[C@H](c4ccc(-c5ccccc5)cc4)[C@@H]3C2)cc1] | (8R,9R,10S)-10-(hydroxymethyl)-N-(4-methoxyphenyl)-9-(4-phenylphenyl)-1,6-diazabicyclo[6.2.0]decane-6-carboxamide | Method A 0.78 | $C_{29}H_{34}N_3O_3$ [M + H]+ 472.25: 472.49 |
| 42 | 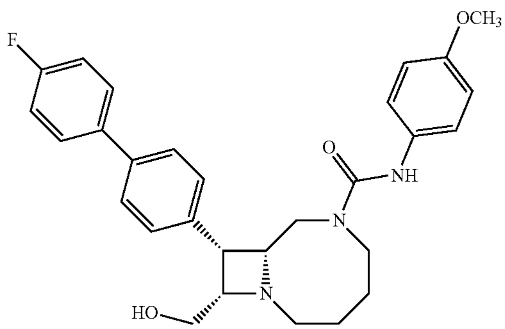 [SMILES: COc1ccc(NC(=O)N2CCCCN3[C@H](CO)[C@H](c4ccc(-c5ccc(F)cc5)cc4)[C@@H]3C2)cc1] | (8R,9R,10S)-9-[4-(4-fluorophenyl)phenyl]-10-(hydroxymethyl)-N-(4-methoxyphenyl)-1,6-diazabicyclo[6.2.0]decane-6-carboxamide | Method A 0.78 | $C_{29}H_{33}FN_3O_3$ [M + H]+ 490.243: 490.49 |
| 43 | 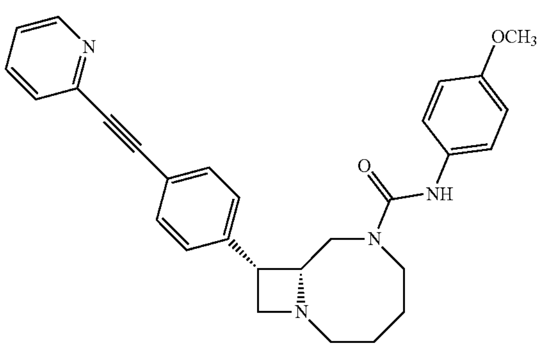 [SMILES: COc1ccc(NC(=O)N2CCCCN3C[C@H](c4ccc(C#Cc5ccccn5)cc4)[C@@H]3C2)cc1] | (8R,9S)-N-(4-methoxyphenyl)-9-{4-[2-(pyridin-2-yl)ethynyl]phenyl}-1,6-diazabicyclo[6.2.0]decane-6-carboxamide | Method A 0.79 | $C_{29}H_{31}N_4O_2$ [M + H]+ 467.237: 467.43 |
| 44 | 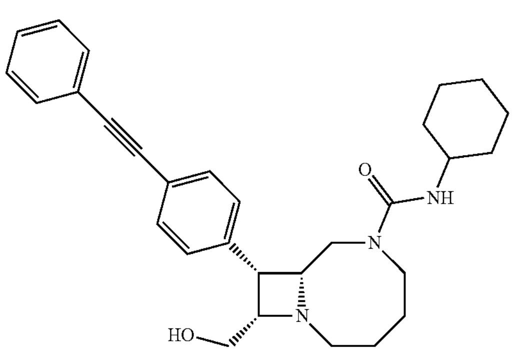 [SMILES: O=C(NC1CCCCC1)N1CCCCN2[C@H](CO)[C@H](c3ccc(C#Cc4ccccc4)cc3)[C@@H]2C1] | (8R,9R,10S)-N-cyclohexyl-10-(hydroxymethyl)-9-[4-(2-phenylethynyl)phenyl]-1,6-diazabicyclo[6.2.0]decane-6-carboxamide | Method A 0.88 | $C_{30}H_{38}N_3O_2$ [M + H]+ 472.289: 472.50 |

TABLE 1-continued

Selected Compounds of the Invention

| # | Structure | Name | Retention Time | LRMS (Calculated: Found) |
|---|-----------|------|----------------|--------------------------|
| 45 | 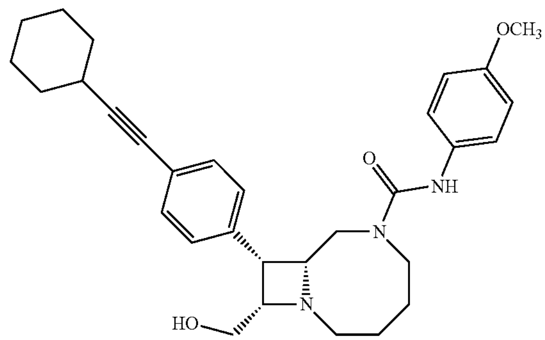 [SMILES: COc1ccc(NC(=O)N2CCCCN3[C@H](CO)[C@H](c4ccc(C#CC5CCCCC5)cc4)[C@@H]3C2)cc1] | (8R,9R,10S)-9-[4-(2-cyclohexylethynyl)phenyl]-10-(hydroxymethyl)-N-(4-methoxyphenyl)-1,6-diazabicyclo[6.2.0]decane-6-carboxamide | Method A 0.90 | $C_{31}H_{40}N_3O_3$ [M + H]+ 502.299: 502.49 |
| 46 | 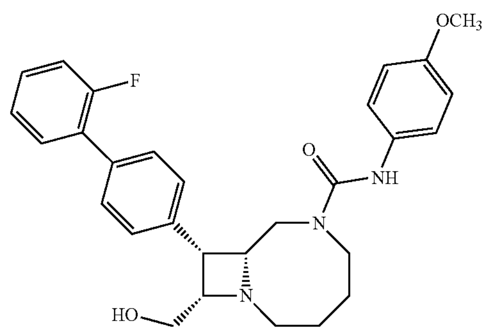 [SMILES: COc1ccc(NC(=O)N2CCCCN3[C@H](CO)[C@H](c4ccc(-c5ccccc5F)cc4)[C@@H]3C2)cc1] | (8R,9R,10S)-9-[4-(2-fluorophenyl)phenyl]-10-(hydroxymethyl)-N-(4-methoxyphenyl)-1,6-diazabicyclo[6.2.0]decane-6-carboxamide | Method A 0.78 | $C_{29}H_{33}FN_3O_3$ [M + H]+ 490.24: 490.49 |
| 47 | 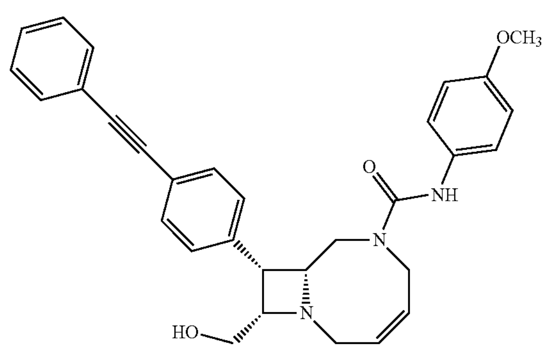 [SMILES: COc1ccc(NC(=O)N2C/C=C\CN3[C@H](CO)[C@H](c4ccc(C#Cc5ccccc5)cc4)[C@@H]3C2)cc1] | (8R,9R,10S)-10-(hydroxymethyl)-N-(4-methoxyphenyl)-9-[4-(2-phenylethynyl)phenyl]-1,6-diazabicyclo[6.2.0]dec-3-ene-6-carboxamide | Method A 0.80 | $C_{31}H_{32}N_3O_3$ [M + H]+ 494.24: 494.22 |
| 48 | 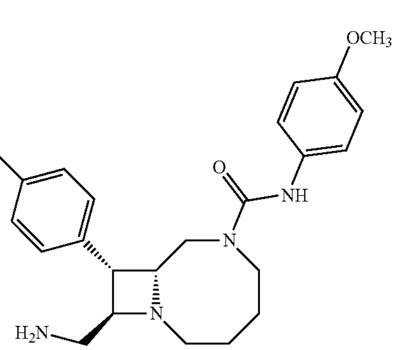 | (8R,9S,10R)-10-(aminomethyl)-N-(4-methoxyphenyl)-9-[4-(2-phenylethynyl)phenyl]-1,6-diazabicyclo[6.2.0]decane-6-carboxamide | Method A 0.81 | $C_{31}H_{35}N_4O_2$ [M + H]+ 495.27: 495.21 |

TABLE 1-continued

Selected Compounds of the Invention

| # | Structure | Name | Retention Time | LRMS (Calculated: Found) |
|---|---|---|---|---|
| 49 | 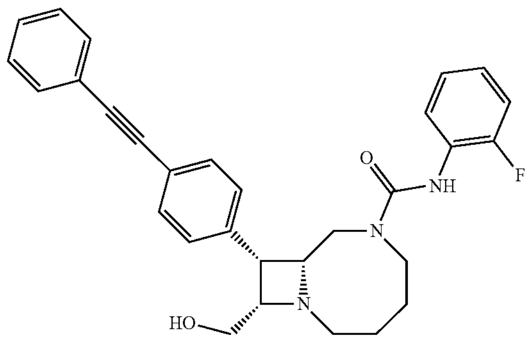 [SMILES: O=C(Nc1ccccc1F)N1CCCCN2[C@H](CO)[C@H](c3ccc(C#Cc4ccccc4)cc3)[C@@H]2C1] | (8R,9R,10S)-N-(2-fluorophenyl)-10-(hydroxymethyl)-9-[4-(2-phenylethynyl)phenyl]-1,6-diazabicyclo[6.2.0]decane-6-carboxamide | Method A 0.86 | $C_{30}H_{31}FN_3O_2$ [M + H]+ 484.23: 484.46 |
| 50 | 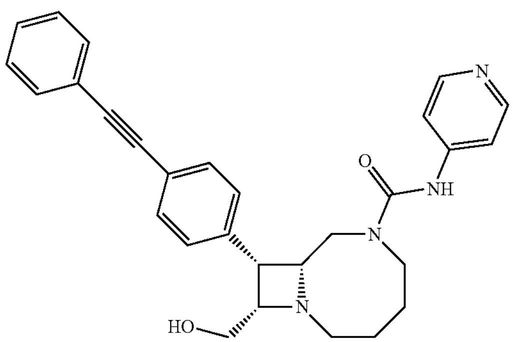 | (8R,9R,10S)-10-(hydroxymethyl)-9-[4-(2-phenylethynyl)phenyl]-N-(pyridin-4-yl)-1,6-diazabicyclo[6.2.0]decane-6-carboxamide | Method A 0.76 | $C_{29}H_{30}N_4O_2$ [M − H]− 466.237: 465.39 |
| 51 | 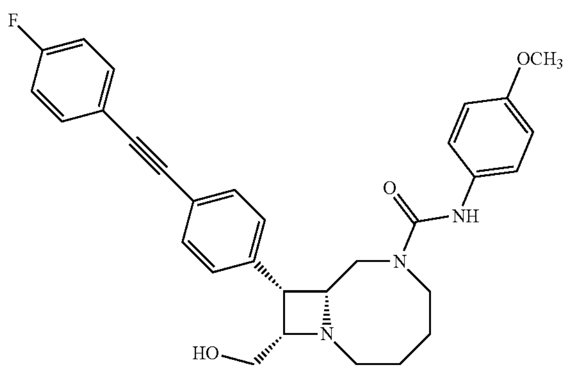 [SMILES: COc1ccc(NC(=O)N2CCCCN3[C@H](CO)[C@H](c4ccc(C#Cc5ccc(F)cc5)cc4)[C@@H]3C2)cc1] | (8R,9R,10S)-9-{4-[2-(4-fluorophenyl)ethynyl]phenyl}-10-(hydroxymethyl)-N-(4-methoxyphenyl)-1,6-diazabicyclo[6.2.0]decane-6-carboxamide | Method A 0.83 | $C_{31}H_{33}FN_3O_3$ [M + H]+ 514.24: 514.49 |
| 52 | 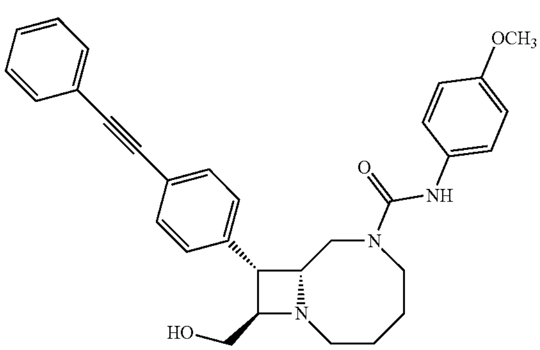 [SMILES: COc1ccc(NC(=O)N2CCCCN3[C@@H](CO)[C@H](c4ccc(C#Cc5ccccc5)cc4)[C@@H]3C2)cc1] | (8R,9R,10R)-10-(hydroxymethyl)-N-(4-methoxyphenyl)-9-[4-(2-phenylethynyl)phenyl]-1,6-diazabicyclo[6.2.0]decane-6-carboxamide | Method A 0.83 | $C_{31}H_{33}N_3O_3$ [M + H]+ 496.25: 496.47 |

TABLE 1-continued

Selected Compounds of the Invention

| # | Structure | Name | Retention Time | LRMS (Calculated: Found) |
|---|---|---|---|---|
| 53 | 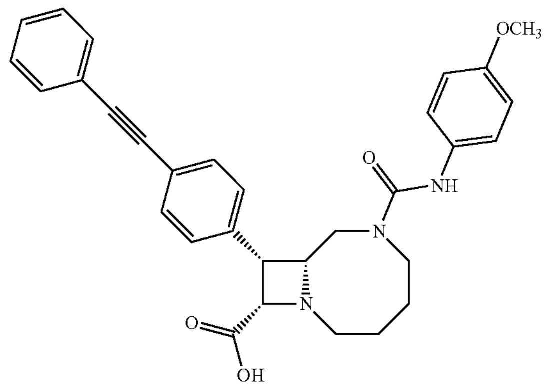 [SMILES: COc1ccc(NC(=O)N2CCCCN3[C@H](C(=O)O)[C@H](c4ccc(C#Cc5ccccc5)cc4)[C@@H]3C2)cc1] | (8R,9R,10S)-6-[(4-methoxyphenyl)carbamoyl]-9-[4-(2-phenylethynyl)phenyl]-1,6-diazabicyclo[6.2.0]decane-10-carboxylic acid | Method A 0.76 | $C_{31}H_{32}N_3O_4$ [M + H]+ 510.231: 510.38 |
| 54 | 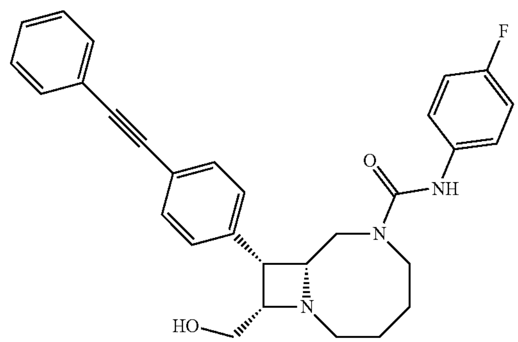 [SMILES: O=C(Nc1ccc(F)cc1)N1CCCCN2[C@H](CO)[C@H](c3ccc(C#Cc4ccccc4)cc3)[C@@H]2C1] | (8R,9R,10S)-N-(4-fluorophenyl)-10-(hydroxymethyl)-9-[4-(2-phenylethynyl)phenyl]-1,6-diazabicyclo[6.2.0]decane-6-carboxamide | Method A 0.84 | $C_{30}H_{30}FN_3O_2$ [M + H]+ 484.232: 484.42 |
| 55 | 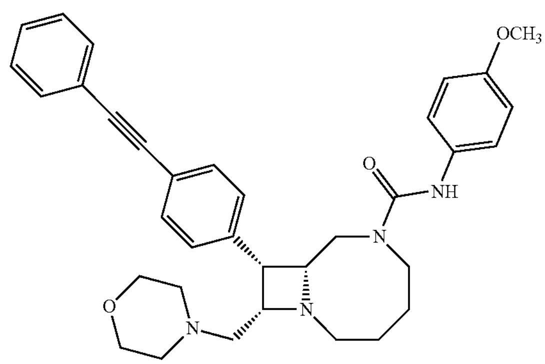 [SMILES: COc1ccc(NC(=O)N2CCCCN3[C@H](CN4CCOCC4)[C@H](c4ccc(C#Cc5ccccc5)cc4)[C@@H]3C2)cc1] | (8R,9S,10S)-N-(4-methoxyphenyl)-10-(morpholin-4-ylmethyl)-9-[4-(2-phenylethynyl)phenyl]-1,6-diazabicyclo[6.2.0]decane-6-carboxamide | Method A 0.90 | $C_{35}H_{41}N_4O_3$ [M + H]+ 565.31: 565.29 |
| 56 | 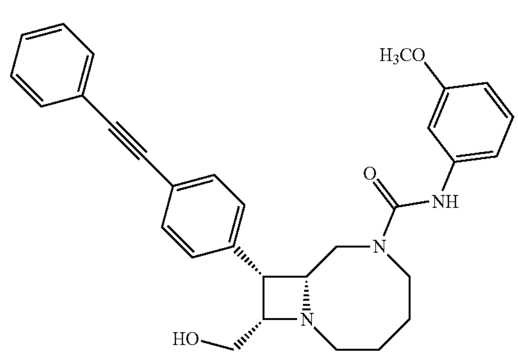 [SMILES: COc1cccc(NC(=O)N2CCCCN3[C@H](CO)[C@H](c4ccc(C#Cc5ccccc5)cc4)[C@@H]3C2)c1] | (8R,9R,10S)-10-(hydroxymethyl)-N-(3-methoxypheny])-9-[4-(2-phenylethynyl)phenyl]-1,6-diazabicyclo[6.2.0]decane-6-carboxamide | Method A 0.84 | $C_{31}H_{34}N_3O_3$ [M + H]+ 496.252: 496.50 |

TABLE 1-continued

Selected Compounds of the Invention

| # | Structure | Name | Retention Time | LRMS (Calculated: Found) |
|---|---|---|---|---|
| 57 | 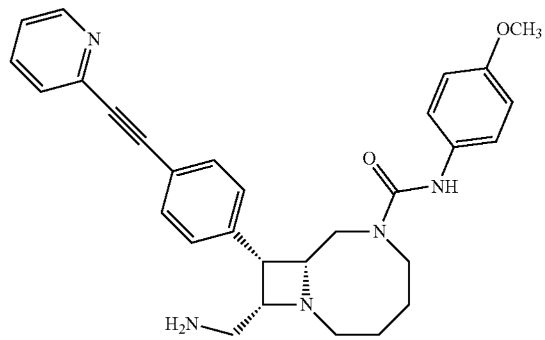 [SMILES: COc1ccc(NC(=O)N2CCCCN3[C@H](CN)[C@H](c4ccc(C#Cc5ccccn5)cc4)[C@@H]3C2)cc1] | (8R,9S,10S)-10-(aminomethyl)-N-(4-methoxyphenyl)-9-{4-[2-(pyridin-2-yl)ethynyl]phenyl}-1,6-diazabicyclo[6.2.0]decane-6-carboxamide | Method A 0.49 | $C_{30}H_{33}N_5O_2$ [M + H]+ 495.263: 495.20 |
| 58 | 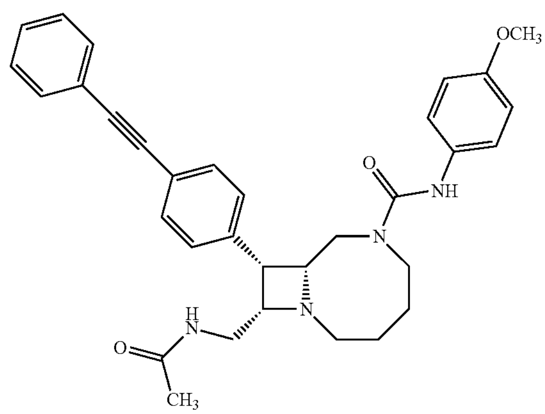 [SMILES: COc1ccc(NC(=O)N2CCCCN3[C@H](CNC(C)=O)[C@H](c4ccc(C#Cc5ccccc5)cc4)[C@@H]3C2)cc1] | (8R,9S,10S)-10-(acetamidomethyl)-N-(4-methoxyphenyl)-9-[4-(2-phenylethynyl)phenyl]-1,6-diazabicyclo[6.2.0]decane-6-carboxamide | Method A 0.79 | $C_{33}H_{37}N_4O_3$ [M + H]+ 537.28: 537.27 |
| 59 | 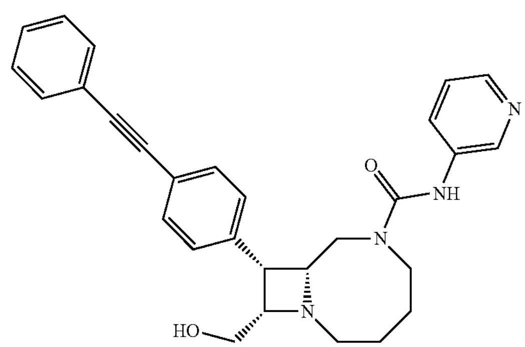 [SMILES: O=C(Nc1cccnc1)N1CCCCN2[C@H](CO)[C@H](c3ccc(C#Cc4ccccc4)cc3)[C@@H]2C1] | (8R,9R,10S)-10-(hydroxymethyl)-9-[4-(2-phenylethynyl)phenyl]-N-(pyridin-3-yl)-1,6-diazabicyclo[6.2.0]decane-6-carboxamide | Method A 0.76 | $C_{29}H_{30}N_4O_2$ [M − H]− 466.237: 465.41 |
| 60 | 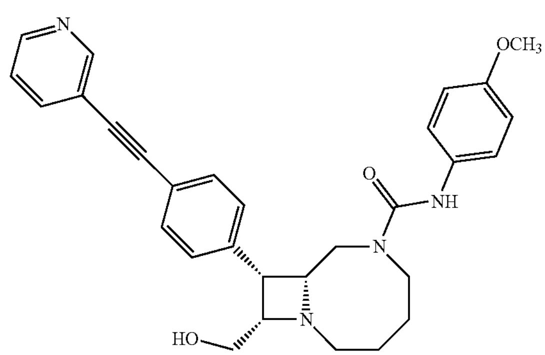 [SMILES: COc1ccc(NC(=O)N2CCCCN3[C@H](CO)[C@H](c4ccc(C#Cc5cccnc5)cc4)[C@@H]3C2)cc1] | (8R,9R,10S)-10-(hydroxymethyl)-N-(4-methoxyphenyl)-9-{4-[2-(pyridin-3-yl)ethynyl]phenyl}-1,6-diazabicyclo[6.2.0]decane-6-carboxamide | Method A 0.71 | $C_{30}H_{33}N_4O_3$ [M + H]+ 497.24: 497.49 |

TABLE 1-continued

Selected Compounds of the Invention

| # | Structure | Name | Retention Time | LRMS (Calculated: Found) |
|---|---|---|---|---|
| 61 | 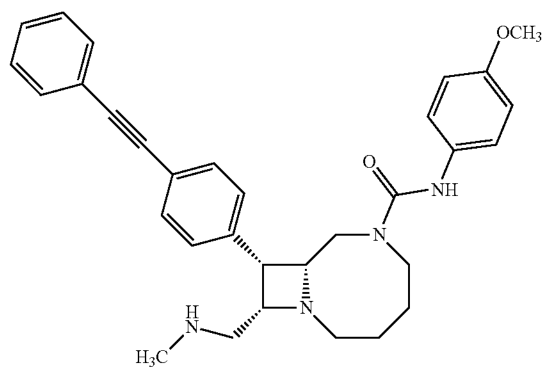 [SMILES: CNC[C@@H]1[C@H](c2ccc(C#Cc3ccccc3)cc2)[C@@H]2CN(C(=O)Nc3ccc(OC)cc3)CCCCN12] | (8R,9S,10S)-N-(4-methoxyphenyl)-10-[(methylamino)methyl]-9-[4-(2-phenylethynyl)phenyl]-1,6-diazabicyclo[6.2.0]decane-6-carboxamide | Method A 0.65 | $C_{32}H_{37}N_4O_2$ [M + H]+ 509.284: 509.07 |
| 62 | 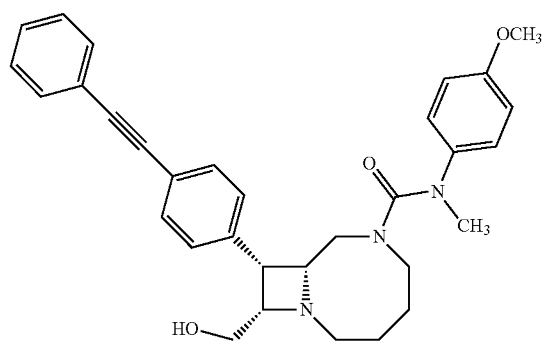 [SMILES: COc1ccc(N(C)C(=O)N2CCCCN3[C@H](CO)[C@H](c4ccc(C#Cc5ccccc5)cc4)[C@@H]3C2)cc1] | (8R,9R,10S)-10-(hydroxymethyl)-N-(4-methoxyphenyl)-N-methyl-9-[4-(2-phenylethynyl)phenyl]-1,6-diazabicyclo[6.2.0]decane-6-carboxamide | Method A 0.85 | $C_{32}H_{36}N_3O_3$ [M + H]+ 510.27: 510.48 |
| 63 | 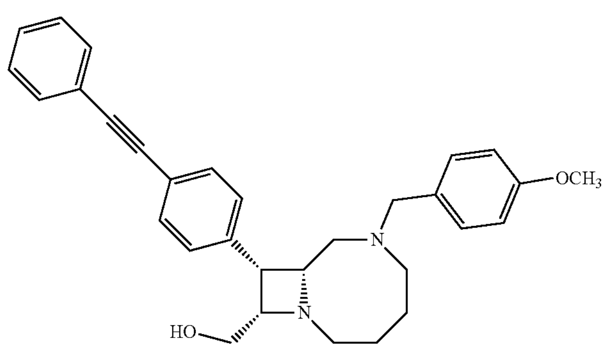 [SMILES: COc1ccc(CN2CCCCN3[C@H](CO)[C@H](c4ccc(C#Cc5ccccc5)cc4)[C@@H]3C2)cc1] | [(8R,9R,10S)-6-[(4-methoxyphenyl)methyl]-9-[4-(2-phenylethynyl)phenyl]-1,6-diazabicyclo[6.2.0]decan-10-yl]methanol | Method A 0.99 | $C_{31}H_{35}N_2O_2$ [M + H]+ 467.26: 467.51 |
| 64 | 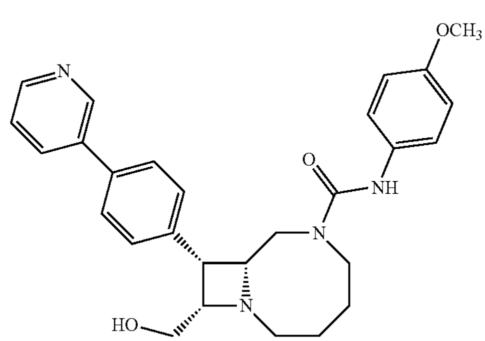 [SMILES: COc1ccc(NC(=O)N2CCCCN3[C@H](CO)[C@H](c4ccc(-c5cccnc5)cc4)[C@@H]3C2)cc1] | (8R,9R,10S)-10-(hydroxymethyl)-N-(4-methoxyphenyl)-9-[4-(pyridin-3-yl)phenyl]-1,6-diazabicyclo[6.2.0]decane-6-carboxamide | Method A 0.64 | $C_{28}H_{33}N_4O_3$ [M + H]+ 473.25: 473.47 |

TABLE 1-continued

Selected Compounds of the Invention

| # | Structure | Name | Retention Time | LRMS (Calculated: Found) |
|---|---|---|---|---|
| 65 | 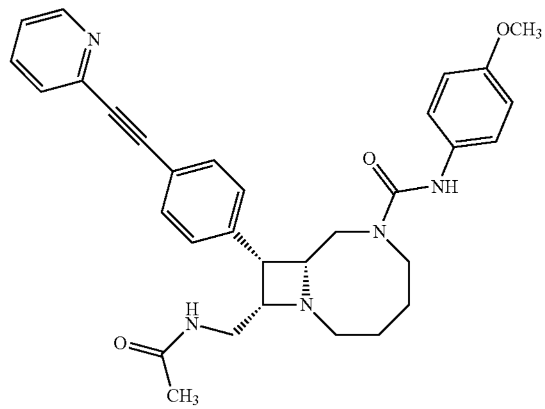 [SMILES: COc1ccc(NC(=O)N2CCCCN3[C@H](CNC(C)=O)[C@H](c4ccc(C#Cc5ccccn5)cc4)[C@@H]3C2)cc1] | (8R,9S,10S)-10-(acetamidomethyl)-N-(4-methoxyphenyl)-9-{4-[2-(pyridin-2-yl)ethynyl]phenyl}-1,6-diazabicyclo[6.2.0]decane-6-carboxamide | Method A 0.67 | $C_{32}H_{36}N_5O_3$ [M + H]+ 538.27: 538.20 |
| 66 | 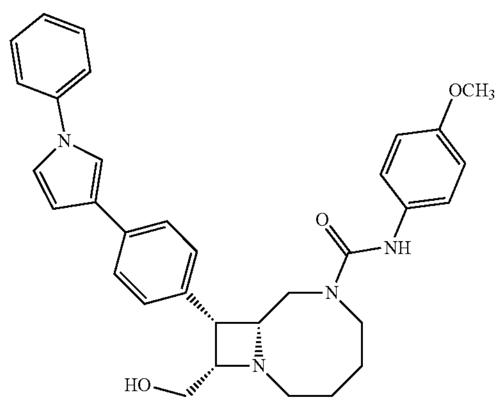 [SMILES: COc1ccc(NC(=O)N2CCCCN3[C@H](CO)[C@H](c4ccc(-c5ccn(-c6ccccc6)c5)cc4)[C@@H]3C2)cc1] | (8R,9R,10S)-10-(hydroxymethyl)-N-(4-methoxyphenyl)-9-[4-(1-phenyl-1H-pyrrol-3-yl)phenyl]-1,6-diazabicyclo[6.2.0]decane-6-carboxamide | Method A 0.82 | $C_{33}H_{37}N_4O_3$ [M + H]+ 537.28: 537.54 |
| 67 | 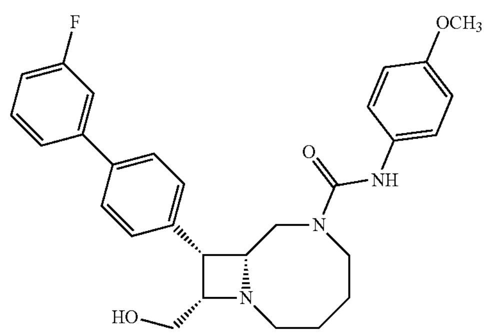 [SMILES: COc1ccc(NC(=O)N2CCCCN3[C@H](CO)[C@H](c4ccc(-c5cccc(F)c5)cc4)[C@@H]3C2)cc1] | (8R,9R,10S)-9-[4-(3-fluorophenyl)phenyl]-10-(hydroxymethyl)-N-(4-methoxyphenyl)-1,6-diazabicyclo[6.2.0]decane-6-carboxamide | Method A 0.79 | $C_{29}H_{33}FN_3O_3$ [M + H]+ 490.243: 490.49 |
| 68 | 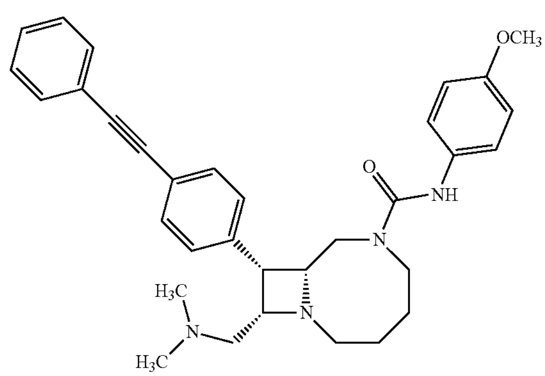 [SMILES: COc1ccc(NC(=O)N2CCCCN3[C@H](CN(C)C)[C@H](c4ccc(C#Cc5ccccc5)cc4)[C@@H]3C2)cc1] | (8R,9S,10S)-10-[(dimethylamino)methyl]-N-(4-methoxyphenyl)-9-[4-(2-phenylethynyl)phenyl]-1,6-diazabicyclo[6.2.0]decane-6-carboxamide | Method A 0.93 | $C_{33}H_{39}N_4O_2$ [M + H]+ 523.299: 523.63 |

TABLE 1-continued

Selected Compounds of the Invention

| # | Structure | Name | Retention Time | LRMS (Calculated: Found) |
|---|---|---|---|---|
| 69 | 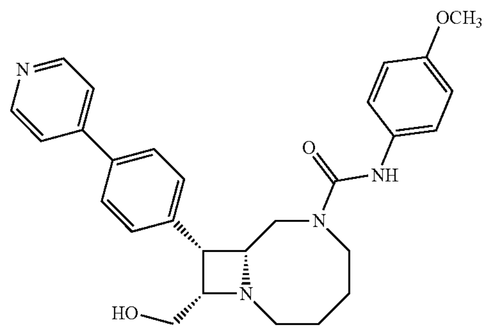 [SMILES: COc1ccc(NC(=O)N2CCCCN3[C@H](CO)[C@H](c4ccc(-c5ccncc5)cc4)[C@@H]3C2)cc1] | (8R,9R,10S)-10-(hydroxymethyl)-N-(4-methoxyphenyl)-9-[4-(pyridin-4-yl)phenyl]-1,6-diazabicyclo[6.2.0]decane-6-carboxamide | Method A 0.64 | $C_{28}H_{33}N_4O_3$ [M + H]+ 473.25: 473.49 |
| 70 | 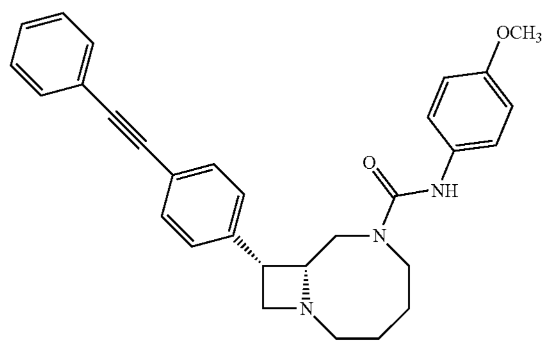 | (8R,9S)-N-(4-methoxyphenyl)-9-[4-(2-phenylethynyl)phenyl]-1,6-diazabicyclo[6.2.0]decane-6-carboxamide | Method B 2.14 | $C_{30}H_{32}N_3O_2$ [M + H]+ 466.24: 466.30 |
| 71 | 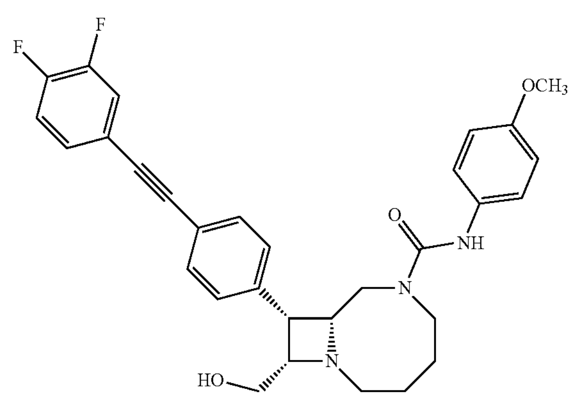 [SMILES: COc1ccc(NC(=O)N2CCCCN3[C@H](CO)[C@H](c4ccc(C#Cc5ccc(F)c(F)c5)cc4)[C@@H]3C2)cc1] | (8R,9R,10S)-9-{4-[2-(3,4-difluorophenyl)ethynyl]phenyl}-10-(hydroxymethyl)-N-(4-methoxyphenyl)-1,6-diazabicyclo[6.2.0]decane-6-carboxamide | Method A 0.82 | $C_{31}H_{32}F_2N_3O_3$ [M + H]+ 532.233: 532.43 |
| 72 | 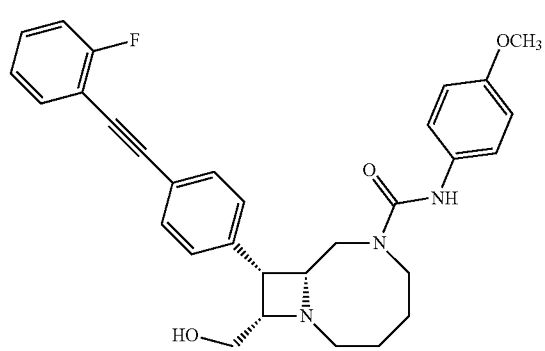 [SMILES: COc1ccc(NC(=O)N2CCCCN3[C@H](CO)[C@H](c4ccc(C#Cc5ccccc5F)cc4)[C@@H]3C2)cc1] | (8R,9R,10S)-9-{4-[2-(2-fluorophenyl)ethynyl]phenyl}-10-(hydroxymethyl)-N-(4-methoxyphenyl)-1,6-diazabicyclo[6.2.0]decane-6-carboxamide | Method A 0.82 | $C_{31}H_{33}FN_3O_3$ [M + H]+ 514.24: 514.49 |

TABLE 1-continued

Selected Compounds of the Invention

| # | Structure | Name | Retention Time | LRMS (Calculated: Found) |
|---|---|---|---|---|
| 73 | 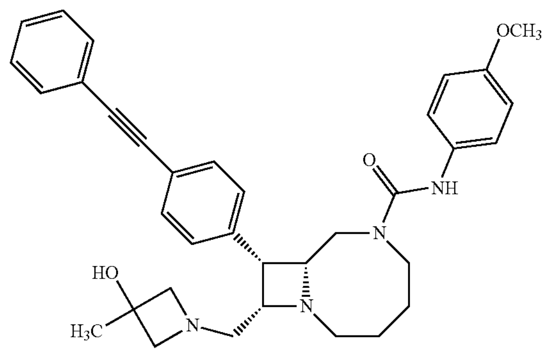 [SMILES: COc1ccc(NC(=O)N2CCCCN3[C@H](CN4CC(C)(O)C4)[C@H](c4ccc(C#Cc5ccccc5)cc4)[C@@H]3C2)cc1] | (8R,9S,10S)-10-[(3-hydroxy-3-methylazetidin-1-yl)methyl]-N-(4-methoxyphenyl)-9-[4-(2-phenylethynyl)phenyl]-1,6-diazabicyclo[6.2.0]decane-6-carboxamide | Method A 0.85 | $C_{35}H_{41}N_4O_3$ [M + H]+ 565.31: 565.20 |
| 74 | 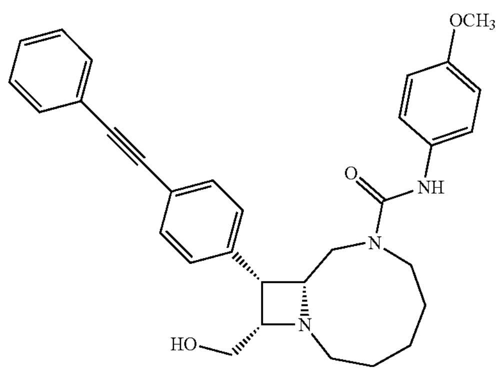 [SMILES: COc1ccc(NC(=O)N2CCCCCN3[C@H](CO)[C@H](c4ccc(C#Cc5ccccc5)cc4)[C@@H]3C2)cc1] | (9R,10R,11S)-11-(hydroxymethyl)-N-(4-methoxyphenyl)-10-[4-(2-phenylethynyl)phenyl]-1,7-diazabicyclo[7.2.0]undecane-7-carboxamide | Method A 0.84 | $C_{32}H_{36}N_3O_3$ [M + H]+ 510.27: 510.30 |
| 75 | 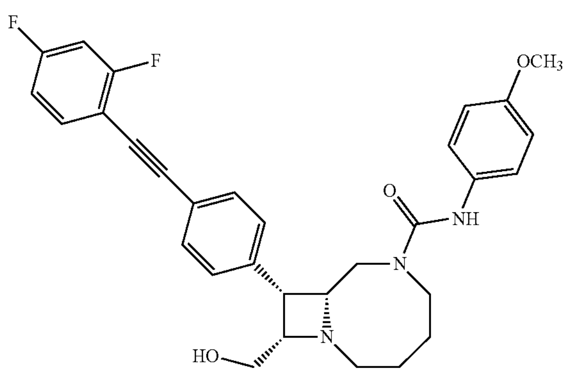 [SMILES: COc1ccc(NC(=O)N2CCCCN3[C@H](CO)[C@H](c4ccc(C#Cc5ccc(F)cc5F)cc4)[C@@H]3C2)cc1] | (8R,9R,10S)-9-{4-[2-(2,4-difluorophenyl)ethynyl]phenyl}-10-(hydroxymethyl)-N-(4-methoxyphenyl)-1,6-diazabicyclo[6.2.0]decane-6-carboxamide | Method A 0.81 | $C_{31}H_{32}F_2N_3O_3$ [M + H]+ 532.23: 532.44 |
| 76 | 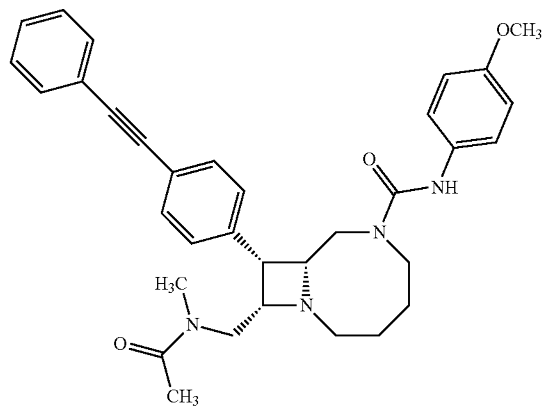 [SMILES: COc1ccc(NC(=O)N2CCCCN3[C@H](CN(C)C(C)=O)[C@H](c4ccc(C#Cc5ccccc5)cc4)[C@@H]3C2)cc1] | (8R,9S,10S)-N-(4-methoxyphenyl)-10-[(N-methylacetamido)methyl]-9-[4-(2-phenylethynyl)phenyl]-1,6-diazabicyclo[6.2.0]decane-6-carboxamide | Method A 0.85 | $C_{34}H_{39}N_4O_3$ [M + H]+ 551.294: 551.55 |

TABLE 1-continued

Selected Compounds of the Invention

| # | Structure | Name | Retention Time | LRMS (Calculated: Found) |
|---|---|---|---|---|
| 77 | 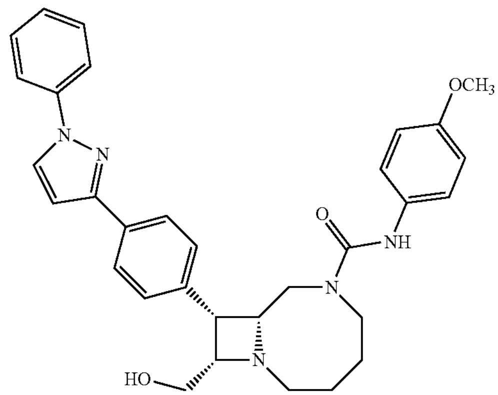 [SMILES: COc1ccc(NC(=O)N2CCCCN3[C@H](CO)[C@H](c4ccc(-c5ccn(-c6ccccc6)n5)cc4)[C@@H]3C2)cc1] | (8R,9R,10S)-10-(hydroxymethyl)-N-(4-methoxyphenyl)-9-[4-(1-phenyl-1H-pyrazol-3-yl)phenyl]-1,6-diazabicyclo[6.2.0]decane-6-carboxamide | Method A 0.75 | $C_{32}H_{35}N_5O_3$ [M + H]+ 537.274: 538.48 |
| 78 | 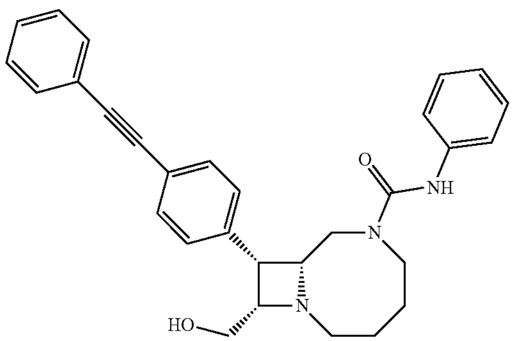 [SMILES: O=C(Nc1ccccc1)N1CCCCN2[C@H](CO)[C@H](c3ccc(C#Cc4ccccc4)cc3)[C@@H]2C1] | (8R,9R,10S)-10-(hydroxymethyl)-N-phenyl-9-[4-(2-phenylethynyl)phenyl]-1,6-diazabicyclo[6.2.0]decane-6-carboxamide | Method A 0.85 | $C_{30}H_{32}N_3O_2$ [M + H]+ 466.24: 466.46 |
| 79 | 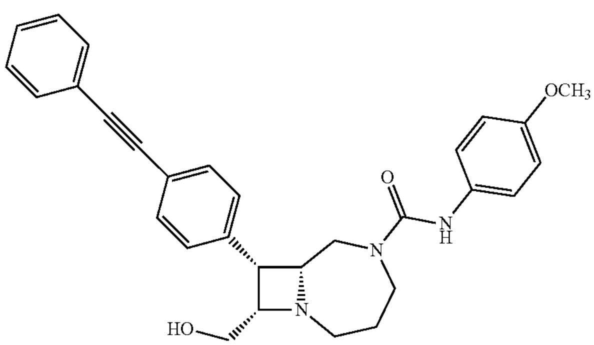 [SMILES: COc1ccc(NC(=O)N2CCCN3[C@H](CO)[C@H](c4ccc(C#Cc5ccccc5)cc4)[C@@H]3C2)cc1] | (7R,8R,9S)-9-(hydroxymethyl)-N-(4-methoxyphenyl)-8-[4-(2-phenylethynyl)phenyl]-1,5-diazabicyclo[5.2.0]nonane-5-carboxamide | Method A 0.79 | $C_{30}H_{32}N_3O_3$ [M + H]+ 482.24: 482.47 |
| 80 | 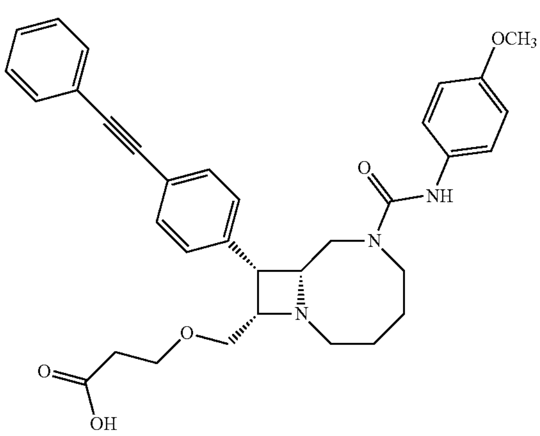 [SMILES: COc1ccc(NC(=O)N2CCCCN3[C@H](COCCC(=O)O)[C@H](c4ccc(C#Cc5ccccc5)cc4)[C@@H]3C2)cc1] | 3-(((8R,9R,10S)-6-((4-methoxyphenyl)carbamoyl)-9-(4-(phenylethynyl)phenyl)-1,6-diazabicyclo[6.2.0]decan-10-yl)methoxy)propanoic acid | Method B 1.5 | $C_{34}H_{37}N_3O_5$ [M + H]+ 568.27: 568.58 |

TABLE 1-continued

Selected Compounds of the Invention

| # | Structure | Name | Retention Time | LRMS (Calculated: Found) |
|---|-----------|------|----------------|--------------------------|
| 81 | 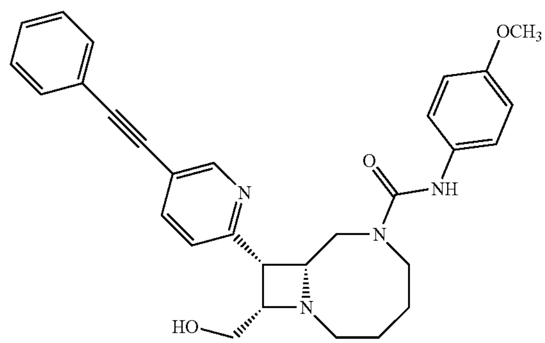 | (8R,9R,10S)-10-(hydroxymethyl)-N-(4-methoxyphenyl)-9-(5-(phenylethynyl)pyridin-2-yl)-1,6-diazabicyclo[6.2.0]decane-6-carboxamide | Method A 0.77 | $C_{30}H_{32}N_4O_3$ [M + H]+ 497.25: 497.15 |
| 82 | 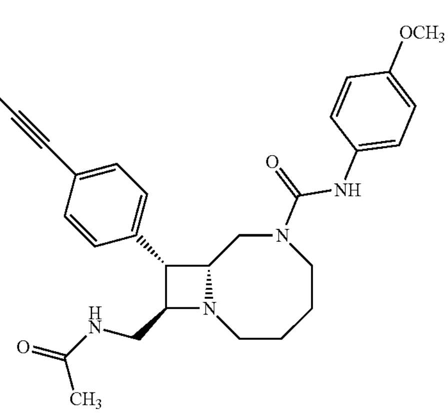 | (8R,9S,10R)-10-(acetamidomethyl)-N-(4-methoxyphenyl)-9-(4-(phenylethynyl)phenyl)-1,6-diazabicyclo[6.2.0]decane-6-carboxamide | Method A 0.78 | $C_{33}H_{36}N_4O_3$ [M + H]+ 537.28: 537.16 |
| 83 | 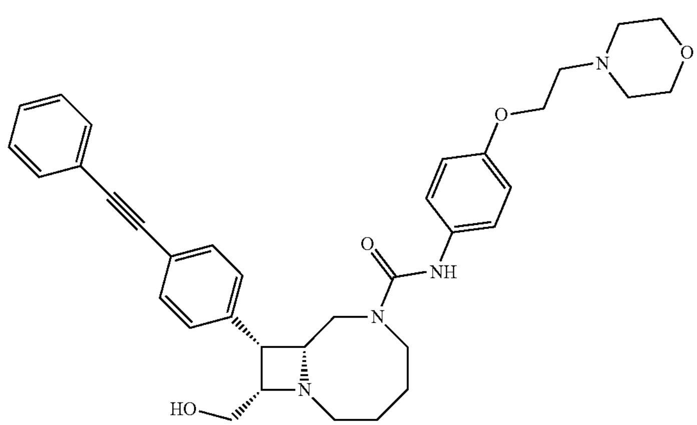 [SMILES: O=C(Nc1ccc(OCCN2CCOCC2)cc1)N1CCCCN2[C@H](CO)[C@H](c3ccc(C#Cc4ccccc4)cc3)[C@@H]2C1] | (8R,9R,10S)-10-(hydroxymethyl)-N-(4-(2-morpholinoethoxy)phenyl)-9-(4-(phenylethynyl)phenyl)-1,6-diazabicyclo[6.2.0]decane-6-carboxamide | Method A 0.78 | $C_{36}H_{42}N_4O_4$ [M + H]+ 595.32: 595.46 |
| 84 | 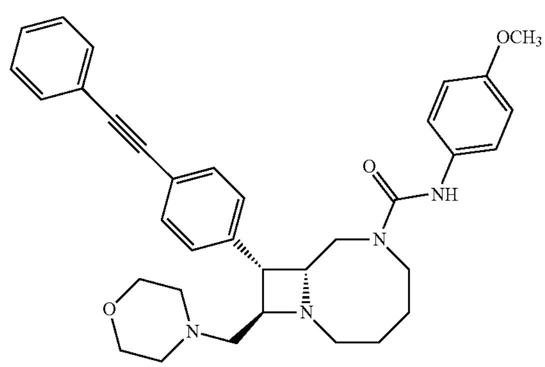 [SMILES: COc1ccc(NC(=O)N2CCCCN3[C@@H](CN4CCOCC4)[C@H](c4ccc(C#Cc5ccccc5)cc4)[C@@H]3C2)cc1] | (8R,9S,10R)-N-(4-methoxyphenyl)-10-(morpholinomethyl)-9-(4-(phenylethynyl)phenyl)-1,6-diazabicyclo[6.2.0]decane-6-carboxamide | Method A 0.88 | $C_{35}H_{40}N_4O_3$ [M + H]+ 565.31: 565.46 |

TABLE 1-continued

Selected Compounds of the Invention

| # | Structure | Name | Retention Time | LRMS (Calculated: Found) |
|---|-----------|------|----------------|--------------------------|
| 85 | 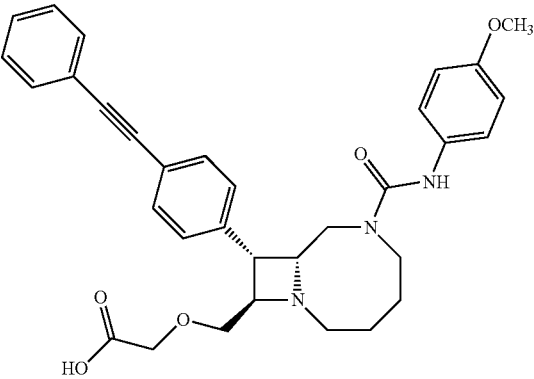 [SMILES: COc1ccc(NC(=O)N2CCCCN3[C@@H](COCC(=O)O)[C@H](c4ccc(C#Cc5ccccc5)cc4)[C@@H]3C2)cc1] | 2-(((8R,9R,10R)-6-((4-methoxyphenyl)carbamoyl)-9-(4-(phenylethynyl)phenyl)-1,6-diazabicyclo[6.2.0]decan-10-yl)methoxy)acetic acid | Method A 0.51 | $C_{33}H_{35}N_3O_5$ [M + H]+ 554.26: 554.41 |
| 86 | 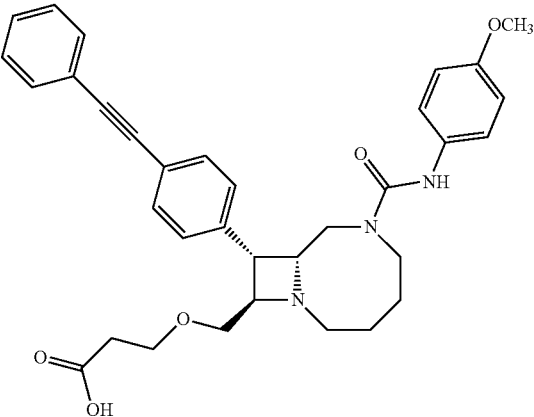 [SMILES: COc1ccc(NC(=O)N2CCCCN3[C@@H](COCCC(=O)O)[C@H](c4ccc(C#Cc5ccccc5)cc4)[C@@H]3C2)cc1] | 3-(((8R,9R,10R)-6-((4-methoxyphenyl)carbamoyl)-9-(4-(phenylethynyl)phenyl)-1,6-diazabicyclo[6.2.0]decan-10-yl)methoxy)propanoic acid | Method A 0.51 | $C_{34}H_{37}N_3O_5$ [M + H]+ 568.27: 568.40 |
| 87 | 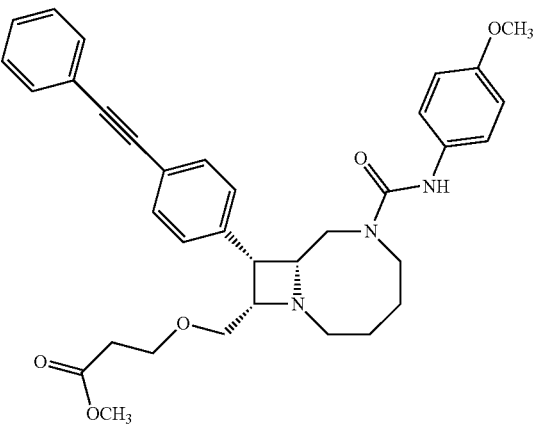 [SMILES: COC(=O)CCOC[C@@H]1[C@H](c2ccc(C#Cc3ccccc3)cc2)[C@@H]2CN(C(=O)Nc3ccc(OC)cc3)CCCCN12] | methyl 3-(((8R,9R,10S)-6-((4-methoxyphenyl)carbamoyl)-9-(4-(phenylethynyl)phenyl)-1,6-diazabicyclo[6.2.0]decan-10-yl)methoxy)propanoate | Method B 1.62 | $C_{35}H_{39}N_3O_5$ [M + H]+ 582.29: 582.51 |

TABLE 1-continued

Selected Compounds of the Invention

| # | Structure | Name | Retention Time | LRMS (Calculated: Found) |
|---|---|---|---|---|
| 88 | 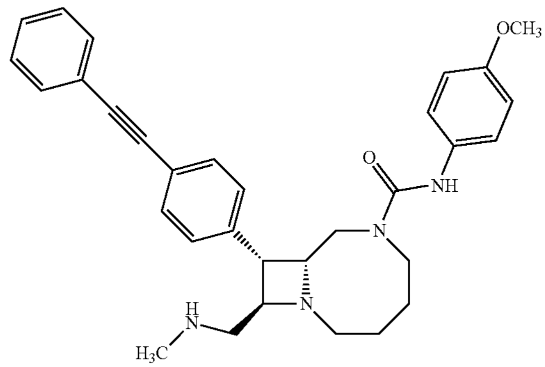 [SMILES: CNC[C@H]1[C@H](c2ccc(C#Cc3ccccc3)cc2)[C@@H]2CN(C(=O)Nc3ccc(OC)cc3)CCCCN12] | (8R,9S,10R)-N-(4-methoxyphenyl)-10-((methylamino)methyl)-9-(4-(phenylethynyl)phenyl)-1,6-diazabicyclo[6.2.0]decane-6-carboxamide | Method B 1.86 | $C_{32}H_{36}N_4O_2$ [M + H]+ 509.28: 509.61 |
| 89 | 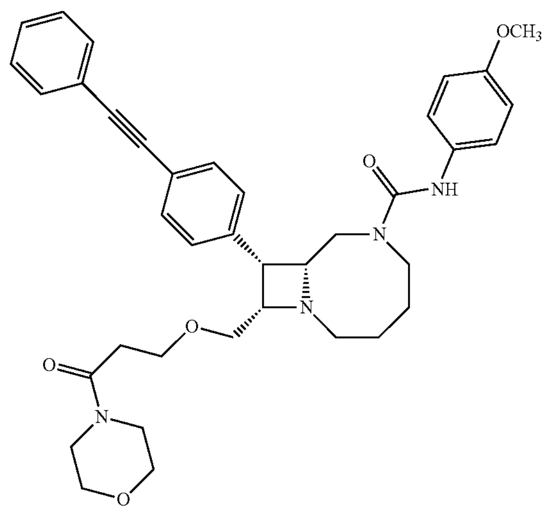 [SMILES: COc1ccc(NC(=O)N2CCCCN3[C@H](COCCC(=O)N4CCOCC4)[C@H](c4ccc(C#Cc5ccccc5)cc4)[C@@H]3C2)cc1] | (8R,9R,10S)-N-(4-methoxyphenyl)-10-((3-morpholino-3-oxopropoxy)methyl)-9-(4-(phenylethynyl)phenyl)-1,6-diazabicyclo[6.2.0]decane-6-carboxamide | Method B 1.89 | $C_{38}H_{44}N_4O_5$ [M + H]+ 637.33: 637.69 |
| 90 | 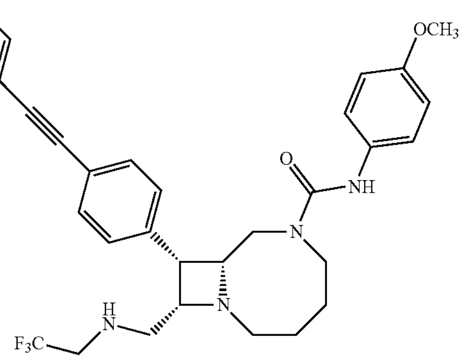 | (8R,9S,10S)-N-(4-methoxyphenyl)-9-(4-(phenylethynyl)phenyl)-10-(((2,2,2-trifluoroethyl)amino)methyl)-1,6-diazabicyclo[6.2.0]decane-6-carboxamide | Method B 2.16 | $C_{33}H_{35}F_3N_4O_2$ [M + H]+ 577.27: 577.63 |

TABLE 1-continued

Selected Compounds of the Invention

| # | Structure | Name | Retention Time | LRMS (Calculated: Found) |
|---|-----------|------|----------------|--------------------------|
| 91 | 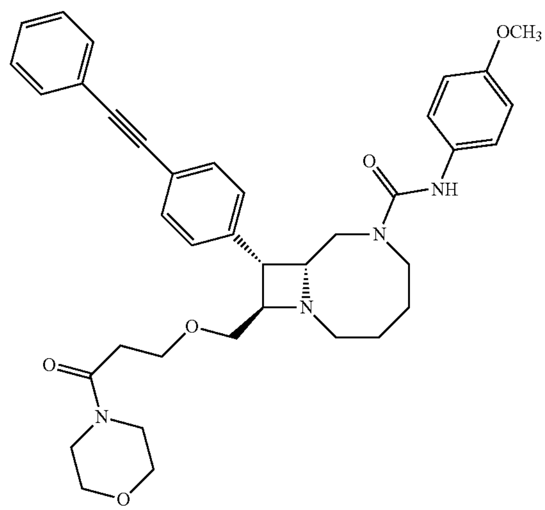 [SMILES: COc1ccc(NC(=O)N2CCCCN3[C@@H](COCCC(=O)N4CCOCC4)[C@H](c4ccc(C#Cc5ccccc5)cc4)[C@@H]3C2)cc1] | (8R,9R,10R)-N-(4-methoxyphenyl)-10-((3-morpholino-3-oxopropoxy)methyl)-9-(4-(phenylethynyl)phenyl)-1,6-diazabicyclo[6.2.0]decane-6-carboxamide | Method B 1.87 | $C_{38}H_{44}N_4O_5$ [M + H]+ 637.33: 637.53 |
| 92 | 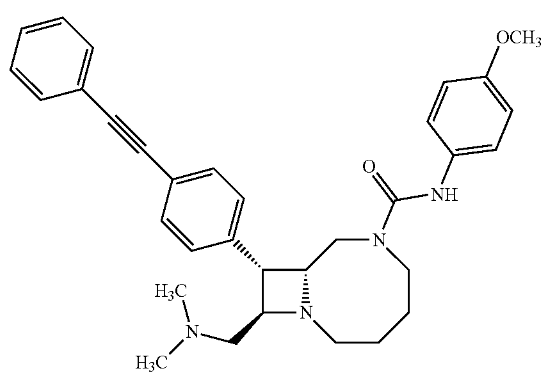 [SMILES: COc1ccc(NC(=O)N2CCCCN3[C@@H](CN(C)C)[C@H](c4ccc(C#Cc5ccccc5)cc4)[C@@H]3C2)cc1] | (8R,9S,10R)-10-((dimethylamino)methyl)-N-(4-methoxyphenyl)-9-(4-(phenylethynyl)phenyl)-1,6-diazabicyclo[6.2.0]decane-6-carboxamide | Method B 2.06 | $C_{33}H_{38}N_4O_2$ [M + H]+ 523.30: 523.05 |
| 93 | 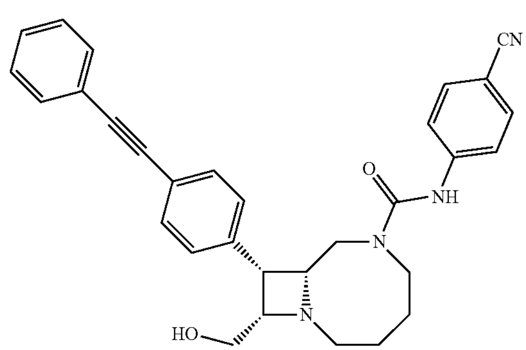 [SMILES: N#Cc1ccc(NC(=O)N2CCCCN3[C@H](CO)[C@H](c4ccc(C#Cc5ccccc5)cc4)[C@@H]3C2)cc1] | (8R,9R,10S)-N-(4-cyanophenyl)-10-(hydroxymethyl)-9-(4-(phenylethynyl)phenyl)-1,6-diazabicyclo[6.2.0]decane-6-carboxamide | Method B 1.84 | $C_{31}H_{30}N_4O_2$ [M + H]+ 491.24: 491.57 |

TABLE 1-continued

Selected Compounds of the Invention

| # | Structure | Name | Retention Time | LRMS (Calculated: Found) |
|---|---|---|---|---|
| 94 | 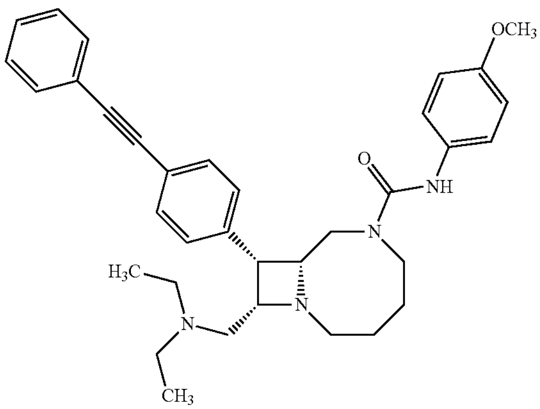 [SMILES: CCN(CC)C[C@@H]1[C@H](c2ccc(C#Cc3ccccc3)cc2)[C@@H]2CN(C(=O)Nc3ccc(OC)cc3)CCCCN12] | (8R,9S,10S)-10-((diethylamino)methyl)-N-(4-methoxyphenyl)-9-(4-(phenylethynyl)phenyl)-1,6-diazabicyclo[6.2.0]decane-6-carboxamide | Method B 2.35 | $C_{35}H_{42}N_4O_2$ [M + H]+ 551.33: 551.04 |
| 95 | 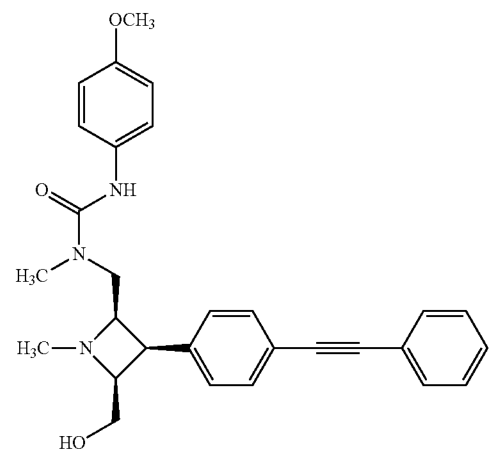 [SMILES: COc1ccc(NC(=O)N(C)C[C@H]2[C@@H](c3ccc(C#Cc4ccccc4)cc3)[C@@H](CO)N2C)cc1] | 1-(((2R,3R,4S)-4-(hydroxymethyl)-1-methyl-3-(4-(phenylethynyl)phenyl)azetidin-2-yl)methyl)-3-(4-methoxyphenyl)-1-methylurea | Method B 1.72 | $C_{29}H_{31}N_3O_3$ [M + H]+ 470.24: 470.33 |

In another aspect, the invention features a pharmaceutical composition including a therapeutically effective amount of a compound having the structure:

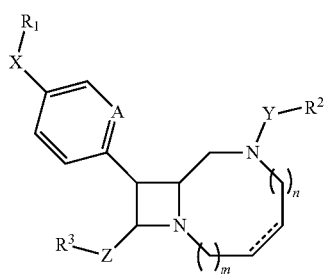

Formula I wherein the dotted line represents an optional double bond;
m is 0 or 1;
n is 0, 1, or 2;
A is CH or N;
X is absent or —C≡C—;
$R^1$ is hydrogen, $C_1$-$C_6$ alkyl, $C_1$-$C_6$ heteroalkyl, $C_6$-$C_{10}$ aryl, $C_3$-$C_{10}$ carbocyclyl, or $C_2$-$C_9$ heteroaryl;

Y is $C_1$-$C_6$ alkylene, —C(O)$NR^4$—; —$SO_2$—, or —C(O)—;
$R^2$ is $C_1$-$C_6$ perfluoroalkyl, $C_6$-$C_{10}$ aryl, $C_6$-$C_{10}$ aryl $C_1$-$C_6$ alkyl, $C_3$-$C_{ia}$ carbocyclyl, or $C_2$-$C_9$ heteroaryl;
Z is absent, $C_1$-$C_6$ alkylene, or $C_1$-$C_6$ heteroalkylene;
$R^3$ is hydrogen, hydroxyl, —$NR^5R^6$, —C(O)$R^7$, or $C_2$-$C_9$ heterocyclyl;
$R^4$ is hydrogen or $C_1$-$C_6$ alkyl;
$R^5$ and $R^6$ are independently hydrogen, $C_1$-$C_6$ alkyl, or $C_1$-$C_6$ acyl; and
$R^7$ is hydroxyl, $C_1$-$C_6$ heteroalkyl, or $C_2$-$C_9$ heterocyclyl;
or a pharmaceutically acceptable salt thereof;
and a pharmaceutically acceptable excipient.

In some embodiments, the compound is any one of compounds 1 to 94 in Table 1 or a pharmaceutically acceptable salt thereof.

In another aspect, the invention features a pharmaceutical composition including a therapeutically effective amount of compound 95 of Table 1 or a pharmaceutically acceptable salt thereof and a pharmaceutically acceptable excipient.

In another aspect, the invention features a method of preventing or treating malaria (e.g., malaria caused by *P. falciparum, P. vivax, P. ovale, P. malariae,* or *P. knowlesi*) in a subject. This method includes the step of administering to the subject an effective amount of a compound having the structure:

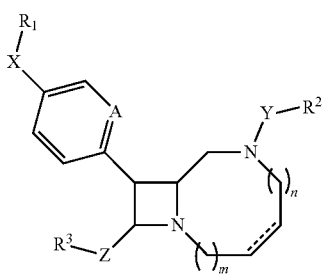

Formula I wherein the dotted line represents an optional double bond;

m is 0 or 1;

n is 0, 1, or 2;

A is CH or N;

X is absent or —C≡C—;

$R^1$ is hydrogen, $C_1$-$C_6$ alkyl, $C_1$-$C_6$ heteroalkyl, $C_6$-$C_{10}$ aryl, $C_3$-$C_{10}$ carbocyclyl, or $C_2$-$C_9$ heteroaryl;

Y is $C_1$-$C_6$ alkylene, —C(O)$NR^4$—; —$SO_2$—, or —C(O)—;

$R^2$ is $C_1$-$C_6$ perfluoroalkyl, $C_6$-$C_{10}$ aryl, $C_6$-$C_{10}$ aryl $C_1$-$C_6$ alkyl, $C_3$-$C_{10}$ carbocyclyl, or $C_2$-$C_9$ heteroaryl;

Z is absent, $C_1$-$C_6$ alkylene, or $C_1$-$C_6$ heteroalkylene;

$R^3$ is hydrogen, hydroxyl, —$NR^5R^6$, —C(O)$R^7$, or $C_2$-$C_9$ heterocyclyl;

$R^4$ is hydrogen or $C_1$-$C_6$ alkyl;

$R^5$ and $R^6$ are independently hydrogen, $C_1$-$C_6$ alkyl, or $C_1$-$C_6$ acyl; and $R^7$ is hydroxyl, $C_1$-$C_6$ heteroalkyl, or $C_2$-$C_9$ heterocyclyl;

or a pharmaceutically acceptable salt thereof.

In some embodiments, the compound is any one of compounds 1 to 94 of Table 1 or a pharmaceutically acceptable salt thereof.

In some embodiments of any of the foregoing methods, the malaria is drug resistant (e.g., the malaria is resistant to chloroquine, quinine, pyrimethamine, sulfadoxine, mefloquine, artemether, lumefantrine, artesunate, amodiaquine, dihydroartemisinin, piperaquine, proguanil, doxycycline, clindamycin, artemisinin, atovaquone, or any combination thereof).

In some embodiments, the malaria is liver stage (also known as hepatic stage malaria). In other embodiments, the malaria is blood stage (also known as erythrocytic stage malaria). In some embodiments, the malaria is transmission stage (i.e., the stage in which transmission of the parasite back to a mosquito occurs also known as gametocytic stage malaria).

In another aspect, the invention features a method of preventing or treating malaria (e.g., malaria caused by *P. falciparum, P. vivax, P. ovale, P. malariae*, or *P. knowlesi*) in a subject. This method includes the step of administering to the subject an effective amount of a compound 95 or a pharmaceutically acceptable salt thereof.

In some embodiments of any of the foregoing methods, the malaria is drug resistant (e.g., the malaria is resistant to chloroquine, quinine, pyrimethamine, sulfadoxine, mefloquine, artemether, lumefantrine, artesunate, amodiaquine, dihydroartemisinin, piperaquine, proguanil, doxycycline, clindamycin, artemisinin, atovaquone, or any combination thereof).

In some embodiments, the malaria is hepatic. In other embodiments, the malaria is blood stage. In some embodiments, the invention concerns preventing transmission of malaria back to the mosquito.

In another aspect, the invention features a compound according to Formula VIII:

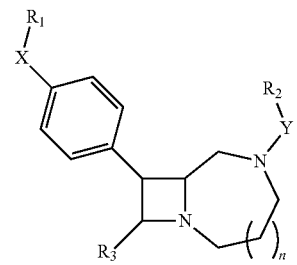

Formula VIII wherein:

n is 0, 1, 2 or 3;

X is a single bond, hydrogen, —C≡C—, thiazolyl, pyrrolyl, pyrazolyl, pyridinyl, phenyl monosubstituted with —F or phenyl disubstituted with halogen or absent;

Y is —$CH_2$—, —C(O)NH—, —S(O)$_2$—, —$CH_2CH_2$—, —S(O)$_2CH_2$—, —C(O)—, or —C(O)N(CH$_3$)—;

$R_1$ is pyridinyl, cyclopropyl, —CH(CH$_3$)$_2$, —OCH$_3$, cyclopentyl, cyclohexyl, cyclohexenyl, unsubstituted phenyl, phenyl monosubstituted with —CH$_3$, —OCH$_3$ or halogen, phenyl disubstituted with halogen or absent;

$R_2$ is —CF$_3$, cyclohexyl, pyridinyl, unsubstituted phenyl or phenyl substituted with —CH$_3$, —OCH$_3$ or halogen;

$R_3$ is hydrogen, —C(O)OH or —CH$_2$—R$_4$; and $R_4$ is hydroxy, methylpiperazinyl, hydroxymethylpiperidinyl, —OCH$_2$C(O)OH, —NH$_2$, —C(O)OH, morpholinyl, —NHC(O)CH$_3$, —NHCH$_3$, —N(CH$_3$)$_2$, hydroxymethylazetidinyl or —N(CH$_3$)C(O)CH$_3$, or a pharmaceutically acceptable salt thereof, with the proviso that said compound is not any one of compounds 1 to 30 of Table 1.

In some embodiments, n is 1, 2 or 3. In other embodiments, n is 2. In certain embodiments, X is a single bond, hydrogen, or —C≡C—. In some embodiments, X is thiazolyl, pyrrolyl or pyrazolyl. In other embodiments, X is —C≡C—. In certain embodiments, $R_1$ is pyridinyl, cyclopropyl, —CH(CH$_3$)$_2$, —OCH$_3$, cyclopentyl, cyclohexyl, cyclohexenyl or absent. In some embodiments, $R_1$ is unsubstituted phenyl, phenyl monosubstituted with —CH$_3$, —OCH$_3$ or halogen or phenyl disubstituted with halogen. In other embodiments, $R_1$ is unsubstituted phenyl. In certain embodiments, Y is —C(O)NH— or —C(O)N(CH$_3$)—. In some embodiments, $R^2$ is —CF$_3$, cyclohexyl or pyridinyl. In other embodiments, $R^2$ is unsubstituted phenyl or phenyl substituted with —CH$_3$, —OCH$_3$ or halogen. In certain embodiments, $R^3$ is —CH$_2$—R$_4$. In some embodiments, $R^4$ is hydroxy, —OCH$_2$C(O)OH, —NH$_2$, —C(O)OH, —NHC(O)CH$_3$, —NHCH$_3$, —N(CH$_3$)$_2$, or —N(CH$_3$)C(O)CH$_3$. In some embodiments, $R^4$ is methylpiperazinyl, hydroxymethylpiperidinyl, morpholinyl or hydroxymethylazetidinyl. In other embodiments, $R^4$ is hydroxy. In certain embodiments, said compound is any one of compounds 31 to 95 of Table 1.

In another aspect, the invention features a pharmaceutical composition, comprising a therapeutically effective amount of a compound according to Formula VIII:

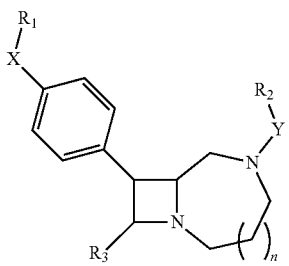

Formula VIII wherein:

n is 0, 1, 2 or 3;

X is a single bond, hydrogen, —C≡C—, thiazolyl, pyrrolyl, pyrazolyl, pyridinyl, phenyl monosubstituted with —F or phenyl disubstituted with halogen or absent;

Y is —CH$_2$—, —C(O)NH—, —S(O)$_2$—, —CH$_2$CH$_2$—, —S(O)$_2$CH$_2$—, —C(O)—, or —C(O)N(CH$_3$)—;

R$_1$ is pyridinyl, cyclopropyl, —CH(CH$_3$)$_2$, —OCH$_3$, cyclopentyl, cyclohexyl, cyclohexenyl, unsubstituted phenyl, phenyl monosubstituted with —CH$_3$, —OCH$_3$ or halogen, phenyl disubstituted with halogen or absent;

R$^2$ is —CF$_3$, cyclohexyl, pyridinyl, unsubstituted phenyl or phenyl substituted with —CH$_3$, —OCH$_3$ or halogen;

R$^3$ is hydrogen, —C(O)OH or —CH$_2$—R$_4$; and

R$^4$ is hydroxy, methylpiperazinyl, hydroxymethylpiperidinyl, —OCH$_2$C(O)OH, —NH$_2$, —C(O)OH, morpholinyl, —NHC(O)CH$_3$, —NHCH$_3$, —N(CH$_3$)$_2$, hydroxymethylazetidinyl or —N(CH$_3$)C(O)CH$_3$, or a pharmaceutically acceptable salt thereof and a pharmaceutically acceptable carrier.

In another aspect, the invention features a method of treating malaria, comprising the step of administering to a patient in need thereof a therapeutically effective amount of a compound according to Formula VIII:

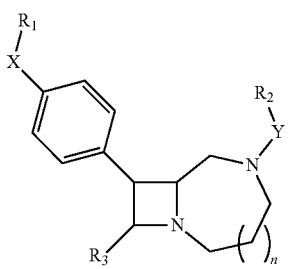

Formula VIII wherein:

n is 0, 1, 2 or 3;

X is a single bond, hydrogen, —C≡C—, thiazolyl, pyrrolyl, pyrazolyl, pyridinyl, phenyl monosubstituted with —F or phenyl disubstituted with halogen or absent;

Y is —CH$_2$—, —C(O)NH—, —S(O)$_2$—, —CH$_2$CH$_2$—, —S(O)$_2$CH$_2$—, —C(O)—, or —C(O)N(CH$_3$)—;

R$_1$ is pyridinyl, cyclopropyl, —CH(CH$_3$)$_2$, —OCH$_3$, cyclopentyl, cyclohexyl, cyclohexenyl, unsubstituted phenyl, phenyl monosubstituted with —CH$_3$, —OCH$_3$ or halogen, phenyl disubstituted with halogen or absent;

R$^2$ is —CF$_3$, cyclohexyl, pyridinyl, unsubstituted phenyl or phenyl substituted with —CH$_3$, —OCH$_3$ or halogen;

R$^3$ is hydrogen, —C(O)OH or —CH$_2$—R$_4$; and

R$^4$ is hydroxy, methylpiperazinyl, hydroxymethylpiperidinyl, —OCH$_2$C(O)OH, —NH$_2$, —C(O)OH, morpholinyl, —NHC(O)CH$_3$, —NHCH$_3$, —N(CH$_3$)$_2$, hydroxymethylazetidinyl or —N(CH$_3$)C(O)CH$_3$, or a pharmaceutically acceptable salt thereof.

The present invention is also directed to pharmaceutical compositions and to methods of treating malaria including/using a compound as described above or elsewhere herein.

Chemical Terms

It is to be understood that the terminology employed, herein is for the purpose of describing particular embodiments, and is not intended to be limiting. Further, although any methods and materials similar or equivalent to those described herein can be used in the practice or testing of the invention, the preferred methods and materials are now described.

The term "acyl," as used herein, represents a hydrogen or an alkyl group, as defined herein, that is attached to the parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons. In some embodiments, the alkyl group is further substituted with 1, 2, 3, or 4 substituents as described herein.

As used herein, the term "alkyl," alone or in combination with other groups, refers to a branched or straight-chain monovalent saturated aliphatic hydrocarbon radical of one to twenty carbon atoms (e.g., one to sixteen carbon atoms, one to ten carbon atoms, or one to six carbon atoms).

The term "alkylene" as used herein, represents a saturated divalent hydrocarbon group derived from a straight or branched chain saturated hydrocarbon by the removal of two hydrogen atoms, and is exemplified by methylene, ethylene, and isopropylene. In some embodiments, the alkylene can be further substituted with 1, 2, 3, or 4 substituent groups as defined herein for an alkyl group.

As used herein, the term "alkenyl," alone or in combination with other groups, refers to a straight-chain or branched hydrocarbon residue having an olefinic bond.

The term "amino," as used herein, represents —N(R$^{N1}$)$_2$, wherein each R$^{N1}$ is, independently, H, OH, NO$_2$, N(R$_{N2}$)$_2$, SO$_2$OR$^{N2}$, SO$_2$R$^{N2}$, SOR$^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or heterocyclylalkyl (e.g., heteroarylalkyl), wherein each of these recited R$^{N1}$ groups can be optionally substituted, as defined herein for each group; or two R$^{N1}$ combine to form a heterocyclyl or an N-protecting group, and wherein each R$^{N2}$ is, independently, H, alkyl, or aryl. The amino groups of the invention can be an unsubstituted amino (i.e., —NH$_2$) or a substituted amino (i.e., —N(R$^{N1}$)$_2$). In a preferred embodiment, amino is —NH$_2$ or NHR$^{N1}$, wherein R$^{N1}$ is, independently, OH, NO$_2$, NH$_2$, NR$^{N2}$$_2$, SO$_2$OR$^{N2}$, SO$_2$R$^{N2}$, SOR$^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each R$^{N2}$ can be H, C$_{1-20}$ alkyl (e.g., C$_{1-6}$ alkyl), or C$_{6-10}$ aryl.

The term "aryl" refers to an aromatic mono- or polycyclic radical of 6 to 12 carbon atoms having at least one aromatic ring. Examples of such groups include, but are not limited to, phenyl, naphthyl, 1,2,3,4-tetrahydronaphthalyl, 1,2-dihydronaphthalyl, indanyl, and 1H-indenyl.

The "arylalkyl" group, which as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as $C_{6-10}$ aryl $C_{1-6}$ alkyl, $C_{6-10}$ aryl $C_{1-10}$ alkyl, or $C_{6-10}$ aryl $C_{1-20}$ alkyl). In some embodiments, the alkylene and the aryl each can be further substituted with 1, 2, 3, or 4 substituent groups as defined herein for the respective groups.

The alkyl, carbocyclic, and aryl groups may be substituted or unsubstituted. When substituted, there will generally be, for example, 1 to 4 substituents present. These substituents may optionally form a ring with the alkyl, carbocyclic, or aryl group with which they are connected. Substituents may include, for example: carbon-containing groups such as alkyl, aryl, arylalkyl (e.g., substituted and unsubstituted phenyl, substituted and unsubstituted benzyl); halogen atoms and halogen-containing groups such as haloalkyl (e.g., trifluoromethyl); oxygen-containing groups such as alcohols (e.g., hydroxyl, hydroxyalkyl, aryl(hydroxyl)alkyl), ethers (e.g., alkoxy, aryloxy, alkoxyalkyl, alkoxyheterocyclyl, aryloxyalkyl, more preferably, for example, methoxy and ethoxy), aldehydes (e.g., carboxaldehyde), ketones (e.g., alkylcarbonyl, alkylcarbonylalkyl, arylcarbonyl, arylalkylcarbonyl, arylcarbonylalkyl), acids (e.g., carboxy, carboxyalkyl), acid derivatives such as esters (e.g., alkoxycarbonyl, alkoxycarbonylalkyl, alkylcarbonyloxy, alkylcarbonyloxyalkyl), amides (e.g., aminocarbonyl, mono- or di-alkylaminocarbonyl, aminocarbonylalkyl, mono- or di-alkylaminocarbonylalkyl, arylaminocarbonyl), carbamates (e.g., alkoxycarbonylamino, aryloxycarbonylamino, aminocarbonyloxy, mono- or di-alkylaminocarbonyloxy, arylminocarbonloxy) and ureas (e.g., mono- or di-alkylaminocarbonylamino or arylaminocarbonylamino); nitrogen-containing groups such as amines (e.g., amino, mono- or di-alkylamino, aminoalkyl, mono- or di-alkylaminoalkyl), azides, nitriles (e.g., cyano, cyanoalkyl), nitro; sulfur-containing groups such as thiols, thioethers, sulfoxides and sulfones (e.g., alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); heterocyclyl heteroalkyl groups, and heterocyclic groups containing one or more heteroatoms, (e.g., thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "azido" represents an —N3 group, which can also be represented as —N=N=N.

The terms "carbocyclic" and "carbocyclyl," as used herein, refer to an optionally substituted non-aromatic $C_{3-12}$ monocyclic, bicyclic, or tricyclic structure in which the rings are formed by carbon atoms. Carbocyclic structures include cycloalkyl, cycloalkenyl, and cycloalkynyl groups.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, and indanyl.

In a preferred embodiment, the "cycloalkyl" moieties can optionally be substituted with one, two, three or four substituents. Each substituent can independently be, alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, and optionally substituted cycloheptyl, or those which are specifically exemplified herein.

The term "cyano," as used herein, represents a —CN group.

As used herein, the term "halo" or "halogen" means a fluorine (fluoro), chlorine (chloro), bromine (bromo) or iodine (iodo) radical.

The term "heteroalkyl," as used herein, refers to an alkyl group, as defined herein, in which one or more of the constituent carbon atoms have each been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O—; and "alkoyl" which, as used herein, refers to alkyl-CO—. Alkoxy substituent groups or alkoxy-containing substituent groups may be substituted by, for example, one or more alkyl groups.

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of heteroaryl groups are benzooxazolyl, benzoimidazolyl, and benzothiazolyl.

The term "heterocycle" or "heterocyclyl" denotes a mono- or polycyclic alkyl ring, wherein one, two or three of the carbon ring atoms is replaced by a heteroatom such as N, O or S. Examples of hetereocyclyl groups include, but are not limited to, morpholinyl, thiomorpholinyl, piperazinyl, piperidinyl, pyrrolidinyl, tetrahydropyranyl, tetrahydrofuranyl, and 1,3-dioxanyl. The heterocyclyl groups may be unsubstituted or substituted, and attachment may be through their carbon frame or through their heteroatom(s) where appropriate.

The term "heterocyclyl heteroalkyl" refers to a heterocyclic group, as defined herein, attached to the parent molecular group through a heteroalkyl group (e.g., an ether or alkoxy group). An example of a heterocyclyl heteroalkyl group is —OCH$_2$CH$_2$(morpholino) group.

The heterocyclyl and heteroaryl groups described above may be substituted independently with one, two, three, or more substituents. Substituents may include, for example: carbon-containing groups such as alkyl, aryl, arylalkyl (e.g., substituted and unsubstituted phenyl, substituted and unsubstituted benzyl); halogen atoms and halogen-containing groups such as haloalkyl (e.g., trifluoromethyl); oxygen-containing groups such as alcohols (e.g., hydroxyl, hydroxyalkyl, aryl(hydroxyl)alkyl), ethers (e.g., alkoxy, aryloxy, alkoxyalkyl, aryloxyalkyl), aldehydes (e.g., carboxaldehyde), ketones (e.g., alkylcarbonyl, alkylcarbonylalkyl, arylcarbonyl, arylalkylcarbonyl, arylcarbonylalkyl), acids (e.g., carboxy, carboxyalkyl), acid derivatives such as esters (e.g., alkoxycarbonyl, alkoxycarbonylalkyl, alkylcarbonyloxy, alkylcarbonyloxyalkyl), amides (e.g., aminocarbonyl, mono- or di-alkylaminocarbonyl, aminocarbonylalkyl, mono- or di-alkylaminocarbonylalkyl, arylaminocarbonyl), carbamates (e.g., alkoxycarbonylamino, aryloxycarbonylamino, aminocarbonyloxy, mono- or di-alkylaminocarbonyloxy, arylminocarbonloxy) and ureas (e.g., mono- or di-alkylaminocarbonylamino or arylaminocarbonylamino); nitrogen-containing groups such as amines (e.g., amino, mono- or di-alkylamino, aminoalkyl, mono- or di-alkylaminoalkyl), azides, nitriles (e.g., cyano, cyanoalkyl), nitro; sulfur-containing groups such as thiols, thioethers, sulfoxides and sulfones (e.g., alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g., thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazolyl and carbolinyl).

The term "hydroxyl," as used herein, represents an —OH group. In some embodiments, the hydroxyl group can be substituted with a O-protecting group as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," $3^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, alkaryl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," $3^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, and pivaloyl; optionally substituted arylcarbonyl groups, such as benzoyl; silyl groups, such as trimethylsilyl (TMS), tert-butyldimethylsilyl (TBDMS), tri-iso-propylsilyloxymethyl (TOM), and triisopropylsilyl (TIPS); ether-forming groups with the hydroxyl, such methyl, methoxymethyl, tetrahydropyranyl, benzyl, p-methoxybenzyl, and trityl; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, and methyloxycarbonyl; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, and 3-methyl-2-butenoxycarbonyl; haloalkoxycarbonyls, such as 2-chloroethoxycarbonyl, 2-chloroethoxycarbonyl, and 2,2,2-trichloroethoxycarbonyl; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxy-carbonyl, and fluorenylmethyloxycarbonyl; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, and 2-chloro-4-nitrophenoxycarbonyl); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, and 1,3-dioxolane; acylal groups; and dithiane groups, such as 1,3-dithianes, and 1,3-dithiolane); carboxylic acid-protecting groups (e.g., ester groups, such as methyl ester, benzyl ester, t-butyl ester, and orthoesters; and oxazoline groups.

The term "perfluoroalkyl," as used herein, represents alkyl group, as defined herein, where each hydrogen radical bound to the alkyl group has been replaced by a fluoride radical. For example, perfluoroalkyl groups are exemplified by trifluoromethyl and pentafluoroethyl.

The term "sulfonyl," as used herein, represents an —$S(O)_2$— group.

Compounds of the invention can have one or more asymmetric carbon atoms and can exist in the form of optically pure enantiomers, mixtures of enantiomers such as racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as chiral chromatography and separation methods based thereon. The appropriate technique and/or method for separating an enantiomer of a compound described herein from a racemic mixture can be readily determined by those of skill in the art. "Racemate" or "racemic mixture" means a mixture containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9%) by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

Definitions

The term "effective amount" of an agent, as used herein, is that amount sufficient to effect beneficial or desired results, such as clinical results, and, as such, an "effective amount" depends upon the context in which it is being applied. For example, in the context of administering an agent that is an antimalarial agent, an effective amount of an agent is, for example, an amount sufficient to achieve alleviation or amelioration of one or more symptoms or conditions; diminishment of extent of disease, disorder, or condition; stabilized (i.e., not worsening) state of disease, disorder, or condition; preventing spread of disease, disorder, or condition (e.g., preventing the spread of *Plasmodium* infection beyond the liver, preventing systemic disease, preventing the symptomatic stage of malaria, preventing establishment of *Plasmodium* infection and/or preventing further spread of the disease by preventing transmission back to the mosquito); delay or slowing the progress of the disease, disorder, or condition; amelioration or palliation of the disease, disorder, or condition; and remission (whether partial or total), whether detectable or undetectable, as compared to the response obtained without administration of the agent.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein (see below).

Useful pharmaceutical carriers for the preparation of the compositions hereof, can be solids, liquids, or gases. Thus, the compositions can take the form of tablets, pills, capsules, suppositories, powders, enterically coated or other protected formulations (e.g., binding on ion-exchange resins or packaging in lipid-protein vesicles), sustained release formulations, solutions, suspensions, elixirs, and aerosols. The carrier can be selected from the various oils including those of petroleum, animal, vegetable or synthetic origin, e.g., peanut oil, soybean oil, mineral oil, and sesame oil. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for administration to the recipient.

As used herein, the term "pharmaceutically acceptable salt" refers to salts of any of the compounds described herein that within the scope of sound medical judgment, are suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, dichloroacetate, digluconate, dodecylsulfate, ethanesulfonate, formate, fumarate, glucoheptonate, glutamate, glycerophosphate, hemisulfate, heptonate, hexanoate, hippurate, hydrobromide, hydrochloride, hydroiodide, 2-hydroxy-ethanesulfonate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative basic salts include alkali or alkaline earth metal salts include sodium, lithium, potassium, calcium, and magnesium, aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, caffeine, and ethylamine.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, may be receiving treatment in the future, or a human or animal that is under care by a trained professional for a particular disease or condition.

As used herein, and as well understood in the art, "to treat" a condition or "treatment" of the condition (e.g., the conditions described herein such as malaria) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition (e.g., preventing the spread of *Plasmodium* infection beyond the liver or preventing transmission back to the mosquito, preventing systemic disease, preventing the symptomatic stage of malaria, and/or preventing establishment of *Plasmodium* infection); delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "unit dosage form" refers to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, gelcap, and syrup (also see below).

Other features and advantages of the invention are described in the following detailed description, the drawings, and the claims.

DETAILED DESCRIPTION OF THE INVENTION

Figure 1:
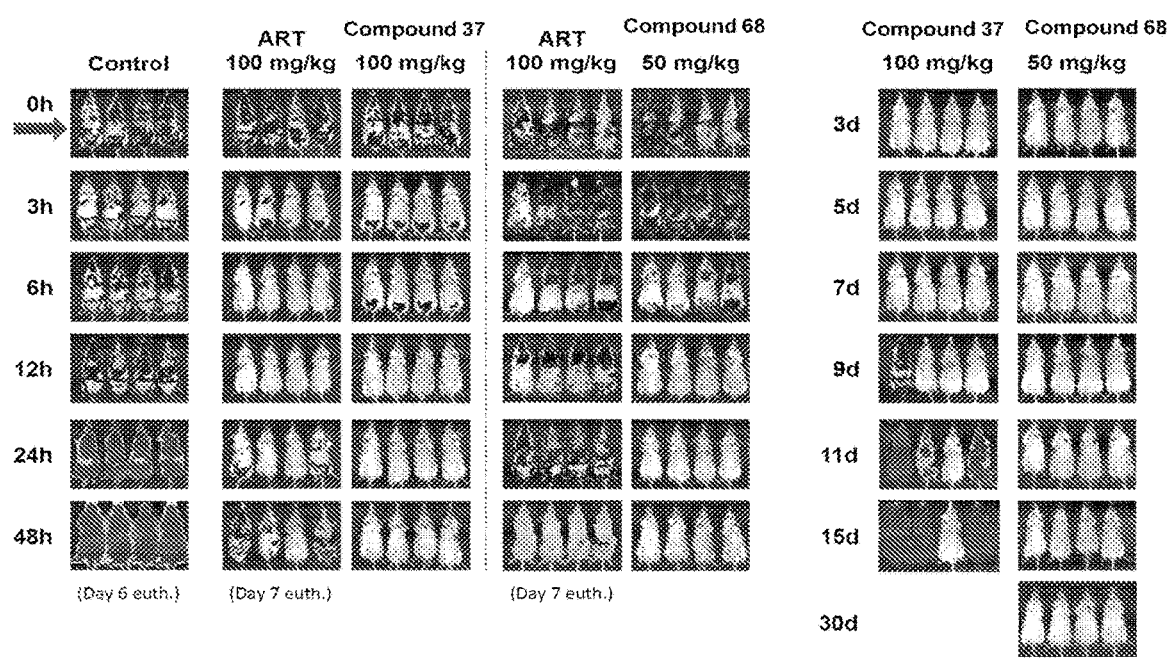
FIG. 1, Panel A, provides images of CD-1 mice inoculated with *P. berghei* blood stage parasites before treatment with the indicated compounds. A graphical representation of the results of this experiment is provided in FIG. 1, Panel B (see Example 4, below, for details).
Figure 1:
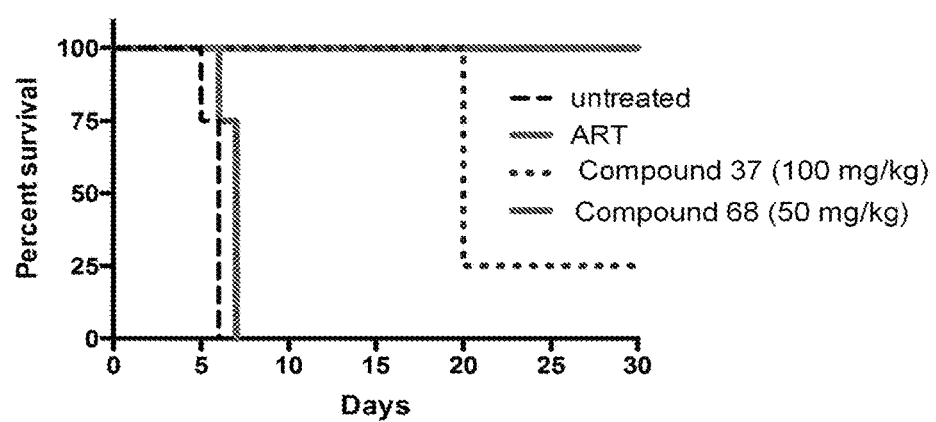

The present invention provides for novel compounds and pharmaceutical compositions useful for the treatment of malaria. The invention also provides methods of using these compounds and compositions, as well as related kits.

Utility and Administration

The compounds described herein are useful in the methods of the invention and, while not bound by any particular theory, are believed to exert their desirable effects through their ability to inhibit the growth of or kill a parasitic protozoan that causes malaria (e.g., *P. falciparum, P. vivax, P. ovale, P. malariae*, and/or *P. knowlesi*). In some embodiments, the treatment of malaria includes causative prophylaxis, such as preventing the spread of *Plasmodium* infection beyond the liver, preventing systemic disease, preventing the symptomatic stage of malaria, preventing the establishment of the infection, and/or preventing further transmission (e.g., to a mosquito). In some embodiments, the treatment of malaria refers to treatment intended to achieve cure (e.g., of *P. vivax* or *P. malariae*), e.g., treatment for radical cure (i.e., clearing hypnozoites from the liver). In various examples, the methods include preventing spread of infection of a malaria-causing parasite as described herein from the liver.

The compounds of the invention may be useful in the treatment of drug resistant malaria, such as malaria resistant to chloroquine, quinine, pyrimethamine, sulfadoxine, mefloquine, artemether, lumefantrine, artesunate, amodiaquine, dihydroartemisinin, piperaquine, proguanil, doxycycline, clindamycin, artemisinin, atovaquone, and any combination thereof.

For use in the methods of the invention, the compounds of the invention can be formulated as pharmaceutical or veterinary compositions. The formulation selected can vary depending on the subject to be treated, the mode of administration, and the type of treatment desired (e.g., prevention, prophylaxis, or therapy). A summary of formulation techniques is found in *Remington: The Science and Practice of Pharmacy*, 21$^{st}$ Edition, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference. Exemplary routes of administration and formulations are described as follows.

In the practice of the methods of the invention, the compounds (or pharmaceutically acceptable salts thereof) or compositions of the invention can be administered by any of the usual and acceptable routes and methods known in the art. The compounds or compositions can thus be administered, for example, by the enteral or gastrointestinal route (e.g., orally or rectally), topically (e.g., to the skin or an accessible mucous membrane (e.g., an intraoral (e.g., sublingual or buccal), intranasal, intrarectal, or genitourinary surface)), parenterally (e.g., by intramuscular, intravenous, subcutaneous, intraarticular, intravesicular, intrathecal, epidural, ocular, or aural application or injection), transdermally, or by inhalation (e.g., by aerosol).

The compositions can be in the form of a solid, liquid, or gas, as determined to be appropriate by those of skill in the art. Thus, as general examples, the pharmaceutical compositions may be in the form of tablets, capsules, syrups, pills, enterically coated or other protected formulations, sustained release formulations, elixirs, powders, granulates, suspensions, emulsions, solutions, gels (e.g., hydrogels), pastes, ointments, creams, plasters, transdermal patches, drenches, suppositories, enemas, injectables, implants, sprays, or aerosols.

The compositions of the invention, in general, include an effective amount of a compound described herein and one or more pharmaceutically acceptable carriers or excipients, as is well known in the art. The compositions can thus include one or more diluents, buffers, preservatives, salts, carbohydrates, amino acids, carrier proteins, fatty acids, lipids, etc. The compounds described herein may be present in amounts totaling, for example, 1-95% by weight of the total weight of the composition.

For injection, formulations can be prepared in conventional forms as liquid solutions or suspensions, or as solid forms suitable for solution or suspension in liquid prior to injection, or as emulsions. Suitable excipients for these formulations include, for example, water, saline, dextrose, and glycerol. Such compositions can also contain nontoxic auxiliary substances, such as wetting or emulsifying agents, and pH buffering agents, such as sodium acetate, sorbitan monolaurate, and so forth.

Formulations for oral use include tablets containing a compound of the invention in a mixture with one or more non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, and buffering agents.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The compounds and compositions of the invention can be packaged in a kit, optionally with one or more other pharmaceutical agents (see below). Non-limiting examples of the kits include those that contain, e.g., two or more pills, a pill and a powder, a suppository and a liquid in a vial, or two topical creams. The kits can include optional components that aid in the administration of the unit dose to subjects, such as vials for reconstituting powder forms, syringes for injection, customized IV delivery systems, or inhalers. Additionally, the unit dose kits can contain instructions for preparation and administration of the compositions. The kits can be manufactured as a single use unit dose for one subject, multiple uses for a particular subject (at a constant dose or in which the individual compounds may vary in potency as therapy progresses); or the kits can contain multiple doses suitable for administration to multiple subjects ("bulk packaging"). The kit components can be assembled in cartons, blister packs, bottles, and tubes.

The dose of a compound of the present invention depends on a number of factors, such as the manner of administration, the age and the body weight of the subject, and the condition of the subject to be treated, and ultimately will be decided by the attending physician or veterinarian. Such an amount of the compound, as determined by the attending physician or veterinarian, is referred to herein, and in the claims, as a "therapeutically effective amount." For example, the dose of a compound of the present invention is typically in the range of about 1 to about 1000 mg per day. Preferably, the therapeutically effective amount is in an amount of from about 1 mg to about 500 mg per day.

Administration of each drug, as described herein, can, independently, be one to four times daily for one day to one year, and may even be for the life of the subject. Chronic, long-term administration may be indicated.

Combination Therapies

The compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

Examples of other drugs to combine with the compounds described herein include pharmaceuticals for the treatment of malaria (e.g., chloroquine, quinine, pyrimethamine, sulfadoxine, mefloquine, artemether, lumefantrine, artesunate, amodiaquine, dihydroartemisinin, piperaquine, proguanil, doxycycline, clindamycin, artemisinin, atovaquone, any other therapeutic approved for the treatment of malaria, and any combination thereof). Other examples of drugs to combine with the compounds described herein include pharmaceuticals for the treatment of different, yet associated or related symptoms or indications. Combination methods can involve the use of the two (or more) agents formulated together or separately, as determined to be appropriate by those of skill in the art. In one example, two or more drugs are formulated together for the simultaneous or near simultaneous administration of the agents.

EXAMPLES

The following Examples illustrate the synthesis of a representative number of compounds and the use of these compounds in the treatment of malaria. Accordingly, the Examples are intended to illustrate but not to limit the invention. Additional compounds not specifically exemplified may be synthesized using conventional methods in combination with the methods described herein.

Example 1. Synthesis of Compounds

Materials and Methods

Compounds of the present invention can be prepared beginning with commercially available starting materials and utilizing general synthetic techniques and procedures known to those skilled in the art. Chemicals may be purchased from companies such as Aldrich, Argonaut Technologies, VWR, and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

Method A retention time method: UPLC-MS (Waters, Milford, Mass.). Mobile phase A consisted of either 0.1% ammonium hydroxide or 0.05% TFA in water, while mobile phase B consisted of the same additives in acetonitrile. The gradient ran from 5% to 95% mobile phase B over 0.8 min at 0.9 mL/min. An Acquity BEH C18, 1.7 μm, 2.1×50 mm column was used with column temperature maintained at 65° C.

Method B retention time method: UPLC-MS (Waters, Milford, Mass.). Mobile phase A consisted of either 0.1% ammonium hydroxide or 0.05% TFA in water, while mobile phase B consisted of the same additives in acetonitrile. The gradient ran from 5% to 95% mobile phase B over 2.65 min at 0.9 mL/min. An Acquity BEH C18, 1.7 μm, 2.1×50 mm column was used with column temperature maintained at 65° C.

The compounds of formula I can be prepared according to Schemes 1 to 15:
General synthetic scheme 1 shows how compounds for certain embodiments of the present invention can be prepared, such as compounds 1-4, 8, 10, 11-15, 17-20, 22-25, 27-30, 34, 36, 38, 40, 44, 45, 49-52, 54, 56, 59, 60, 63, 71, 72, 75, 78, 83, and 93:
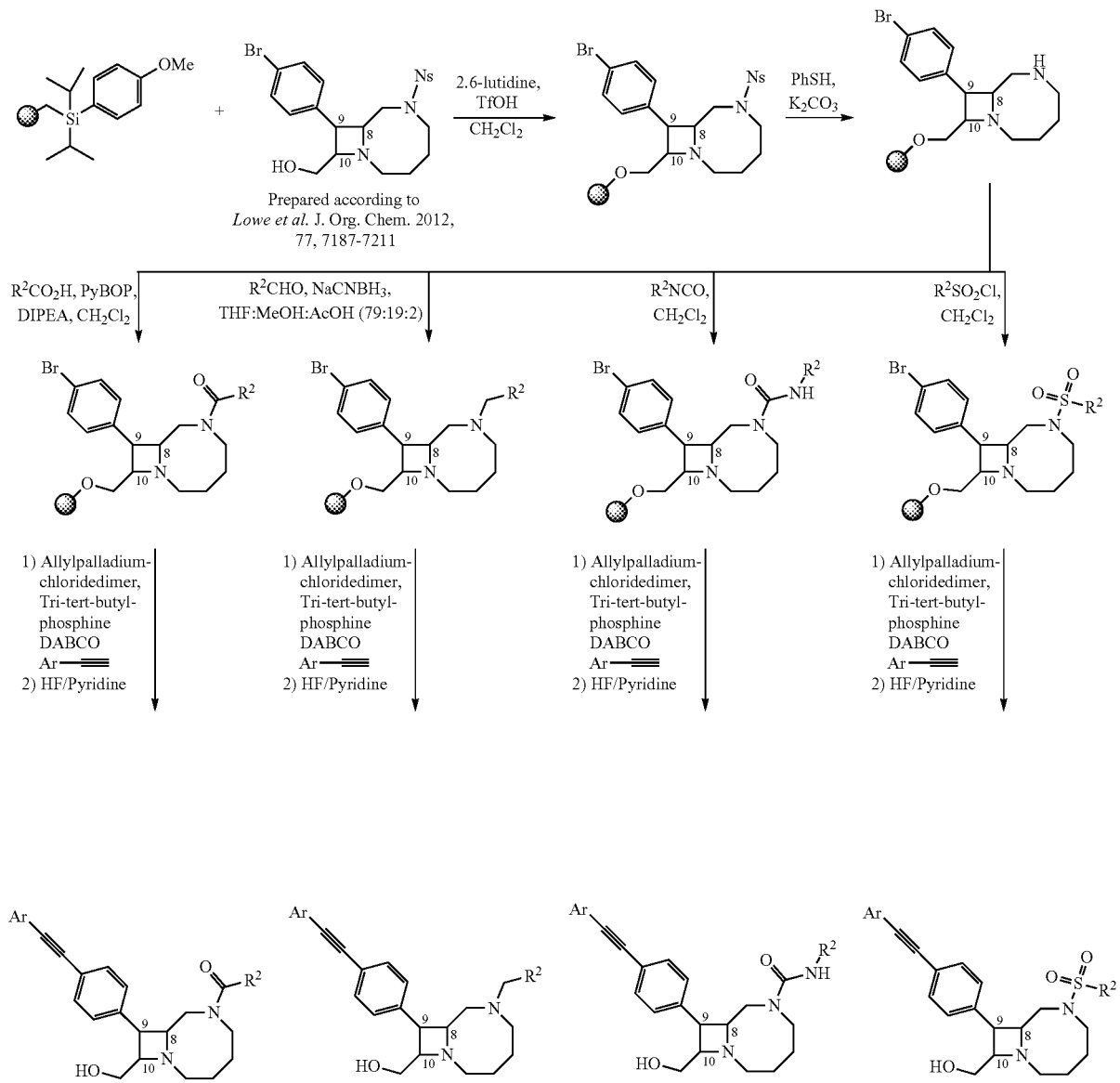
● = Solid support (SynPhase Lanterns)
Stereochemistry C8, C9, C10 =
R, R, S, or S, R, R, or S, S, R, or
R, S, R, or R, R, R, or R, S, S, or
S, S, S, or S, R, S General synthetic scheme 2 shows how compounds for certain embodiments of the present invention can be prepared, such as compound 74:

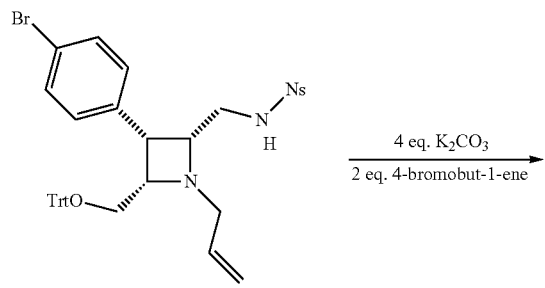

4 eq. K$_2$CO$_3$
2 eq. 4-bromobut-1-ene

Prepared according to
*Lowe et al.* J. Org. Chem.
2012, 77, 7187-7211

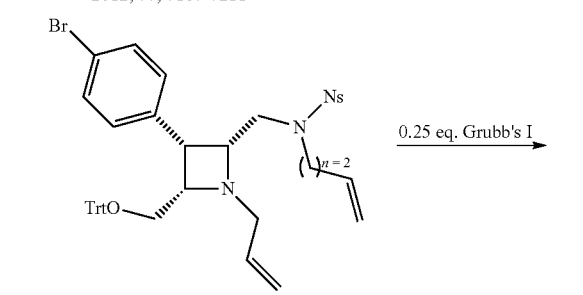

0.25 eq. Grubb's I

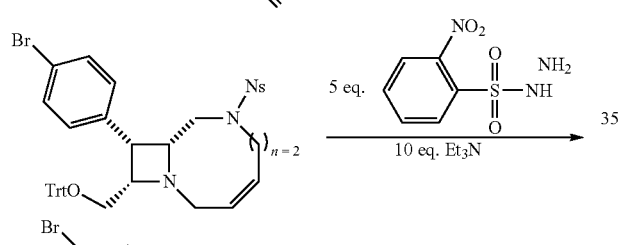

5 eq. 
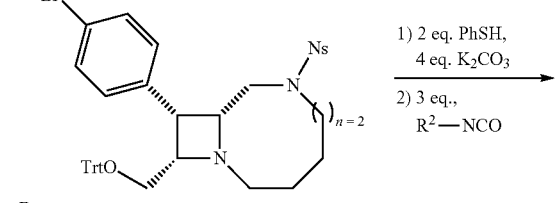
10 eq. Et$_3$N

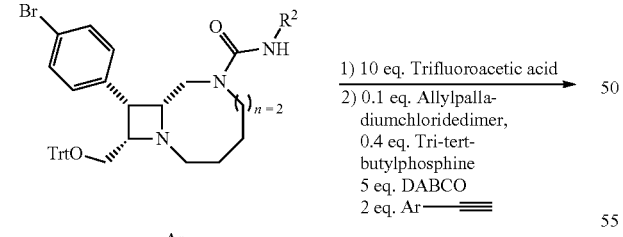

1) 2 eq. PhSH,
4 eq. K$_2$CO$_3$
2) 3 eq., R$^2$—NCO

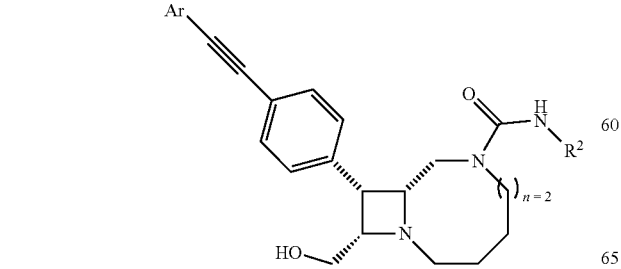

1) 10 eq. Trifluoroacetic acid
2) 0.1 eq. Allylpalladiumchloridedimer,
0.4 eq. Tri-tert-butylphosphine
5 eq. DABCO
2 eq. Ar—≡

General synthetic scheme 3 shows how compounds for certain embodiments of the present invention can be prepared, such as compound 47:

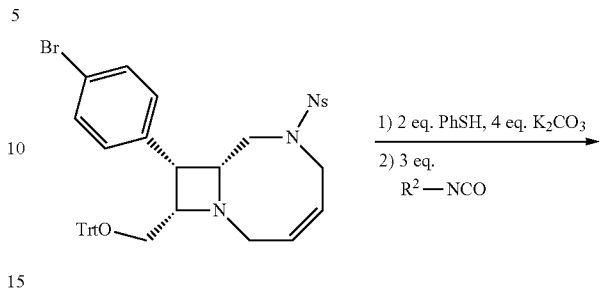

1) 2 eq. PhSH, 4 eq. K$_2$CO$_3$
2) 3 eq. R$^2$—NCO

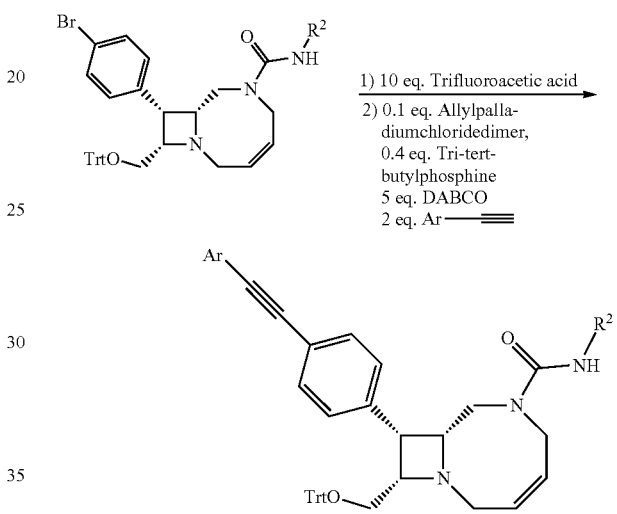

1) 10 eq. Trifluoroacetic acid
2) 0.1 eq. Allylpalladiumchloridedimer,
0.4 eq. Tri-tert-butylphosphine
5 eq. DABCO
2 eq. Ar—≡

General synthetic scheme 4 shows how compounds for certain embodiments of the present invention can be prepared, such as compound 31:

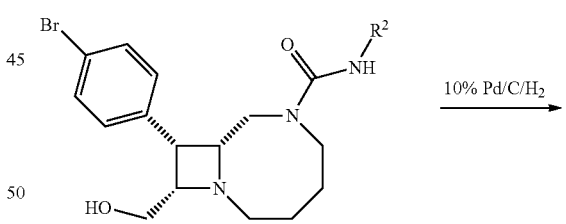

10% Pd/C/H$_2$

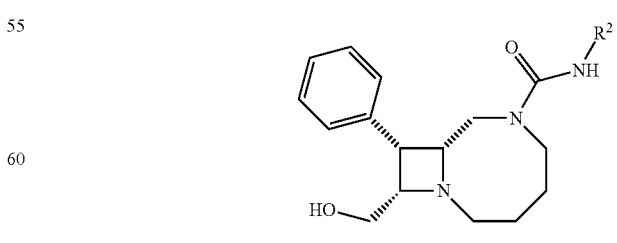

General synthetic scheme 5 shows how compounds for certain embodiments of the present invention can be prepared, such as compounds 32, 33, and 73:

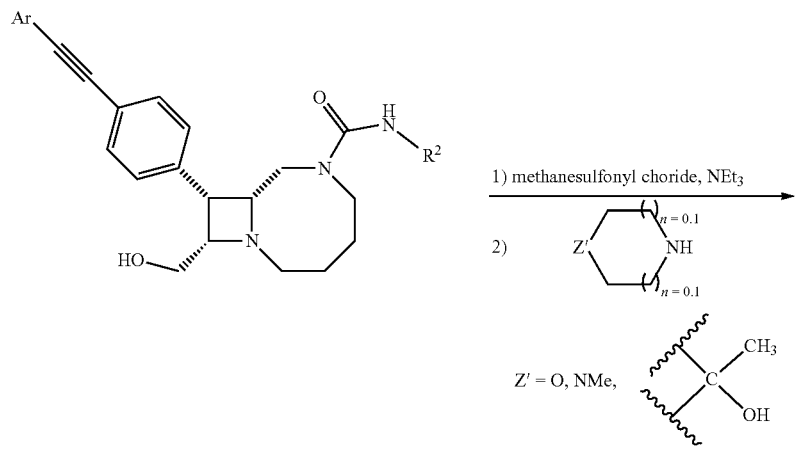
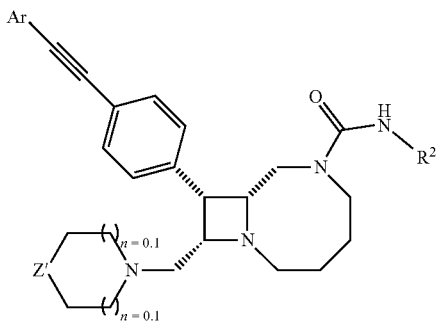
General synthetic scheme 6 shows how compounds for certain embodiments of the present invention can be prepared, such as compounds 35, 80, 85, or 86:
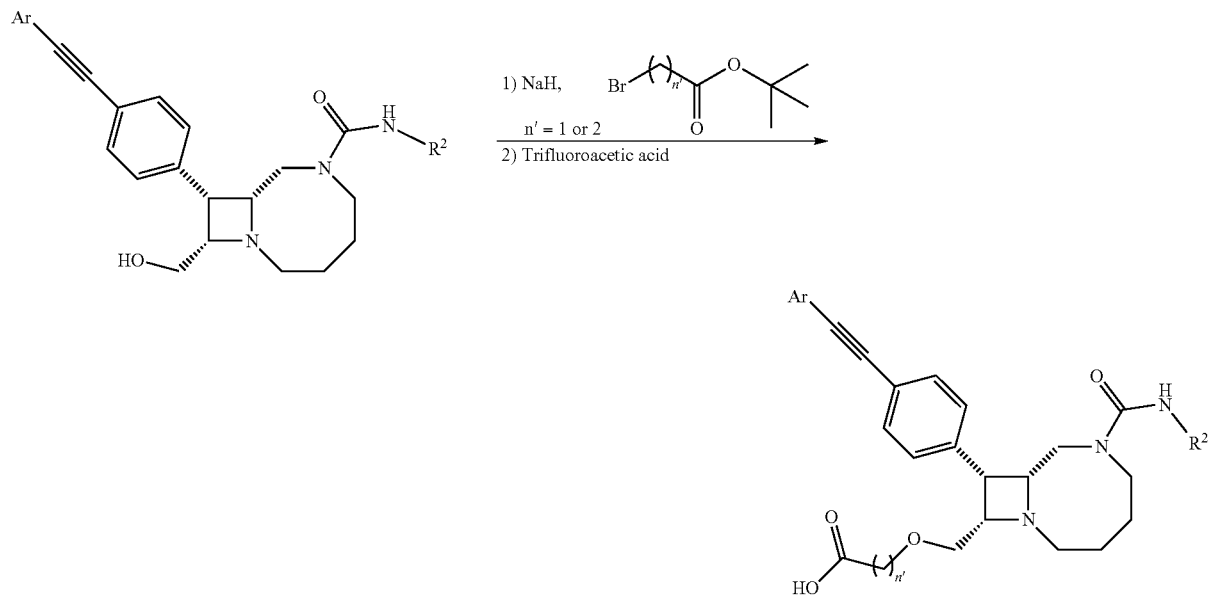

General synthetic scheme 7 shows how compounds for certain embodiments of the present invention can be prepared, such as compounds 34 and 79:
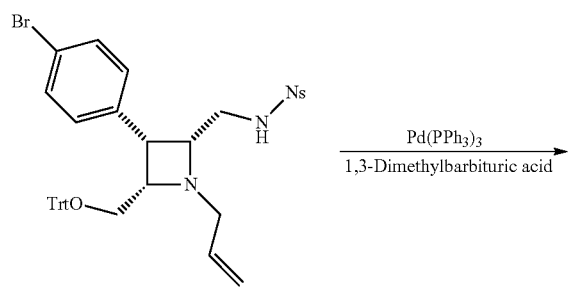
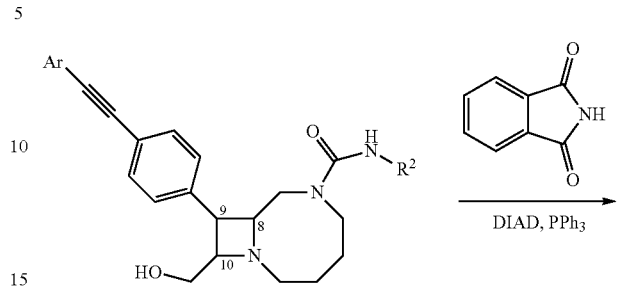
General synthetic scheme 8 shows how compounds for certain embodiments of the present invention can be prepared, such as compounds 37, 48, 55, 57, and 84:
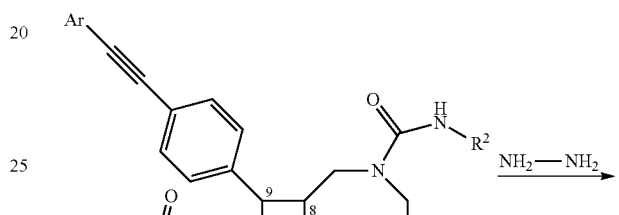
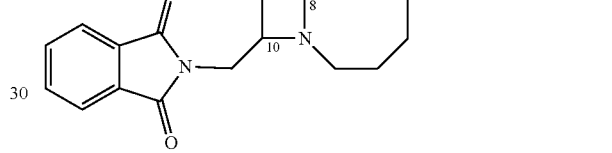
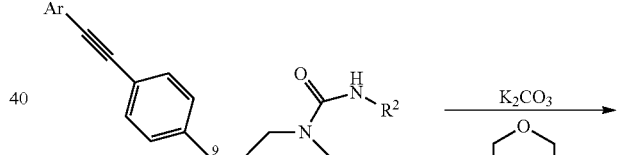
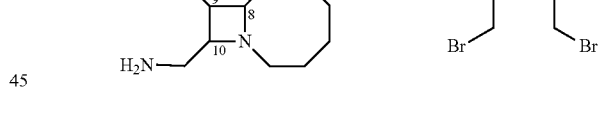
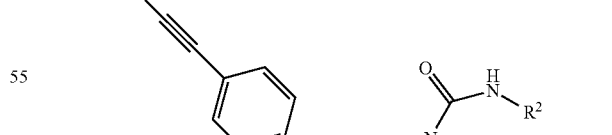
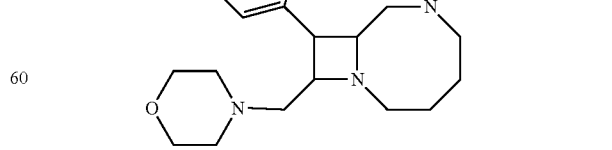
Stereochemistry C8, C9, C10 = R, S, S or R, R, S and R, S, R General synthetic scheme 9 shows how compounds for certain embodiments of the present invention can be prepared, such as compounds 39, 66, and 77:

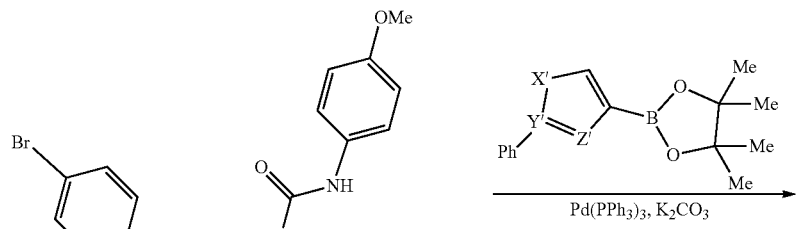

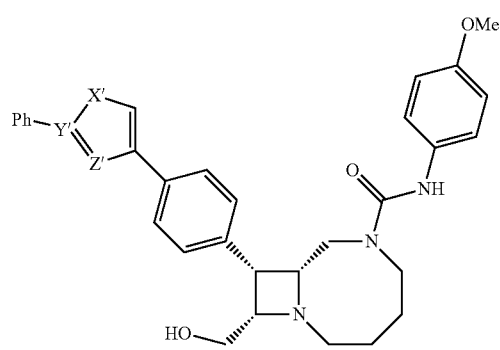

X' = NH, CH₂, S, or O
Y' and Z' = N or C

General synthetic scheme 10 shows how compounds for certain embodiments of the present invention can be prepared, such as compounds 5, 7, 9, 16, 21, 26, 41, 42, 46, 64, 67, and 69:

General synthetic scheme 11 shows how compounds for certain embodiments of the present invention can be prepared, such as compounds 43 and 70:

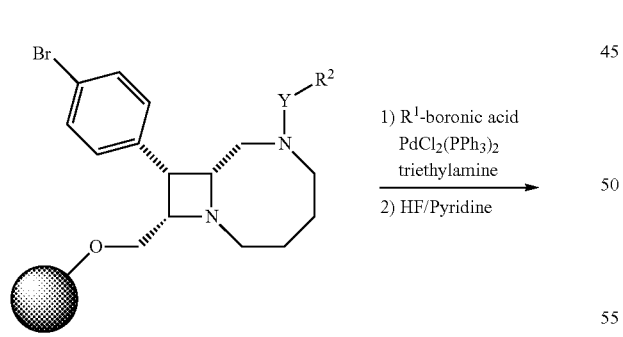

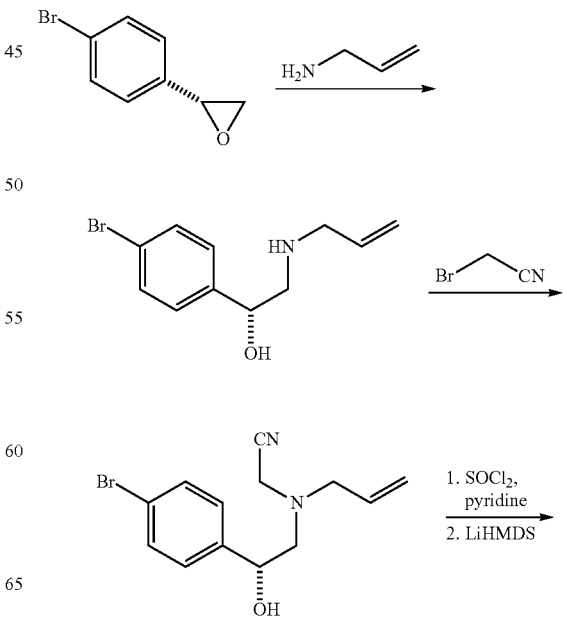

-continued

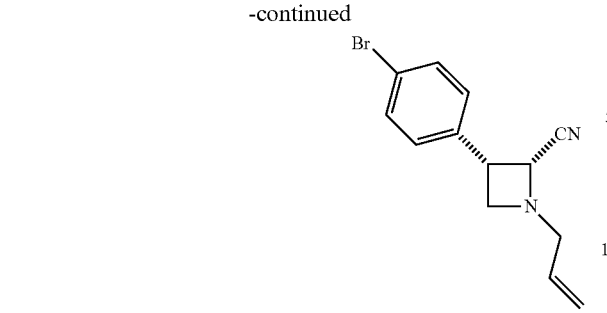

1) DIBAL
2) o-NsCl, 2,6-lutidine
3) K₂CO₃, allyl bromide

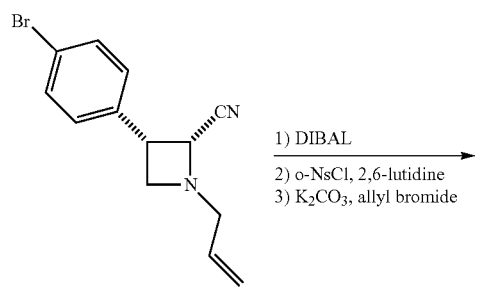

1) Grubbs I
2) 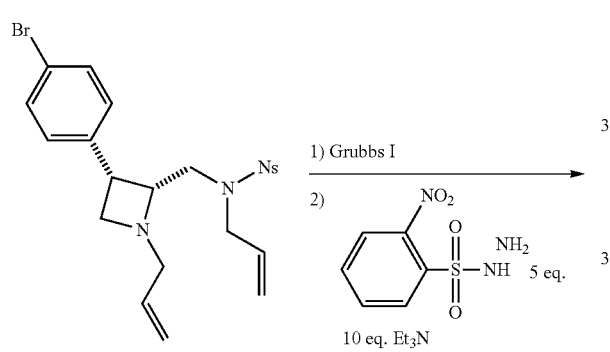 5 eq.
10 eq. Et₃N

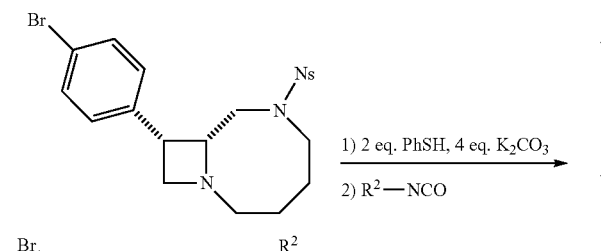

1) 2 eq. PhSH, 4 eq. K₂CO₃
2) R²—NCO

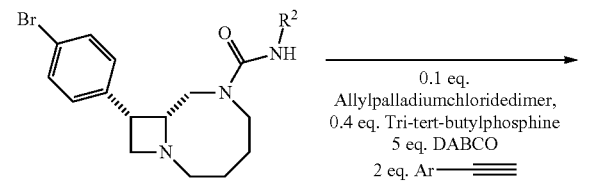

0.1 eq. Allylpalladiumchloridedimer,
0.4 eq. Tri-tert-butylphosphine
5 eq. DABCO
2 eq. Ar—≡

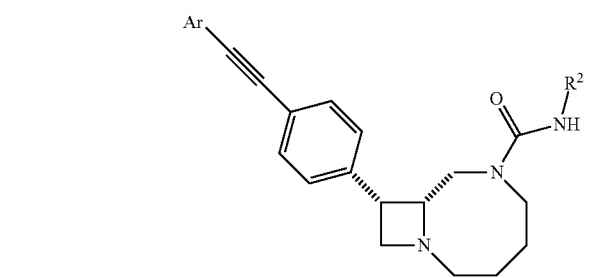

General synthetic scheme 12 shows how compounds for certain embodiments of the present invention can be prepared, such as compound 53:

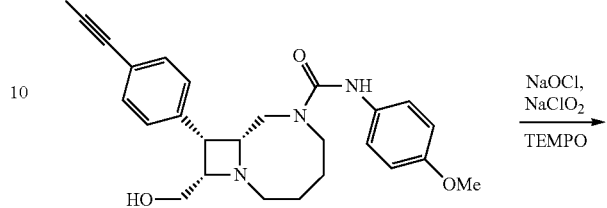

NaOCl, NaClO₂
TEMPO

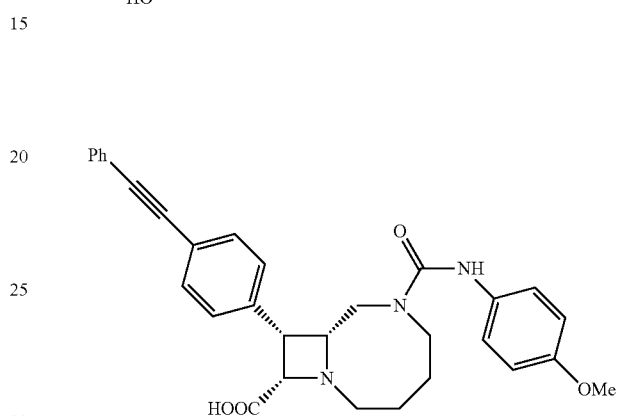

General synthetic scheme 13 shows how compounds for certain embodiments of the present invention can be prepared, such as compounds 58, 65, 76, and 82:

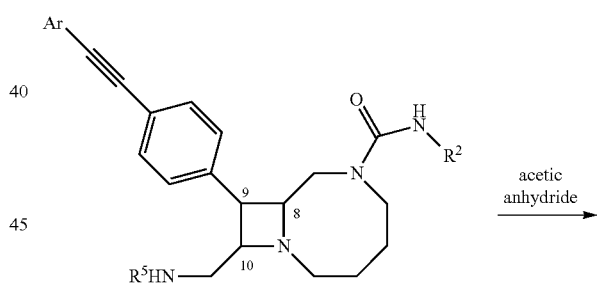

acetic anhydride

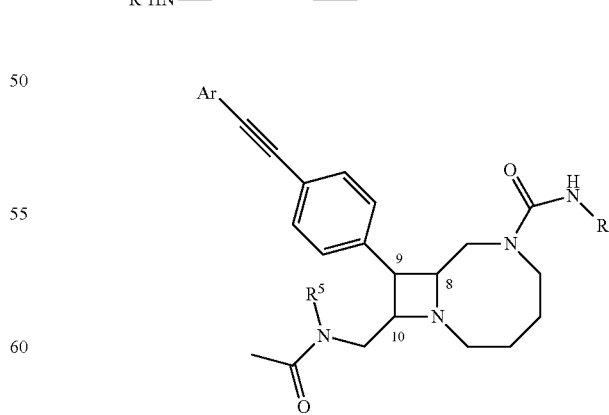

R⁵ = Me or H
Stereochemistry C8, C9, C10 = R, R, S and R, S, R

General synthetic scheme 14 shows how compounds for certain embodiments of the present invention can be prepared, such as compounds 61, 68, 88, and 92:
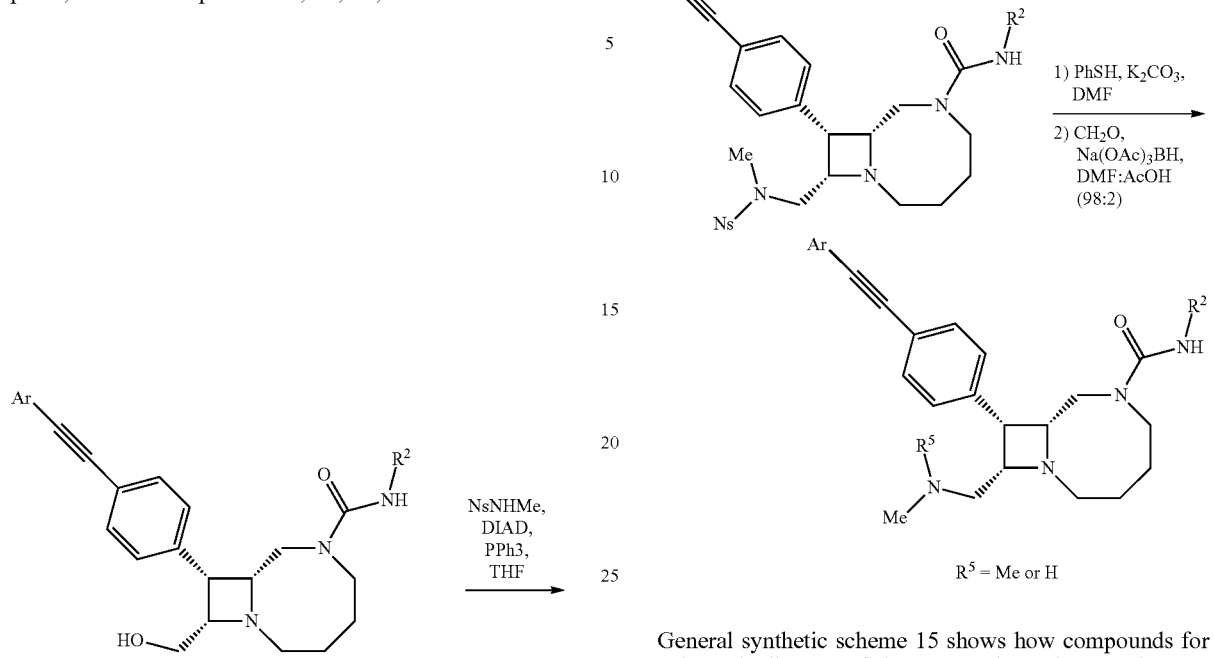
General synthetic scheme 15 shows how compounds for certain embodiments of the present invention can be prepared, such as compound 62:
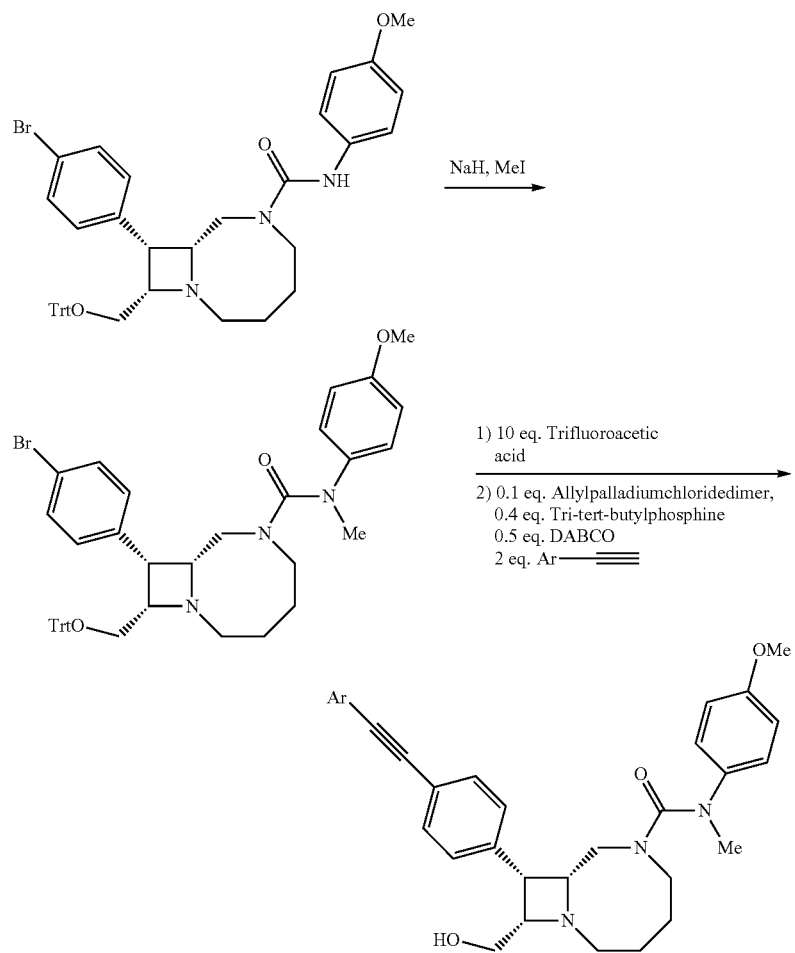

General synthetic scheme 16 shows how compounds for certain embodiments of the present invention can be prepared, such as compound 81:
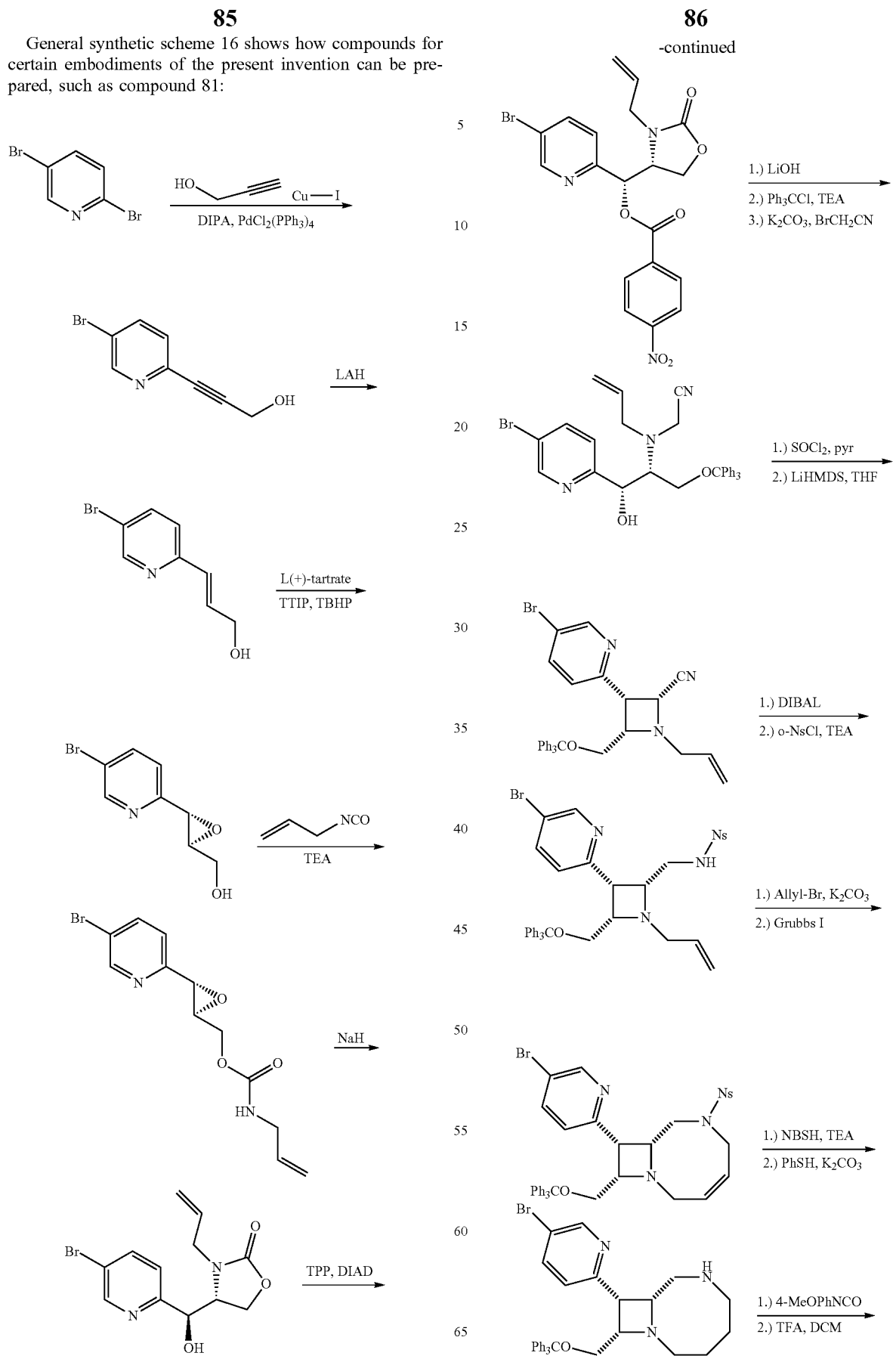

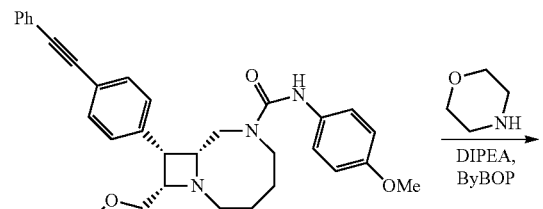

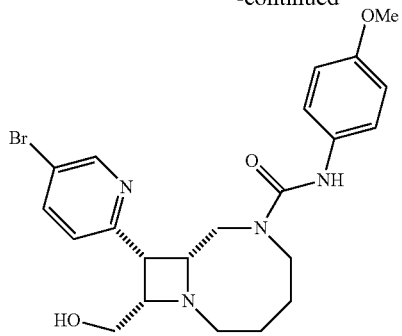

General synthetic scheme 17 shows how compounds for certain embodiments of the present invention can be prepared, such as compound 87:

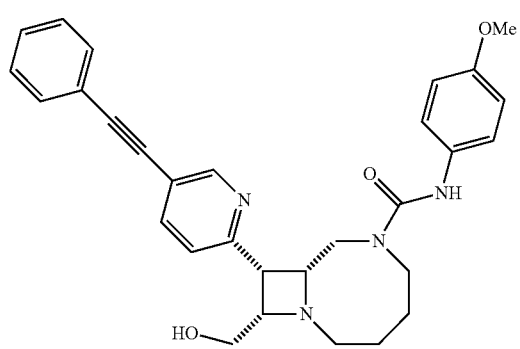

General synthetic scheme 18 shows how compounds for certain embodiments of the present invention can be prepared, such as compound 89:

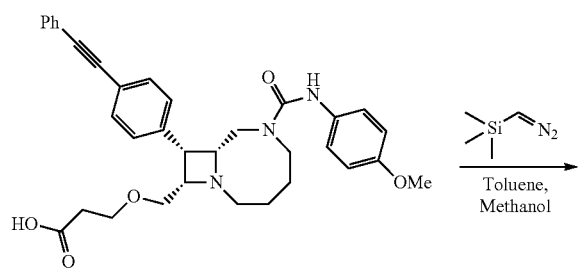

General synthetic scheme 19 shows how compounds for certain embodiments of the present invention can be prepared, such as compound 90:

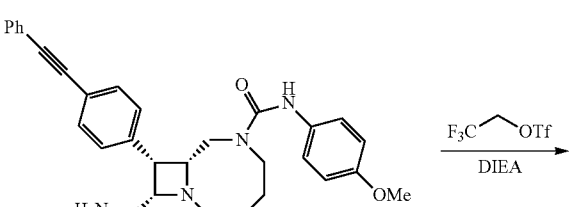

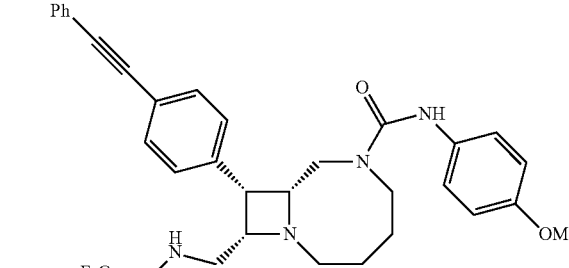

General synthetic scheme 20 shows how compounds for certain embodiments of the present invention can be prepared, such as compound 91:

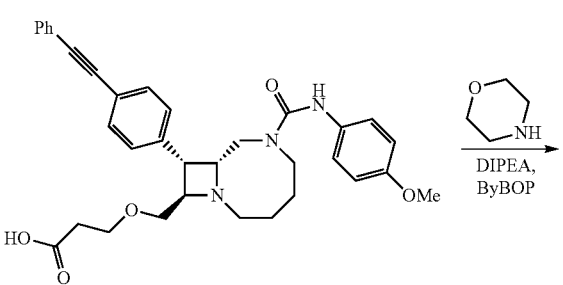

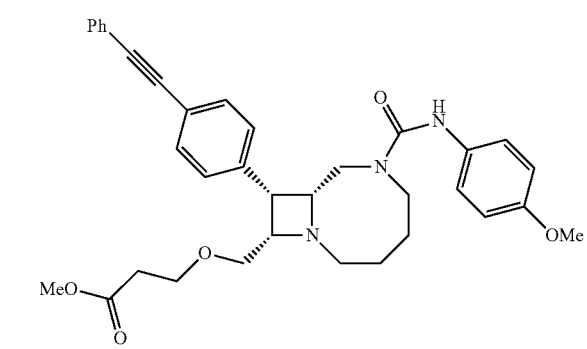

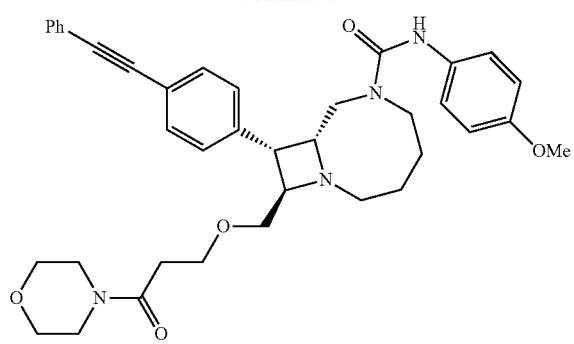

General synthetic scheme 21 shows how compounds for certain embodiments of the present invention can be prepared, such as compound 94:

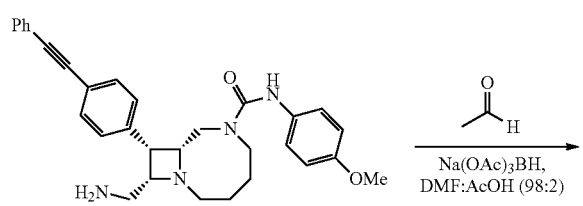

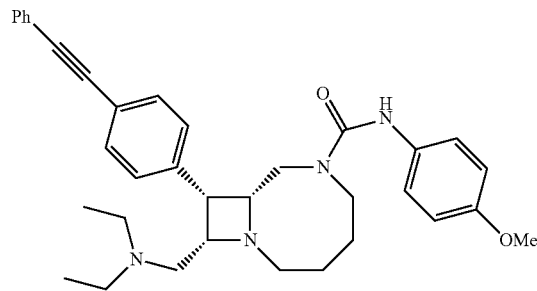

General synthetic scheme 22 shows how compounds for certain embodiments of the present invention can be prepared, such as compound 95:

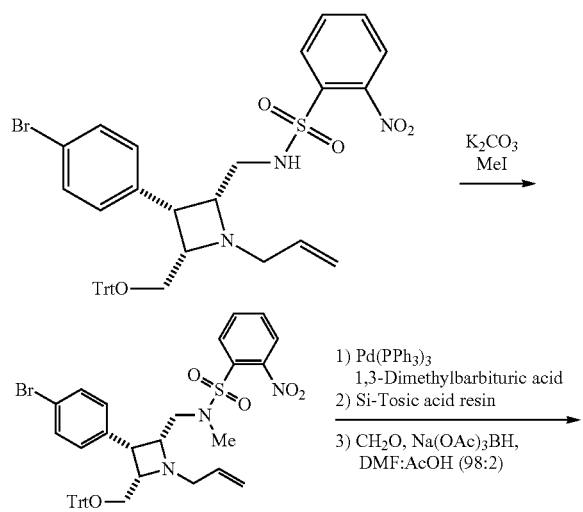

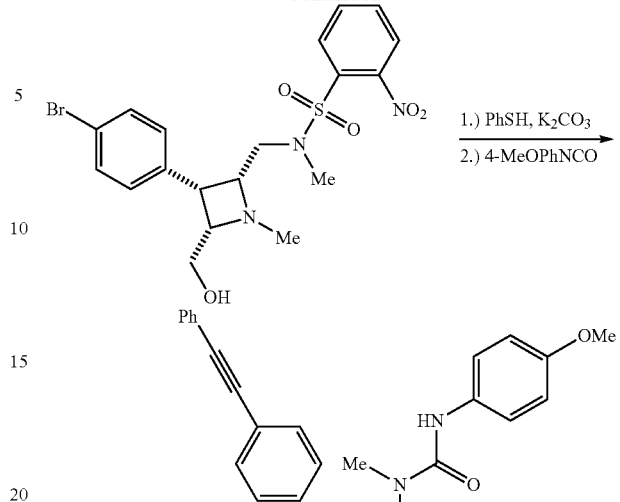

Synthesis of Compound 68

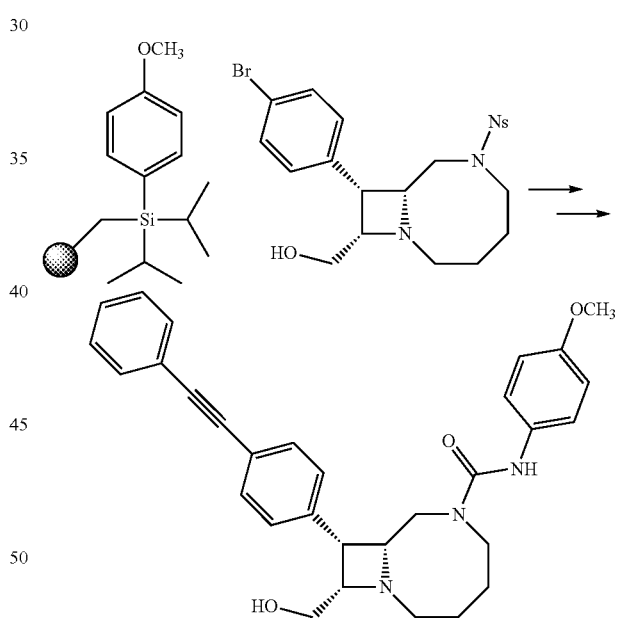

Loading of Lanterns ((8R,9R,10S)-9-(4-bromophenyl)-6-((2-nitrophenyl)sulfonyl)-1,6-diazabicyclo[6.2.0]decan-10-yl)methanol was prepared using the procedure of Lowe and coworkers (J. Org. Chem. 2012, 77, 7187-7211).

Solid-phase synthesis was conducted on silicon-functionalized polystyrene SynPhase Lanterns (L-series). 200 lanterns were dried under vacuum for 3 h then purged with nitrogen. Dichloromethane was added just to cover the lanterns, and 3% TfOH in DCM solution (40 mL) was added to the lanterns. The vial was capped and shaken for 10 min. During the shaking the color changed to dark red. All the liquids were removed using a syringe, and lutidine (3 mL)

was added. The flask was sealed and shaken for a few minutes. A solution of ((8R,9R,10S)-9-(4-bromophenyl)-6-((2-nitrophenyl)sulfonyl)-1,6-diazabicyclo[6.2.0]decan-10-yl)methanol (1837 mg, 3600 μmol) in anhydrous DCM (120 mL) was quickly added to the lanterns. The reaction flask was shaken for 4 days. The solution was removed, and the lanterns were washed with DCM and dried.

Nosyl Deprotection

Lanterns were suspended in DMF (0.8 mL/lantern), and then thiophenol (0.033 ml, 0.320 mmol) was added, followed by potassium carbonate (0.066 g, 0.480 mmol). The lanterns were shaken for 65 h at room temperature. Lanterns were filtered and washed with dichloromethane, THF, THF/isopropanol (3:1), THF/water (3:1), DMF, THF/water (3:1), THF/isopropanol (3:1) and THF.

Urea Capping

Dichloromethane (0.8 mL/lantern) was added to the lanterns, and 1-isocyanato-4-methoxybenzene (20 equiv) was added. The lanterns were shaken for 16 h at room temperature. Lanterns were filtered and washed with dichloromethane, THF, THF/isopropanol (3:1), THF/water (3:1), DMF, THF/water (3:1), THF/isopronaol (3:1) and THF.

Sonogashira Reaction

The lanterns were placed in a vial, and DME (0.8 mL/lantern) was added to this vial. A cap with a rubber septum was placed on the vial, and the vial was evacuated and purged with argon. Pd(PPh$_3$)$_4$ (2.0 eq), CuI (3.0 eq), ethynylbenzene (20 eq) and Et$_3$N (30 eq) were added to the vial. The lanterns were placed in a shaker for 5 days at 35° C. Lanterns were washed twice with DMF, THF/water (3:1), THF/isopropanol (3:1), and THF. A quarter lantern from each building block was cleaved by the procedure described below and analyzed by HPLC. Lanterns were re-subjected to the reaction conditions once more if the unreacted starting material was detected.

Cleavage Protocol

Lanterns were taken in a vial, and 15% solution of HF/pyridine in stabilized THF (350 μL/Lantern) was added. After 2 h the cleavage solution was quenched with TMSOMe (700 μL/lantern). The samples were concentrated on a Genevac® solvent evaporation system overnight without heating. Purification was accomplished via SiO2 chromatography to yield (8R,9R,10S)-10-(hydroxymethyl)-N-(4-methoxyphenyl)-9-(4-(phenylethynyl)phenyl)-1,6-diazabicyclo[6.2.0]decane-6-carboxamide (89% yield). $^1$H NMR (300 MHz, CDCl$_3$) δ 7.50-7.42 (m, 2H), 7.44-7.34 (m, 4H), 7.31-7.24 (m, 3H), 7.17 (d, J=8.8 Hz, 2H), 6.75 (d, 8.8 2H), 6.05 (s, 1H), 3.85-3.72 (m, 1H), 3.70 (s, 3H), 3.65-3.46 (m, 5H), 3.46-3.35 (m, 1H), 3.30-3.15 (m, 1H), 3.01-2.90 (m, 1H), 2.86-2.74 (m, 1H), 2.44-2.29 (m, 1H), 1.82-1.65 (m, 2H), 1.64-1.48 (m, 2H). MS (ESI) calcd for C$_{31}$H$_{34}$N$_3$O$_3$ [M+H]+: 496.25 Found: 496.48.

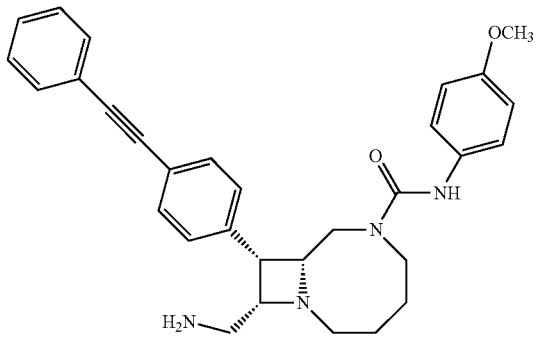

In a flame dried flask under argon a solution of triphenylphosphine (772 mg, 2.94 mmol) in THF (14.7 ml) at 0° C. was slowly added (E)-diisopropyl diazene-1,2-dicarboxylate (572 μl, 2.94 mmol). After 5 min the mixture became milky yellow. Then 4.48 mL of the prepared mixture (DIAD+PPh$_3$+THF) (0.896 mmol) was added to the flask containing (8R,9R,10S)-10-(hydroxymethyl)-N-(4-methoxyphenyl)-9-(4-(phenylethynyl)phenyl)-1,6-diazabicyclo[6.2.0]decane-6-carboxamide (126 mg, 0.254 mmol) and phtalimide (56.1 mg, 0.381 mmol) in THF (500 μL) at 0° C. The mixture was stirred for 2 h and was then concentrated and purified by silica chromatography to yield (8R,9R,10S)-10-(hydroxymethyl)-N-(4-methoxyphenyl)-9-(4-(phenylethynyl)phenyl)-1,6-diazabicyclo[6.2.0]decane-6-carboxamide (67% yield) which was used directly in the subsequent step. (8R,9S,10S)-10-((2,5-dioxopyrrolidin-1-yl)methyl)-N-(4-methoxyphenyl)-9-(4-(phenylethynyl)phenyl)-1,6-diazabicyclo[6.2.0]decane-6-carboxamide was dissolved in ethanol (1.85 ml), to this was added methylhydrazine (98 μl, 1.857 mmol), and the reaction mixture was stirred at 80° C. during 3 h. The reaction mixture was concentrated. Purification was accomplished via SiO$_2$ chromatography to yield (8R,9S,10S)-10-(aminomethyl)-N-(4-methoxyphenyl)-9-(4-(phenylethynyl)phenyl)-1,6 diazabicyclo[6.2.0]decane-6-carboxamide (46% yield). $^1$H NMR (400 MHz, CDCl$_3$) δ 7.55-7.38 (m, 5H), 7.30-7.22 (m, 3H), 7.22-7.12 (m, 3H), 6.81-6.64 (m, 2H), 6.05 (s, 1H), 3.84-3.73 (m, 1H), 3.69 (s, 3H), 3.61-3.51 (m, 2H), 3.50-3.43 (m, 1H), 3.41-3.36 (m, 1H), 3.26-3.24 (m, 2H), 2.97-2.85 (m, 1H), 2.85-2.76 (m, 1H), 2.76-2.68 (m, 1H), 2.33-2.23 (m, 1H), 1.79-1.65 (m, 2H), 1.62-1.50 (m, 2H). MS (ESI) calcd for C$_{31}$H$_{35}$N$_4$O$_2$ [M+H]+: 495.27, Found: 495.49.

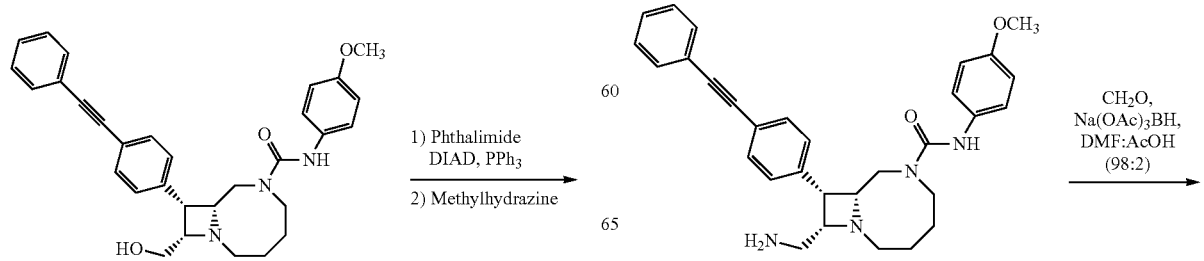

-continued

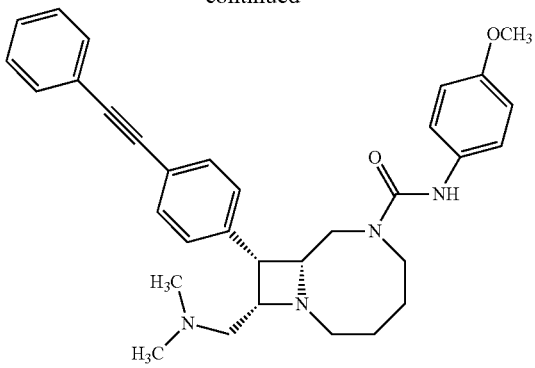

To (8R,9S,10S)-10-(aminomethyl)-N-(4-methoxyphenyl)-9-(4-(phenylethynyl)phenyl)-1,6-diazabicyclo[6.2.0]decane-6-carboxamide (150 mg, 0.303 mmol) in DCM (5 mL) under Ar was added magnesium sulfate (365 mg, 3.03 mmol) followed by formaldehyde (135 µl, 1.820 mmol). Anhydrous sodium triacetoxyhydroborate (900 mg, 4.25 mmol) was then added, and the reaction was stirred for 2 h. Sodium bicarbonate solution was then added, and the reaction was stirred for 15 minutes and then extracted with DCM (3×). The reaction mixture was concentrated. Purification was accomplished via $SiO_2$ chromatography to yield (8R,9S,10S)-10-((dimethylamino)methyl)-N-(4-methoxyphenyl)-9-(4-(phenylethynyl)phenyl)-1,6-diazabicyclo[6.2.0]decane-6-carboxamide (73% yield)$^1$H NMR (300 MHz, $CDCl_3$) δ 7.59-7.42 (m, 5H), 7.41-7.32 (m, 3H), 7.30-7.22 (m, 3H), 6.91-6.77 (m, 2H), 6.13 (s, 1H), 3.94-3.82 (m, 1H), 3.79 (s, 3H), 3.71-3.43 (m, 4H), 3.31-3.16 (m, 1H), 3.12-2.99 (m, 1H), 2.95-2.80 (m, 1H), 2.56-2.43 (m, 2H), 2.40-2.27 (m, 1H), 2.08 (s, 6H), 1.91-1.71 (m, 3H), 1.72-1.55 (m, 1H). MS (ESI) calcd for $C_{33}H_{39}N_4O_2$ [M+H]+: 523.299, Found: 523.63.

Example 2. Activity of Selected Compounds Against the Dd2 Strain of *P. falciparum*

The Dd2 strain of *P. falciparum* was cultured in complete medium (RPMI with L-glutamine, 4.3% heat-inactivated O-positive human serum, 2.08 mg/ml albumax, 0.013 mg/ml hypoxanthine, 1.17 mg/ml glucose, 0.18% $NaHCO_3$, 0.031 M Hepes, 2.60 mM NaOH, and 0.043 mg/ml gentamicin) until the parasitemia reached 3-8%. Parasitemia was determined by checking at least 500 red blood cells from a Giemsa-stained blood smear. The Dd2 cultures along with tested O-positive red blood cells were centrifuged at room temperature at 2,000 rpm for 5 minutes using an Eppendorf centrifuge 5810R with an A-4-81 rotor. The medium was aspirated off. For the compound screening, a parasite dilution at a 1% parasitemia and 1.0% hematocrit was created with screening medium (RPMI with L-glutamine, 4.16 mg/ml albumax II, 0.013 mg/ml hypoxanthine, 1.73 mg/ml glucose, 0.18% $NaHCO_3$, 0.031 M Hepes, 2.60 mM NaOH, and 0.043 mg/ml gentamicin). The suspension was gassed with 93% nitrogen, 4% carbon dioxide, and 3% oxygen and placed at 37° C. until needed. Using a liquid dispenser, 20 µl of screening medium was dispensed into 384-well, black, clear-bottom plates. With a PinTool, 100 nl of compounds dissolved in DMSO was transferred into the assay plates along with control compound (mefloquine). Next, 30 µl of the parasite suspension in screening medium was then dispensed into the assay plates such that the final parasitemia was 1% and the final hematocrit was 1.0%. Final concentration of DMSO was 0.125%. Mefloquine at a final concentration of 20 µM and DMSO at a final concentration of 0.125% were used within the assay plates to serve as background and baseline controls, respectively. The assay plates were transferred to incubators (93% nitrogen, 4% carbon dioxide, and 3% oxygen during the 72 h incubation at 37° C.). Ten microliters of detection reagent consisting of 10×SYBR Green I (Invitrogen; supplied in 10,000× concentration) in lysis buffer (20 mM Tris-HCl, 5 mM EDTA, 0.16% Saponin wt/vol, 1.6% Triton X vol/vol) was dispensed into the assay plates. For optimal staining, the assay plates were left at room temperature for 24 h in the dark. The assay plates were read by using an Envision (PerkinElmer) reader, with 505 dichroic mirrors with 485-nm excitation and 530-nm emission settings, and the plate reads were from the bottom.

By following the above-described protocol, the 50% effective concentration ($EC_{50}$) for compounds 1-95 was measured against *P. falciparum* Dd2 and the results are shown in Table 2:

TABLE 2

| Compound Number | $EC_{50}$ Dd2 (nM) |
|---|---|
| 1 | 427 |
| 2 | 165 |
| 3 | 118 |
| 4 | 131 |
| 5 | 1066 |
| 6 | 552 |
| 7 | 1194 |
| 8 | 83 |
| 9 | 518 |
| 10 | 949 |
| 11 | 17 |
| 12 | 950 |
| 13 | 44 |
| 14 | 1196 |
| 15 | 254 |
| 16 | 618 |
| 17 | 560 |
| 18 | 800 |
| 19 | 805 |
| 20 | 1326 |
| 21 | 623 |
| 22 | 507 |
| 23 | 386 |
| 24 | 418 |
| 25 | 155 |
| 26 | 955 |
| 27 | 4 |
| 28 | 368 |
| 29 | 898 |
| 30 | 42 |
| 31 | 1824 |
| 32 | 158 |
| 33 | 2324 |
| 34 | 4659 |
| 35 | 65 |
| 36 | 7900 |
| 37 | 148 |
| 38 | 15 |
| 39 | 5170 |
| 40 | 5160 |
| 41 | 9830 |
| 42 | 9680 |
| 43 | 229 |
| 44 | 1097 |
| 45 | 846 |
| 46 | 17828 |
| 47 | 23 |
| 48 | 36 |
| 49 | 65 |
| 50 | 1234 |
| 51 | 11 |

TABLE 2-continued

| Compound Number | $EC_{50}$ Dd2 (nM) |
|---|---|
| 52 | 17 |
| 53 | 2771 |
| 54 | 156 |
| 55 | 5 |
| 56 | 80 |
| 57 | 98 |
| 58 | 6 |
| 59 | 2700 |
| 60 | 61 |
| 61 | 47 |
| 62 | 4430 |
| 63 | 1229 |
| 64 | 1010 |
| 65 | 110 |
| 66 | 1313 |
| 67 | 19500 |
| 68 | 3 |
| 69 | 19500 |
| 70 | 13 |
| 71 | 34 |
| 72 | 17 |
| 73 | 104 |
| 74 | 87 |
| 75 | 71 |
| 76 | 8 |
| 77 | 4886 |
| 78 | 61 |
| 79 | 850 |
| 80 | 23 |
| 81 | 34 |
| 82 | 3 |
| 83 | 24 |
| 84 | 52 |
| 85 | 0.4 |
| 86 | 2 |
| 87 | 1 |
| 88 | 25 |
| 89 | 8 |
| 90 | 228 |
| 91 | 14 |
| 92 | 108 |
| 93 | 138 |
| 94 | 14 |
| 95 | 5000 |

Example 3. In Vivo PK/Efficacy of Selected Compounds

In vivo antimalarial activity for certain compounds of the invention was assessed for groups of three-five female NMVRI mice (20-22 mg) intravenously infected on day 0 with *P. berghei* strain ANKA ($2\times10^7$ parasitized erythrocytes per ml). In control mice, parasitemia typically rose to ~40% by day 3 after infection, and control mice died between day 5 and day 7 after infection. Compounds with a dosage of 50 mg/kg were formulated in 7% Tween80/3% ethanol and were administered orally as three consecutive daily doses (24, 48, and 72 h after infection). The blood smears were collected and stained on day 4 after infection. The degree of infection (parasitemia expressed as percent infected erythrocytes) was determined microscopically, with a detection limit of 1 parasite in 10,000 erythrocytes (that is, 0.01%). Activity was calculated as the difference between the mean percent parasitemia for the control and treated groups expressed as a percent relative to the control group. Using this method, a compound of the invention (8R,9R,10S)-10-(hydroxymethyl)-N-(4-methoxyphenyl)-9-(4-(phenylethynyl)phenyl)-1,6-diazabicyclo[6.2.0]decane-6-carboxamide (compound 27) reduced parasitaemia by 57% on day 4. For pharmacokinetics analyses, blood samples were collected at 1, 4, and 24 hours after dosing and were immediately centrifuged and the plasma separated and frozen at −20° C. Before analysis by LC/MS, plasma proteins were precipitated by the addition of acetonitrile (2:1 v/v). Quantification was conducted by comparison to a calibration curve prepared using blank plasma and processed in the same way as the samples.

Example 4. Single Dose In Vivo Efficacy of Selected Compounds

CD-1 mice (female, 6-7-week-old) were inoculated with $1\times10^6$ *P. berghei* (ANKA GFP-luc) blood stage parasites intravenously 24 hours before treatment and compounds were administered as a single 100 or 50 mg/kg dose orally at 0 hour. Parasitemia was monitored by the In vivo Imaging System (IVIS 100, Xenogen; Caliper Life Science) to acquire the bioluminescence signal. Animals with parasitemia exceeding 25% were euthanized.

The results are shown in FIG. 1 (Panels A and B). Infection proceeds rapidly in untreated mice (control), which were euthanized around day 6 of the study. Compound 37 and 68 were tested at different times; thus the artesunate control (ART) is shown for each compound. A single 100 mg/kg dose of ART results in rapid suppression of parasites, but, due to its short half-life, the parasites re-emerge quickly. A single 100 mg/kg dose of compound 37 repressed parasitemia for about 1 week ($ED_{25}=100$ mg/kg in this study), while a single 50 mg/kg dose of compound 68 resulted in 100% cure of the infected animals ($ED_{100}\leq50$ mg/kg). All images are normalized to the same color scale.

Example 5. Prevention of Transmission of *P. berghei* to Mosquitoes

CD-1 mice were infected with *P. berghei* (ANKA GFP-luc) for 96 hours prior to treatment with vehicle [70% PEG400 and 30% (5% glucose in $H_2O$)] or single ascending doses of compound 37 (Day 0). Average % parasitemia on Day 0 was 2.1%. On Day 2 of the study, mice were anesthetized and female *Anopheles stephensi* mosquitoes were allowed to feed on the mice for 20 minutes. On Day 9, the midguts of the mosquitoes were dissected out, and oocysts were enumerated microscopically (12.5× magnification, oocysts visible as puncta in the control, FIG. 2, Panel A).

Figure 2:
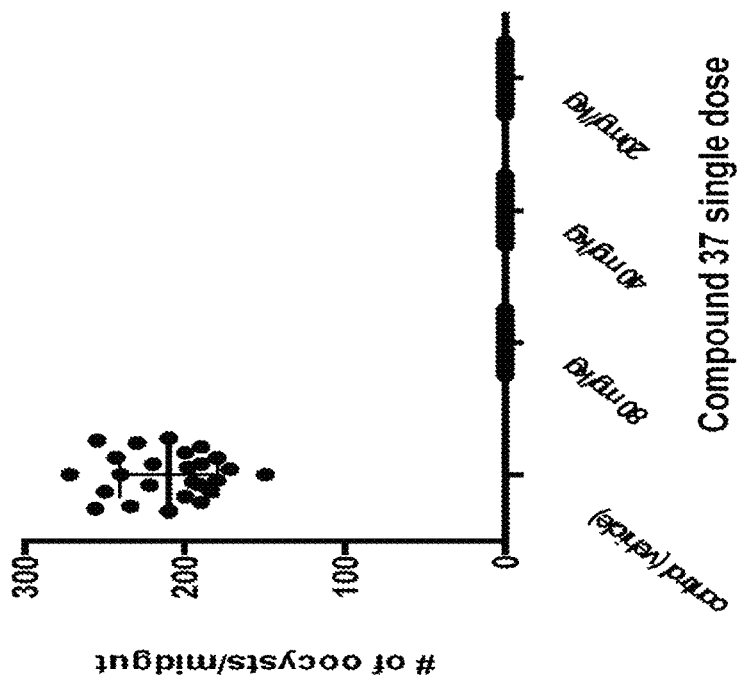
FIG. 2, Panel A, provides microscopic images of oocysts from the midguts of mosquitoes that were allowed to feed on mice that had been infected with *P. berghei* and then treated with vehicle or compound 37. A graphical representation of the results of this experiment is provided in FIG. 2, Panel B (see Example 5, below, for details).
Figure 2:
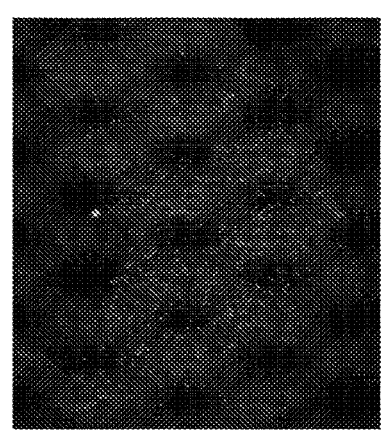
Figure 2:
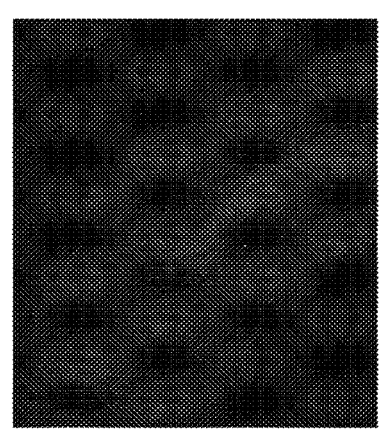

Mosquitoes fed on untreated mice had many visible oocysts (210.4±30.6), while mosquitoes fed on compound 37 animals (all doses) had no detectable oocysts (FIG. 2, Panel B).

Example 6. In Vivo *P. berghei* Liver Stage Assay

CD-1 mice were inoculated (IV) with $1\times10^5$ *P. berghei* (ANKA luc-GFP) sporozoites freshly dissected out from *A. stephensi* and immediately treated with a single dose (PO) of vehicle or compound 37 (25, 5.0, 1.0 or 0.2 mg/kg) at 0 hour. Bioluminescence signals from the transgenic parasites were monitored by the In vivo Imaging System (IVIS 100, Xenogen; Caliper Life Science).

Figure 3:
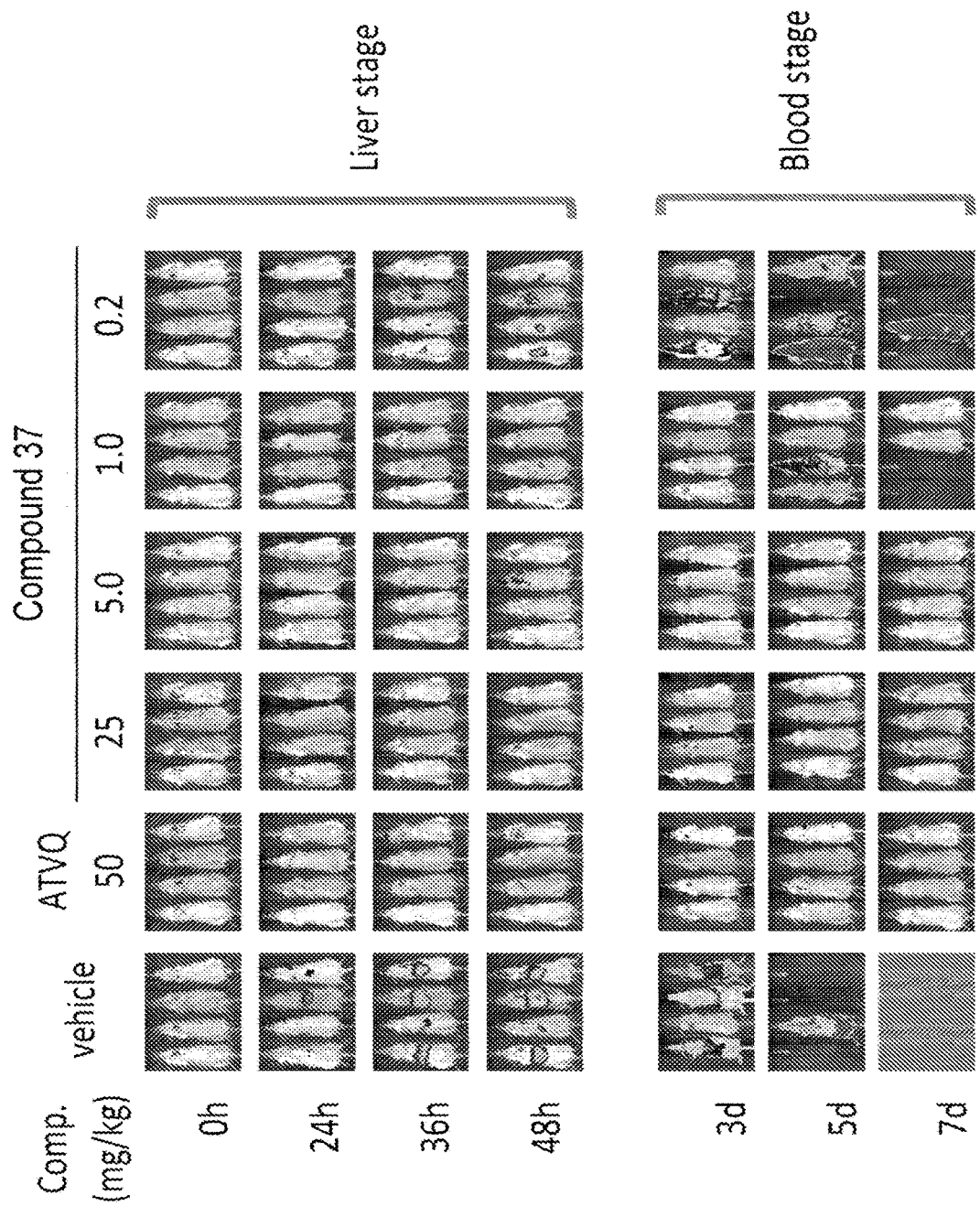
FIG. 3 provides images of CD-1 mice inoculated with *P. berghei* sporozoites before treatment with vehicle, ATVQ, or compound 37 (see Example 6, below, for details).

Untreated control animals showed systemic (blood stage) parasitemia by day 3; while atovaquone (ATV) and compound 37-treated animals (dosed at ≥5 mg/kg) remained parasite free (FIG. 3), demonstrating effective inhibition of liver stage parasites. The $ED_{50}$ for compound 37 in this assay was 1 mg/kg.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

The invention is further described in the following numbered paragraphs.

1. A compound according to formula (I):

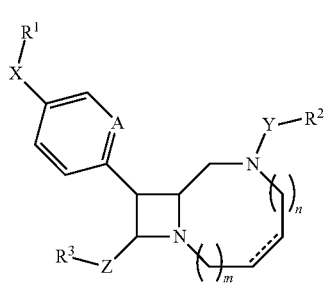

Formula I wherein the dotted line represents an optional double bond;

m is 0 or 1;
n is 0, 1, or 2;
A is CH or N;
X is absent or —C≡C—;
$R^1$ is hydrogen, $C_1$-$C_6$ alkyl, $C_1$-$C_6$ heteroalkyl, $C_6$-$C_{10}$ aryl, $C_3$-$C_{10}$ carbocyclyl, or $C_2$-$C_9$ heteroaryl;
Y is $C_1$-$C_6$ alkylene, —C(O)NR$^4$—; —SO$_2$—, or —C(O)—;
$R^2$ is $C_1$-$C_6$ perfluoroalkyl, $C_6$-$C_{10}$ aryl, $C_6$-$C_{10}$ aryl $C_1$-$C_6$ alkyl, $C_3$-$C_{10}$ carbocyclyl, or $C_2$-$C_9$ heteroaryl;
Z is absent, $C_1$-$C_6$ alkylene, or $C_1$-$C_6$ heteroalkylene;
$R^3$ is hydrogen, hydroxyl, —NR$^5$R$^6$, —C(O)R$^7$, or $C_2$-$C_9$ heterocyclyl;
$R^4$ is hydrogen or $C_1$-$C_6$ alkyl;
$R^5$ and $R^6$ are independently hydrogen, $C_1$-$C_6$ alkyl, or $C_1$-$C_6$ acyl; and
$R^7$ is hydroxyl, $C_1$-$C_6$ heteroalkyl, or $C_2$-$C_9$ heterocyclyl;
wherein said compound does not have the structure of any one of compounds 1 to 30 of Table 1;
or a pharmaceutically acceptable salt thereof.

2. The compound of paragraph 1, wherein said compound has the structure:

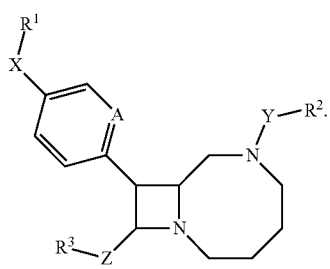

Formula II

3. The compound of paragraph 1, wherein said compound has the structure:

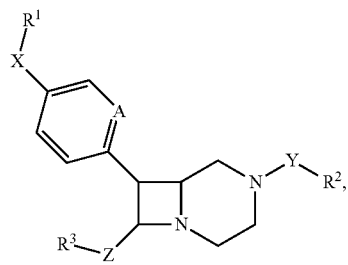

Formula III

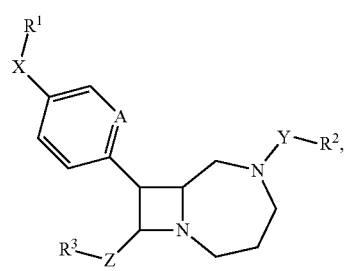

Formula IV

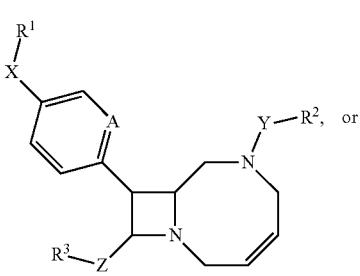

Formula V

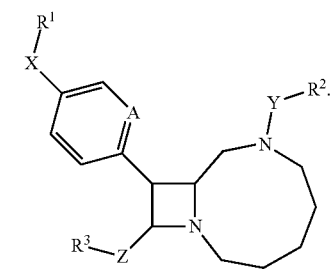

Formula VI

4. The compound of any one of paragraphs 1 to 3, wherein X is —C≡C—.

5. The compound of any one of paragraphs 1 to 4, wherein $R^1$ is $C_6$-$C_{10}$ aryl.

6. The compound of any one of paragraphs 1 to 5, wherein Y is —C(O)NR$^4$—.

7. The compound of any one of paragraphs 1 to 6, wherein $R^2$ is $C_6$-$C_{10}$ aryl, $C_3$-$C_{10}$ carbocyclyl, or $C_2$-$C_9$ heteroaryl.

8. The compound of any one of paragraph 1, wherein said compound has the structure:

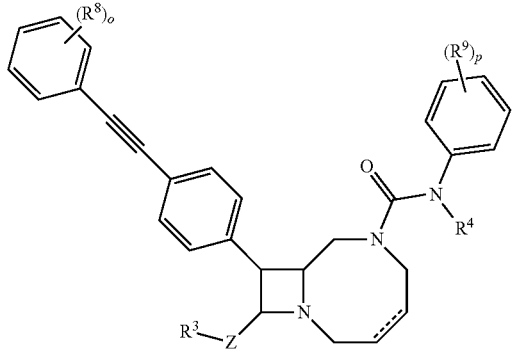

Formula VII wherein o and p are independently 1, 2, 3, 4, or 5; and $R^8$ and $R^9$ are independently hydrogen, halogen, or $C_1$-$C_6$ heteroalkyl.

9. The compound of any one of paragraphs 1 to 8, wherein —$ZR^3$ is hydrogen or —$CO_2H$.

10. The compound of any one of paragraphs 1 to 8, wherein Z is methylene.

11. The compound of any one of paragraphs 1, 2, 8, or 10, wherein $R^3$ is hydroxyl, 4-methylpiperazyl, 4-hydroxy-4-methyl-piperidyl, 3-hydroxyl-3-methyl-azetidinyl, —$OCH_2C(O)OH$, —$NH_2$, morpholinyl, —$NHC(O)CH_3$, —$NHCH_3$, —$N(CH_3)_2$, or —$N(CH_3)C(O)CH_3$.

12. The compound of any one of paragraphs 1 to 8 or 11, wherein Z is —$CH_2OCH_2$— or —$CH_2OCH_2CH_2$.

13. The compound of any one of paragraphs 1 to 8, 10, or 12, wherein $R^3$ is $C(O)R^7$.

14. The compound of paragraph 13, wherein $R^7$ is hydroxyl, methoxy, or morpholino.

15. The compound of any one of paragraphs 1 to 5, or 9 to 14, wherein —$YR^2$ is —$CH_2CH_2CF_3$.

16. The compound of any one of paragraphs 1 to 5, 7, or 9 to 14, wherein Y is methylene or —$SO_2$—.

17. The compound of any one of paragraphs 1 to 14 or 16, wherein $R^2$ is 4-methoxy-phenyl.

18. The compound of any one of paragraphs 1 to 4, 6, 7, or 9 to 17, wherein $R^1$ is $C_2$-$C_9$ heteroaryl.

19. The compound of paragraph 18, wherein said $C_2$-$C_9$ heteroaryl is 2-pyridyl or 3-pyridyl.

20. The compound of paragraph 18 or 19, wherein Y is —$C(O)NH$—.

21. The compound of paragraph 20, wherein $R^2$ is $C_6$-$C_{10}$ aryl.

22. The compound of any one of paragraphs 1 to 8, or 15 to 21, wherein —$ZR^3$ is hydrogen, —$CH_2OH$, —$CH_2NH_2$, or —$CH_2NHC(O)CH_3$.

23. The compound of paragraph 18 or 19, wherein Y is methylene.

24. The compound of any one of paragraphs 1 to 14, 16, or 18 to 22, wherein $R^2$ is 3-methoxy-phenyl.

25. The compound of any one of paragraphs 1 to 4, 5 to 7, 9 to 17, or 20 to 24, wherein $R^1$ is iso-butyl, —$CH_2OCH_3$, cyclopropyl, cyclopentyl, or cyclohexyl.

26. The compound of paragraph 25, wherein Y is —$C(O)NH$—.

27. The compound of paragraph 26, wherein $R^2$ is 2-methoxy-phenyl or 4-methoxy-phenyl.

28. The compound of paragraph 25, wherein Y is —$SO_2$—.

29. The compound of any one of paragraphs 1 to 6, 9 to 14, 16, 18 to 20, 22, 23, 25, 26, or 28, wherein $R^2$ is 4-methoxy-phenyl or benzyl.

30. The compound of any one of paragraphs 1 to 3, 5 to 7, or 9 to 29, wherein X is absent.

31. The compound of paragraph 30, wherein $R^1$ is hydrogen, phenyl, 2-fluoro-phenyl, 3-fluorophenyl, 4-fluoro-phenyl, 3-methyl-phenyl, 4-methyl-phenyl, cyclohexenyl, 2-phenyl-1,3-thiazol-4-yl, 1-phenyl-pyrrol-3-yl, 4-pyridyl, or 1-phenyl-1H-pyrazol-3-yl.

32. The compound of paragraph 30 or 31, wherein —$ZR^3$ is —$CH_2OH$.

33. The compound of any one of paragraphs 30 to 32, wherein —$YR^2$ is —$CH_2CH_2CF_3$.

34. The compound of any one of paragraphs 30 to 32, wherein Y is —$SO_2$— and $R^2$ is 3-methyl-phenyl or 4-fluoro-phenyl.

35. The compound of any one of paragraphs 30 to 32, wherein Y is —$C(O)NH$— and $R^2$ is 4-methoxy-phenyl.

36. The compound of any one of paragraphs 1 to 35, wherein A is CH.

37. The compound of any one of paragraphs 1 to 35, wherein A is N.

38. A compound having the structure of any one of compounds 31 to 95 of Table 1 or a pharmaceutically acceptable salt thereof.

39. A pharmaceutical composition comprising a therapeutically effective amount of a compound having the structure:

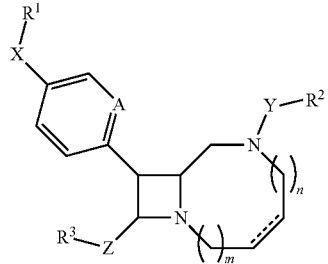

Formula I wherein the dotted line represents an optional double bond;
m is 0 or 1;
n is 0, 1, or 2;
A is CH or N;
X is absent or —C≡C—;
$R^1$ is hydrogen, $C_1$-$C_6$ alkyl, $C_1$-$C_6$ heteroalkyl, $C_6$-$C_{10}$ aryl, $C_3$-$C_{10}$ carbocyclyl, or $C_2$-$C_9$ heteroaryl;
Y is $C_1$-$C_6$ alkylene, —$C(O)NR^4$—; —$SO_2$—, or —$C(O)$—;
$R^2$ is $C_1$-$C_6$ perfluoroalkyl, $C_6$-$C_{10}$ aryl, $C_6$-$C_{10}$ aryl $C_1$-$C_6$ alkyl, $C_3$-$C_{10}$ carbocyclyl, or $C_2$-$C_9$ heteroaryl;
Z is absent, $C_1$-$C_6$ alkylene, or $C_1$-$C_6$ heteroalkylene;
$R^3$ is hydrogen, hydroxyl, —$NR^5R^6$, —$C(O)R^7$, or $C_2$-$C_9$ heterocyclyl;
$R^4$ is hydrogen or $C_1$-$C_6$ alkyl;
$R^5$ and $R^6$ are independently hydrogen, $C_1$-$C_6$ alkyl, or $C_1$-$C_6$ acyl; and
$R^7$ is hydroxyl, $C_1$-$C_6$ heteroalkyl, or $C_2$-$C_9$ heterocyclyl;
or a pharmaceutically acceptable salt thereof; and
a pharmaceutically acceptable excipient.

40. The pharmaceutical composition of paragraph 39, wherein said compound has the structure of any one of compounds 1 to 95 of Table 1 or a pharmaceutically acceptable salt thereof.

41. The pharmaceutical composition of paragraph 39, wherein said compound has the structure of any one of paragraphs 2 to 37.

42. A method of preventing or treating malaria in a subject, comprising the step of administering to the subject an effective amount of a compound having the structure:

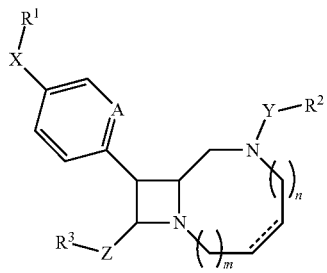

Formula I wherein the dotted line represents an optional double bond;

m is 0 or 1;

n is 0, 1, or 2;

A is CH or N;

X is absent or —C≡C—;

$R^1$ is hydrogen, $C_1$-$C_6$ alkyl, $C_1$-$C_6$ heteroalkyl, $C_6$-$C_{10}$ aryl, $C_3$-$C_{10}$ carbocyclyl, or $C_2$-$C_9$ heteroaryl;

Y is $C_1$-$C_6$ alkylene, —C(O)$NR^4$—; —$SO_2$—, or —C(O)—;

$R^2$ is $C_1$-$C_6$ perfluoroalkyl, $C_6$-$C_{10}$ aryl, $C_6$-$C_{10}$ aryl $C_1$-$C_6$ alkyl, $C_3$-$C_{10}$ carbocyclyl, or $C_2$-$C_9$ heteroaryl;

Z is absent, $C_1$-$C_6$ alkylene, or $C_1$-$C_6$ heteroalkylene;

$R^3$ is hydrogen, hydroxyl, —$NR^5R^6$, —C(O)$R^7$, or $C_2$-$C_9$ heterocyclyl;

$R^4$ is hydrogen or $C_1$-$C_6$ alkyl;

$R^5$ and $R^6$ are independently hydrogen, $C_1$-$C_6$ alkyl, or $C_1$-$C_6$ acyl; and $R^7$ is hydroxyl, $C_1$-$C_6$ heteroalkyl, or $C_2$-$C_9$ heterocyclyl; or a pharmaceutically acceptable salt thereof.

43. The method of paragraph 42, wherein said compound has the structure of any one of compounds 1 to 95 of Table 1 or a pharmaceutically acceptable salt thereof.

44. The method of paragraph 42 or 43, wherein said malaria is drug resistant malaria.

45. The method of paragraph 44, wherein drug resistant malaria is resistant to chloroquine, quinine, prymethamine, sulfadoxine, mefloquine, artemether, lumefantrine, artesunate, amodiaquine, dihydroartemisinin, piperaquine, proguanil, doxycycline, clindamycin, artemisinin, atovaquone, or any combination thereof.

46. The method of any one of paragraphs 42 to 45, wherein said malaria is liver stage malaria.

47. The method of any one of paragraphs 42 to 46, wherein the liver of said subject is infected with a malaria-causing parasite and said treatment prevents spread of said infection from their liver.

48. The method of any one of paragraphs 42 to 45, wherein said malaria is blood stage malaria.

49. The method of any one of paragraphs 42 to 45, wherein said malaria is transmission stage malaria.

50. The method of any one of paragraphs 42 or 44 to 49, wherein said compound has the structure of any one of paragraphs 2 to 37.

What is claimed is:

1. A compound according to formula (I):

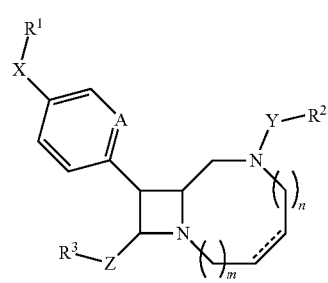

Formula I wherein the dotted line represents an optional double bond;

m is 0 or 1;

n is 0, 1, or 2;

A is CH or N;

X is absent or —C≡C—;

$R^1$ is hydrogen, $C_1$-$C_6$ alkyl, $C_1$-$C_6$ heteroalkyl, $C_6$-$C_{10}$ aryl, or $C_2$-$C_9$ heteroaryl;

Y is $C_1$-$C_6$ alkylene;

$R^2$ is $C_1$-$C_6$ perfluoroalkyl, $C_6$-$C_{10}$ aryl, $C_6$-$C_{10}$ aryl $C_1$-$C_6$ alkyl, or $C_3$-$C_{10}$ carbocyclyl, wherein $R^2$ is not 2-methoxyphenyl;

Z is absent, $C_1$-$C_6$ alkylene, or $C_1$-$C_6$ heteroalkylene;

$R^3$ is hydrogen, hydroxyl, —$OCH_2C(O)OH$, —$NR^5R^6$, —C(O)$R^7$, or $C_2$-$C_9$ heterocyclyl;

$R^4$ is hydrogen or $C_1$-$C_6$ alkyl;

$R^5$ and $R^6$ are independently hydrogen, $C_1$-$C_6$ alkyl, or $C_1$-$C_6$ acyl; and $R^7$ is hydroxyl, $C_1$-$C_6$ heteroalkyl, or $C_2$-$C_9$ heterocyclyl; or a pharmaceutically acceptable salt thereof.

2. The compound of claim 1, wherein said compound has the structure:

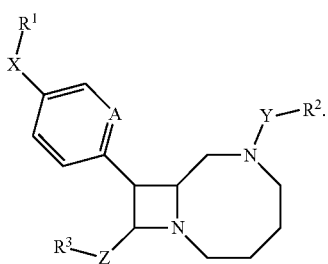

Formula II

3. The compound of claim 1, wherein said compound has the structure:

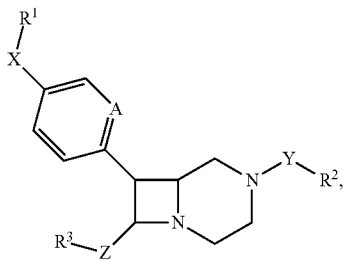

Formula III

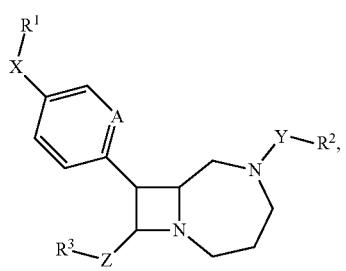

Formula IV

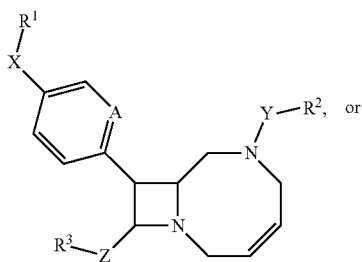

Formula V

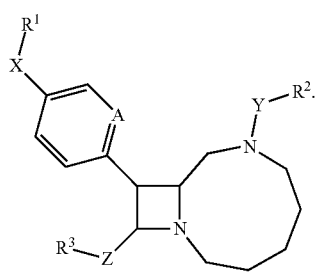

Formula VI

4. The compound of claim 1, wherein X is —C≡C—.
5. The compound of claim 1, wherein $R^1$ is $C_6$-$C_{10}$ aryl.
6. The compound of claim 1, wherein $R^2$ is $C_6$-$C_{10}$ aryl.
7. The compound of claim 1, wherein Z is methylene.
8. The compound of claim 1, wherein $R^3$ is hydroxyl, 4-methylpiperazyl, 4-hydroxy-4-methyl-piperidyl, 3-hydroxyl-3-methyl-azetidinyl, —OCH$_2$C(O)OH, —NH$_2$, morpholinyl, —NHC(O)CH$_3$, —NHCH$_3$, —N(CH$_3$)$_2$, or —N(CH$_3$)C(O)CH$_3$.
9. The compound claim 1, wherein Y is methylene.
10. The compound of claim 1, wherein $R^2$ is substituted phenyl.

11. A pharmaceutical composition comprising a therapeutically effective amount of a compound having the structure:

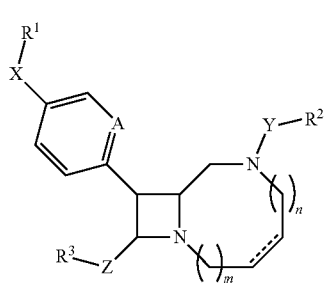

Formula I wherein the dotted line represents an optional double bond;
m is 0 or 1;
n is 0, 1, or 2;
A is CH or N;
X is absent or —C≡C—;
$R^1$ is hydrogen, $C_1$-$C_6$ alkyl, $C_1$-$C_6$ heteroalkyl, $C_6$-$C_{10}$ aryl, or $C_2$-$C_9$ heteroaryl;
Y is $C_1$-$C_6$ alkylene;
$R^2$ is $C_1$-$C_6$ perfluoroalkyl, $C_6$-$C_{10}$ aryl, $C_6$-$C_{10}$ aryl $C_1$-$C_6$ alkyl, or $C_3$-$C_{10}$ carbocyclyl, wherein $R^2$ is not 2-methoxyphenyl;
Z is absent, $C_1$-$C_6$ alkylene, or $C_1$-$C_6$ heteroalkylene;
$R^3$ is hydrogen, hydroxyl, —OCH$_2$C(O)OH, —NR$^5$R$^6$, —C(O)R$^7$, or $C_2$-$C_9$ heterocyclyl;
$R^4$ is hydrogen or $C_1$-$C_6$ alkyl;
$R^5$ and $R^6$ are independently hydrogen, $C_1$-$C_6$ alkyl, or $C_1$-$C_6$ acyl; and
$R^7$ is hydroxyl, $C_1$-$C_6$ heteroalkyl, or $C_2$-$C_9$ heterocyclyl;
or a pharmaceutically acceptable salt thereof, and
a pharmaceutically acceptable excipient.

12. A method of preventing or treating malaria in a subject, comprising the step of administering to the subject an effective amount of a compound having the structure:

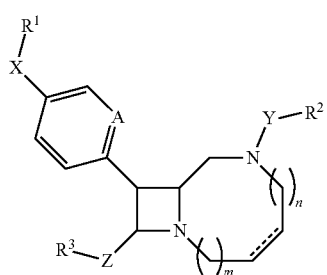

Formula I wherein the dotted line represents an optional double bond;
m is 0 or 1;
n is 0, 1, or 2;
A is CH or N;
X is absent or —C≡C—;
$R^1$ is hydrogen, $C_1$-$C_6$ alkyl, $C_1$-$C_6$ heteroalkyl, $C_6$-$C_{10}$ aryl, or $C_2$-$C_9$ heteroaryl;
Y is $C_1$-$C_6$ alkylene;
$R^2$ is $C_1$-$C_6$ perfluoroalkyl, $C_6$-$C_{10}$ aryl, $C_6$-$C_{10}$ aryl $C_1$-$C_6$ alkyl, or $C_3$-$C_{10}$ carbocyclyl, wherein $R^2$ is not 2-methoxyphenyl;

Z is absent, $C_1$-$C_6$ alkylene, or $C_1$-$C_6$ heteroalkylene;

$R^3$ is hydrogen, hydroxyl, —$NR^5R^6$, —$OCH_2C(O)OH$, —$C(O)R^7$, or $C_2$-$C_9$ heterocyclyl;

$R^4$ is hydrogen or $C_1$-$C_6$ alkyl;

$R^5$ and $R^6$ are independently hydrogen, $C_1$-$C_6$ alkyl, or $C_1$-$C_6$ acyl; and $R^7$ is hydroxyl, $C_1$-$C_6$ heteroalkyl, or $C_2$-$C_9$ heterocyclyl;

or a pharmaceutically acceptable salt thereof.

13. The method of claim 12, wherein said malaria is drug resistant malaria.

14. The method of claim 13, wherein drug resistant malaria is resistant to chloroquine, quinine, prymethamine, sulfadoxine, mefloquine, artemether, lumefantrine, artesunate, amodiaquine, dihydroartemisinin, piperaquine, proguanil, doxycycline, clindamycin, artemisinin, atovaquone, or any combination thereof.

15. The method of claim 12, wherein said malaria is liver stage malaria, blood stage malaria, or transmission stage malaria.

16. The method of claim 12, wherein the liver of said subject is infected with a malaria-causing parasite and said treatment prevents spread of said infection from their liver.

17. The compound according to claim 1, wherein $R^2$ is phenyl substituted with —$CH_3$, —$OCH_3$ or halogen.

18. The compound according to claim 1, wherein $R^2$ is phenyl substituted with halogen.

19. The compound according to claim 1, wherein $R^2$ is not 3-methoxyphenyl or 4-methoxyphenyl.

20. The compound according to claim 1, wherein $R^1$ is substituted phenyl.

* * * * *